United States Patent
Lemoine et al.

(10) Patent No.: US 10,343,160 B2
(45) Date of Patent: Jul. 9, 2019

(54) CARTRIDGE ASSEMBLY

(71) Applicants: ILLUMINA, INC., San Diego, CA (US); ILLUMINA, SINGAPORE PTE. LTD., Singapore (SG)

(72) Inventors: Richard L. Lemoine, Canton, CT (US); James Osmus, San Diego, CA (US); Sz-Chin Steven Lin, Ladera Ranch, CA (US); Beng Keong Ang, Singapore (SG)

(73) Assignees: ILLUMINA, INC., San Diego, CA (US); ILLUMINA, SINGAPORE PTE. LTD., Singapore (SG)

(*) Notice: Subject to any disclaimer, the term of this patent is extended or adjusted under 35 U.S.C. 154(b) by 0 days.

(21) Appl. No.: 15/729,729

(22) Filed: Oct. 11, 2017

(65) Prior Publication Data
US 2018/0117587 A1    May 3, 2018

Related U.S. Application Data

(60) Provisional application No. 62/408,631, filed on Oct. 14, 2016.

(30) Foreign Application Priority Data

Dec. 8, 2016 (NL) ........................... 2017959

(51) Int. Cl.
*B01L 3/00* (2006.01)
*G01N 21/01* (2006.01)
(Continued)

(52) U.S. Cl.
CPC ..... *B01L 3/502715* (2013.01); *B01L 3/50273* (2013.01); *B01L 3/502738* (2013.01);
(Continued)

(58) Field of Classification Search
CPC ............................. B01L 3/502; B01L 2400/06
(Continued)

(56) References Cited

U.S. PATENT DOCUMENTS

| 5,641,658 A | 6/1997 | Adams et al. |
| 6,210,891 B1 | 4/2001 | Nyren et al. |

(Continued)

FOREIGN PATENT DOCUMENTS

| WO | 1991/006678 A1 | 5/1991 |
| WO | 98/59066 A1 | 12/1998 |

(Continued)

OTHER PUBLICATIONS

"International Search Report, NL 2017959", dated Aug. 31, 2017.
(Continued)

*Primary Examiner* — Natalia Levkovich
(74) *Attorney, Agent, or Firm* — Illumina, Inc.

(57) ABSTRACT

A cartridge assembly that comprises a housing, including a flow cell chamber to receive a flow cell, and a well plate having liquid wells to receive desired amounts of liquids. The well plate includes a valve station, a pump station and a fluidics analysis station, and channels associated therewith. A pump assembly to manage fluid flow through the channels between the pump station and the fluidics analysis station. A rotary valve assembly that includes a rotor shaft and rotor valve positioned to rotate about a rotational axis and to selectively couple the wells to the pump station. The rotor shaft includes a dual spline configuration at the distal end thereof. The dual spline configuration has first and second sets of splines. The first set of splines forms a drive interface and the second set of splines forms a position encoding interface.

16 Claims, 22 Drawing Sheets

(51) Int. Cl.
  *G01N 21/75* (2006.01)
  *F04B 19/00* (2006.01)
  *F16K 99/00* (2006.01)
  *G01N 21/00* (2006.01)

(52) U.S. Cl.
  CPC ........ *F04B 19/006* (2013.01); *F16K 99/0001* (2013.01); *G01N 21/00* (2013.01); *G01N 21/01* (2013.01); *G01N 21/75* (2013.01); *B01L 2200/02* (2013.01); *B01L 2200/025* (2013.01); *B01L 2200/026* (2013.01); *B01L 2200/028* (2013.01); *B01L 2200/16* (2013.01); *B01L 2300/042* (2013.01); *B01L 2300/0609* (2013.01); *B01L 2300/0672* (2013.01); *B01L 2300/0829* (2013.01); *B01L 2400/0478* (2013.01); *B01L 2400/0644* (2013.01)

(58) Field of Classification Search
  USPC .................................................. 422/554, 417
  See application file for complete search history.

(56) References Cited

U.S. PATENT DOCUMENTS

| | | |
|---|---|---|
| 6,258,568 B1 | 7/2001 | Nyren |
| 6,274,320 B1 | 8/2001 | Rothberg et al. |
| 6,783,736 B1 | 8/2004 | Taylor et al. |
| 7,001,792 B2 | 2/2006 | Sauer et al. |
| 7,057,026 B2 | 6/2006 | Barnes et al. |
| 7,115,400 B1 | 10/2006 | Adessi et al. |
| 7,211,414 B2 | 5/2007 | Hardin et al. |
| 7,315,019 B2 | 1/2008 | Turner et al. |
| 7,329,492 B2 | 2/2008 | Hardin et al. |
| 7,329,860 B2 | 2/2008 | Feng et al. |
| 7,405,281 B2 | 7/2008 | Xu et al. |
| 7,414,116 B2 | 8/2008 | Milton et al. |
| 7,427,673 B2 | 9/2008 | Balasubramanian et al. |
| 7,541,444 B2 | 6/2009 | Milton et al. |
| 7,566,537 B2 | 7/2009 | Balasubramanian et al. |
| 7,592,435 B2 | 9/2009 | Milton et al. |
| 7,595,883 B1 | 9/2009 | El Gamal et al. |
| 9,127,313 B2 | 9/2015 | Brown et al. |
| 9,404,881 B2 | 8/2016 | Glezer et al. |
| 2002/0055100 A1 | 5/2002 | Kawashima et al. |
| 2003/0108367 A1 | 6/2003 | Chee et al. |
| 2003/0108900 A1 | 6/2003 | Oliphant et al. |
| 2003/0170684 A1 | 9/2003 | Fan |
| 2003/0207295 A1 | 11/2003 | Gunderson et al. |
| 2004/0002090 A1 | 1/2004 | Mayer et al. |
| 2004/0096853 A1 | 5/2004 | Mayer |
| 2005/0042648 A1 | 2/2005 | Griffiths et al. |
| 2005/0064460 A1 | 3/2005 | Holliger et al. |
| 2005/0079510 A1 | 4/2005 | Berka et al. |
| 2005/0100900 A1 | 5/2005 | Kawashima et al. |
| 2005/0130173 A1 | 6/2005 | Leamon et al. |
| 2005/0181394 A1 | 8/2005 | Steemers et al. |
| 2006/0188901 A1 | 8/2006 | Barnes et al. |
| 2006/0240439 A1 | 10/2006 | Smith et al. |
| 2006/0281109 A1 | 12/2006 | Barr Ost et al. |
| 2007/0099208 A1 | 5/2007 | Drmanac et al. |
| 2007/0128624 A1 | 6/2007 | Gormley et al. |
| 2007/0166705 A1 | 7/2007 | Milton et al. |
| 2008/0009420 A1 | 1/2008 | Schroth et al. |
| 2008/0108082 A1 | 5/2008 | Rank et al. |
| 2009/0272914 A1 | 11/2009 | Feng et al. |
| 2010/0157086 A1 | 2/2010 | Segale |
| 2014/0004621 A1* | 1/2014 | Dority ................... B01L 3/502 436/178 |

FOREIGN PATENT DOCUMENTS

| | | |
|---|---|---|
| WO | 2004/018497 A2 | 3/2004 |
| WO | 2005/010145 A1 | 2/2005 |
| WO | 2005/065814 A1 | 7/2005 |
| WO | 2006/064199 A1 | 6/2006 |
| WO | 2006/065598 | 6/2006 |
| WO | 2007/010251 A2 | 1/2007 |
| WO | 2007/123744 A2 | 11/2007 |
| WO | 2007/135368 A2 | 11/2007 |
| WO | 2009/042862 A1 | 4/2009 |
| WO | 2009137435 A1 | 11/2009 |
| WO | 2014/008381 A2 | 1/2014 |
| WO | 2009/021215 | 6/2014 |
| WO | 2014/100456 | 6/2014 |
| WO | 2015/138648 A1 | 9/2015 |

OTHER PUBLICATIONS

Bentley, et al., "Accurate whole human genome sequencing using reversible terminator chemistry", Nature, vol. 456, Nov. 6, 2008, 53-59.

Cockroft, et al., "A single-molecule nanpore device detects DNA polymerase activity with single-nucleotide resolution", J. Am. Chem. Soc, 130(3), Jan. 23, 2008, 818-820.

Deamer, et al., "Characterization of nucleic acids by nanopore analysis", ACC Chem Res, 35(10), 2002, 817-825.

Dressman, "Supplmentary Table to Transforming single DNA molecules into fluorescent magnetic particles for detection and enumeration of genetic variations", PNAS 100, 2003, 8817-8822.

Haugland, "Molecular Probes Handbook", 6th Edition, Eugen, OR, USA, N/A, N/A.

Healy, Ken, "Nanopore-based single-molecule DNA analysis", Nanomed. 2(4), 2007, 459-481.

Lakowicz, J R., "Principles of Fluorescent Spectroscopy, 2nd Edition.", Kluwer Academic/Plenum Publisheers: New York, NY (1999), N/A.

Li, et al., "DNA molecules and configurations in a solid-state nanopore microscope", Nature Mater, 2(9), 2003, 611-615.

Lizardi, "Mutation detection and single-molecule counting using isothermal rolling-circle amplification", Nature Genetics, vol. 19, 1998, 225-232.

Ronaghi, M et al., "A Sequencing Method Based on Real-Time Phyrphosphate", Science. Jul. 17, 1998; 281 (5375):363-365 USE, Jul. 17, 1998, 363-365.

Ronaghi, M et al., "Real-time DNA sequencing using detection of pyrophosphate release", Anal. Biochem. Nov. 1, 1996; 242 (1):84-9, Nov. 1, 1996, 84-89.

Ronaghi, Mostafa, "Pyrosequencing sheds light on DNA sequencing" Genome Res, 11(1), 2001, 3-11.

Soni, et al., "Progress toward Ultrafast DNA Sequencing Using Solid-State Nanopores", Clin Chem, 53(11), 2007, 1996-2001.

* cited by examiner

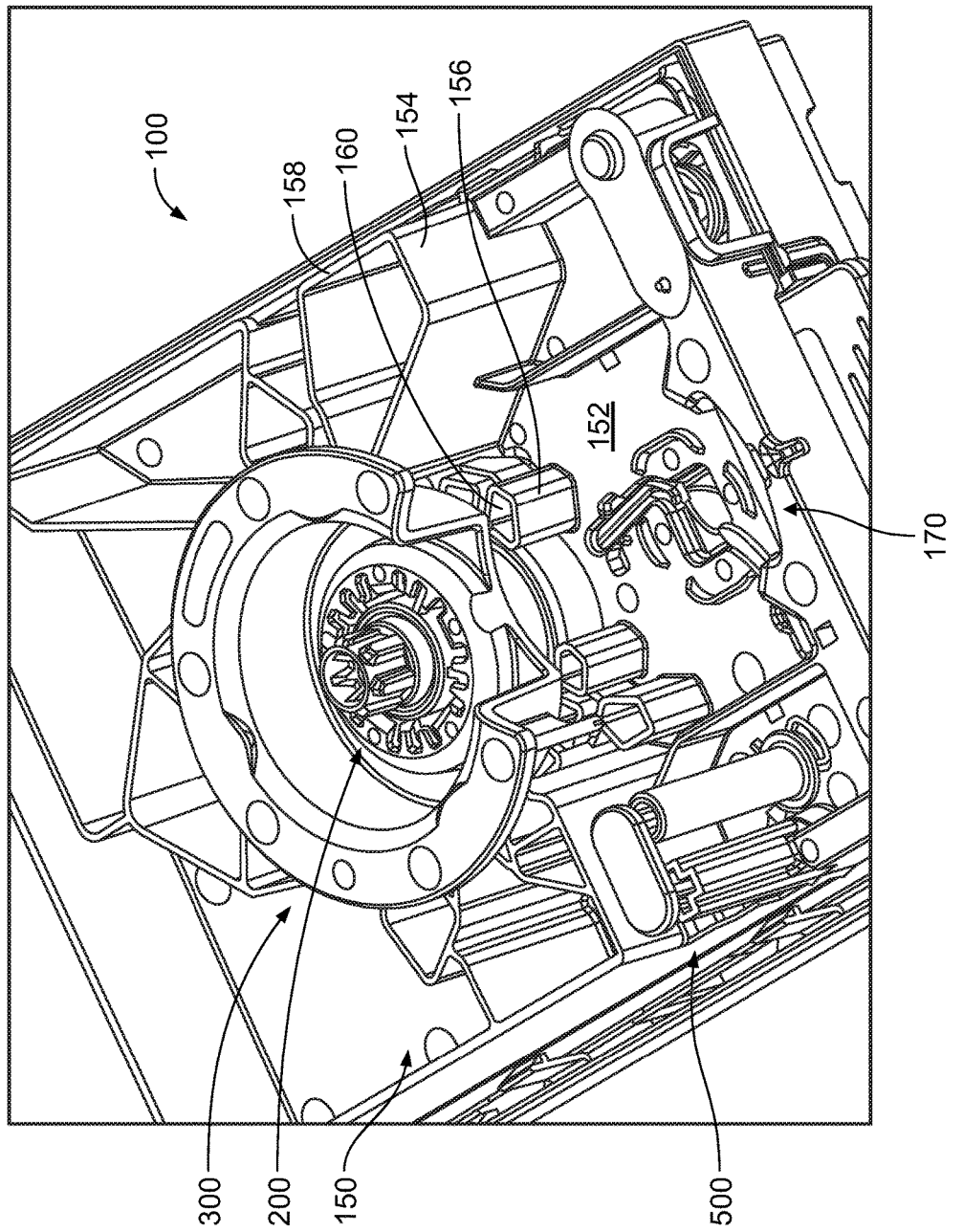

CARTRIDGE ASSEMBLY

RELATED APPLICATIONS

This application claims priority from U.S. Provisional Application Ser. No. 62/408,631, filed Oct. 14, 2016, and Dutch application Serial No. 2017959, filed Dec. 8, 2016; each of the aforementioned applications is hereby incorporated by reference in its entirety.

BACKGROUND

Various protocols used for biological or chemical research include the execution of a large number of controlled reactions. The reactions may be carried out in accordance with a predetermined protocol by automated systems that have, for example, suitable fluidics, optics, and electronics. The systems may be used, for example, to generate a biological or chemical product for subsequent use or to analyze a sample to detect certain properties/characteristics of the sample. When analyzing a sample in some cases, a chemical moiety that includes an identifiable label (e.g., fluorescent label) may be delivered to a chamber where the sample is located and selectively bind to another chemical moiety of the sample. These chemical reactions may be observed or confirmed by exciting the labels with radiation and detecting light emissions from the labels. Such light emissions may also be provided through other means, such as chemiluminescence.

Some known systems use a fluidic device, such as a flowcell, that includes a flow channel (e.g., interior chamber) defined by one or more interior surfaces of the flowcell. The reactions may be carried out along the interior surfaces. The flowcell is typically positioned proximate to an optical assembly that includes a device for imaging the sample within the flow channel. The optical assembly may include an objective lens and/or a solid state imaging device (e.g., CCD or CMOS). In some cases, an objective lens is not used and the solid state imaging device is positioned immediately adjacent to the flowcell for imaging the flow channel.

Before imaging the flow channel, it may be necessary to conduct a number of reactions with the sample. For example, in one sequencing-by-synthesis (SBS) technique, one or more surfaces of the flow channel have arrays of nucleic acid clusters (e.g., clonal amplicons) that are formed through bridge PCR. After generating the clusters, the nucleic acids are "linearized" to provide single stranded DNA (sstDNA). To complete a cycle of sequencing, a number of reaction components are flowed into the flow channel according to a predetermined schedule. For example, each sequencing cycle includes flowing one or more nucleotides (e.g., A, T, G, C) into the flow channel for extending the sstDNA by a single base. A reversible terminator attached to the nucleotides may ensure that only a single nucleotide is incorporated by the sstDNA per cycle. Each nucleotide has a unique fluorescent label that emits a color when excited (e.g., red, green, blue, and the like) that is used to detect the corresponding nucleotide. With the newly-incorporated nucleotides, an image of numerous clusters is taken in four channels (i.e., one for each fluorescent label). After imaging, another reaction component is flowed into the flow channel to chemically cleave the fluorescent label and the reversible terminator from the sstDNA. The sstDNA is then ready for another cycle. Accordingly, a number of different reaction components are provided to the flow channel for each cycle. A single sequencing session may include numerous cycles, such as 100, 300, or more.

The fluids that include the reaction components are typically held in a storage device (e.g., tray or cartridge) in which different fluids are stored in different reservoirs. Due to the number of reaction components and the large number of cycles, the total volume of fluid that is used during one session can be quite large. In fact, for some applications, it is impractical to supply the total volume of reaction components in a single cartridge. For such applications, it may be necessary to use a larger system, multiple systems, or to execute numerous sessions with a single system. These solutions can be costly, inconvenient, or unreasonable in some circumstances.

Definitions

All literature and similar material cited in this application, including, but not limited to, patents, patent applications, articles, books, treatises, and web pages, regardless of the format of such literature and similar materials, are expressly incorporated by reference in their entirety. In the event that one or more of the incorporated literature and similar materials differs from or contradicts this application, including but not limited to defined terms, term usage, described techniques, or the like, this application controls.

As used herein, the following terms have the meanings indicated.

Examples described herein include various systems, methods, assemblies, and apparatuses used to detect desired reactions in a sample for biological or chemical analysis. In some examples, the desired reactions provide optical signals that are detected by an optical assembly. The optical signals may be light emissions from labels or may be transmission light that has been reflected or refracted by the sample. For example, examples may be used to perform or facilitate performing a sequencing protocol in which sstDNA is sequenced in a flow cell. In particular examples, the examples described herein can also perform an amplification protocol to generate a sample-of-interest for sequencing.

Examples herein enable desired reactions to occur where the desired reactions include a change in at least one of a chemical, electrical, physical, and optical property or quality of a substance that is in response to a stimulus. For example, the desired reaction may be a chemical transformation, chemical change, or chemical interaction. In particular examples, the desired reactions are detected by an imaging system. The imaging system may include an optical assembly that directs optical signals to a sensor (e.g., CCD or CMOS). However, in other examples, the imaging system may detect the optical signals directly. For example, a flow cell may be mounted onto a CMOS sensor. However, the desired reactions may also be a change in electrical properties. For example, the desired reaction may be a change in ion concentration within a solution.

Exemplary reactions include, but are not limited to, chemical reactions such as reduction, oxidation, addition, elimination, rearrangement, esterification, amidation, etherification, cyclization, or substitution; binding interactions in which a first chemical binds to a second chemical; dissociation reactions in which two or more chemicals detach from each other; fluorescence; luminescence; chemiluminescence; and biological reactions, such as nucleic acid replication, nucleic acid amplification, nucleic acid hybridization, nucleic acid ligation, phosphorylation, enzymatic catalysis, receptor binding, or ligand binding. The desired reaction can also be addition or elimination of a proton, for example, detectable as a change in pH of a surrounding solution or environment.

Various examples include providing a reaction component to a sample. As used herein, a "reaction component" or "reactant" includes any substance that may be used to obtain a desired reaction. For example, reaction components include reagents, enzymes, samples, other biomolecules, and buffer solutions. The reaction components are typically delivered to a reaction site (e.g., area where the sample is located) in a solution or immobilized within a reaction site. The reaction components may interact directly or indirectly with the substance of interest.

In particular examples, the desired reactions are detected optically through an optical assembly. The optical assembly may include an optical train of optical components that cooperate with one another to direct the optical signals to an imaging device (e.g., CCD, CMOS, or photomultiplier tubes). However, in alternative examples, the sample region may be positioned immediately adjacent to an activity detector that detects the desired reactions without the use of an optical train. The activity detector may be able detect predetermined events, properties, qualities, or characteristics within a predefined volume or area. For example, an activity detector may be able to capture an image of the predefined volume or area. An activity detector may be able detect an ion concentration within a predefined volume of a solution or along a predefined area. Exemplary activity detectors include charged-coupled devices (COD's) (e.g., CCD cameras); photomultiplier tubes (PMT's); molecular characterization devices or detectors, such as those used with nanopores; microcircuit arrangements, such as those described in U.S. Pat. No. 7,595,883, which is incorporated herein by reference in the entirety; and CMOS-fabricated sensors having field effect transistors (FET's), including chemically sensitive field effect transistors (chemFET), ion-sensitive field effect transistors (ISFET), and/or metal oxide semiconductor field effect transistors (MOSFET).

As used herein, the term "illumination element" and "optical components" includes various elements that affect the propagation of optical signals. For example, the optical components may at least one of redirect, filter, shape, magnify, or concentrate the optical signals. The optical signals that may be affected include the optical signals that are upstream from the sample and the optical signals that are downstream from the sample. In a fluorescence-detection system, upstream components include those that direct excitation radiation toward the sample and downstream components include those that direct emission radiation away from the sample. Optical components may be, for example, reflectors, dichroics, beam splitters, collimators, lenses, filters, wedges, prisms, mirrors, detectors, and the like. Optical components also include bandpass filters, optical wedges, and optical devices similar to those described herein.

As used herein, the term "optical signals" or "light signals" includes electromagnetic energy capable of being detected. The term includes light emissions from labeled biological or chemical substances and also includes transmitted light that is refracted or reflected by optical substrates. Optical or light signals, including excitation radiation that is incident upon the sample and light emissions that are provided by the sample, may have one or more spectral patterns. For example, more than one type of label may be excited in an imaging session. In such cases, the different types of labels may be excited by a common excitation light source or may be excited by different excitation light sources at different times or at the same time. Each type of label may emit optical signals having a spectral pattern that is different from the spectral pattern of other labels. For example, the spectral patterns may have different emission spectra. The light emissions may be filtered to separately detect the optical signals from other emission spectra.

The illumination element and/or optical components may have fixed positions in the optical assembly or may be selectively moveable. As used herein, when the term "selectively" is used in conjunction with "moving" and similar terms, the phrase means that the position of the optical component may be changed in a desired manner. At least one of the locations and the orientation of the optical component may be changed. For example, in particular examples, a rotatable mirror is selectively moved to facilitate focusing an optical imaging system.

Analysis operations (also referred to as imaging sessions) include a time period in which at least a portion of the sample is imaged. One sample may undergo or be subject to multiple imaging sessions. For example, one sample may be subject to two different imaging sessions in which each imaging session attempts to detect optical signals from one or more different labels. As a specific example, a first scan along at least a portion of a nucleic acid sample may detect labels associated with nucleotides A and C and a second scan along at least a portion of the sample may detect labels associated with nucleotides G and T. In sequencing examples, separate sessions can occur in separate cycles of a sequencing protocol. Each cycle can include one or more imaging session. In other examples, detecting optical signals in different imaging sessions may include scanning different samples. Different samples may be of the same type (e.g., two microarray chips) or of different types (e.g., a flow cell and a microarray chip).

During an analysis operation, optical signals provided by the sample are observed. Various types of imaging may be used with examples described herein. For example, examples described herein may utilize a "step and shoot" procedure in which regions of a sample area are individually imaged. Examples may also be configured to perform at least one of epi-fluorescent imaging and total-internal-reflectance-fluorescence (TIRF) imaging. In other examples, the sample imager is a scanning time-delay integration (TDI) system. Furthermore, the imaging sessions may include "line scanning" one or more samples such that a linear focal region of light is scanned across the sample(s). Some methods of line scanning are described, for example, in U.S. Pat. No. 7,329,860 and U.S. Pat. Pub. No. 2009/0272914, each of which the complete subject matter is incorporated herein by reference in their entirety. Imaging sessions may also include moving a point focal region of light in a raster pattern across the sample(s). In alternative examples, imaging sessions may include detecting light emissions that are generated, without illumination, and based entirely on emission properties of a label within the sample (e.g., a radioactive or chemiluminescent component in the sample). In alternative examples, flow cells may be mounted onto an imager (e.g., CCD or CMOS) that detects the desired reactions.

As used herein, the term "sample" or "sample-of-interest" includes various materials or substances of interest that undergo an imaging session where optical signals from the material or substance are observed. In particular examples, a sample may include biological or chemical substances of interests and, optionally, an optical substrate or support structure that supports the biological or chemical substances. As such, a sample may or may not include an optical substrate or support structure. As used herein, the term "biological or chemical substances" may include a variety of biological or chemical substances that are suitable for being imaged or examined with the optical systems described herein. For example, biological or chemical substances include biomolecules, such as nucleosides, nucleic acids, polynucleotides, oligonucleotides, proteins, enzymes, polypeptides, antibodies, antigens, ligands, receptors, polysaccharides, carbohydrates, polyphosphates, nanopores, organelles, lipid layers, cells, tissues, organisms, and biologically active chemical compound(s) such as analogs or mimetics of the aforementioned species. Other chemical substances include labels that can be used for identification, examples of which include fluorescent labels and others set forth in further detail below.

Different types of samples may include different optical substrates or support structures that affect incident light in different manners. In particular examples, samples to be detected can be attached to one or more surfaces of a substrate or support structure. For example, flow cells may include one or more flow channels. In flow cells, the flow channels may be separated from the surrounding environment by top and bottom layers of the flow cell. Thus, optical signals to be detected are projected from within the support structure and may transmit through multiple layers of material having different refractive indices. For example, when detecting optical signals from an inner bottom surface of a flow channel and when detecting optical signals from above the flow channel, the optical signals that are desired to be detected may propagate through a fluid having an index of refraction, through one or more layers of the flow cells having different indices of refraction, and through the ambient environment having a different index of refraction.

The systems and methods set forth herein can be used to detect the presence of a particular target molecule in a sample contacted with the microarray. This can be determined, for example, based on binding of a labeled target analyte to a particular probe of the microarray or due to a target-dependent modification of a particular probe to incorporate, remove, or alter a label at the probe location. Any one of several assays can be used to identify or characterize targets using a microarray as described, for example, in U.S. Patent Application Publication Nos. 2003/0108867; 2003/0108900; 2003/0170684; 2003/0207295; or 2005/0181394, each of which is hereby incorporated by reference.

Furthermore, optical systems described herein may be constructed to include various components and assemblies as described in PCT application PCT/US07/07991, entitled "System and Devices for Sequence by Synthesis Analysis", filed Mar. 30, 2007 and/or to include various components and assemblies as described in International Publication No. WO 2009/042862, entitled "Fluorescence Excitation and Detection System and Method", filed Sep. 26, 2008, both of which the complete subject matter are incorporated herein by reference in their entirety. In particular examples, optical systems can include various components and assemblies as described in U.S. Pat. No. 7,329,860 and WO 2009/137435, of which the complete subject matter is incorporated herein by reference in their entirety. Optical systems can also include various components and assemblies as described in U.S. patent application Ser. No. 12/638,770, filed on Dec. 15, 2009, of which the complete subject matter is incorporated herein by reference in its entirety.

In particular examples, methods, and optical systems described herein may be used for sequencing nucleic acids. For example, sequencing-by-synthesis (SBS) protocols are particularly applicable. In SBS, pluralities of fluorescently labeled modified nucleotides are used to sequence a plurality of clusters of amplified DNA (possibly millions of clusters) present on the surface of an optical substrate (e.g., a surface that at least partially defines a channel in a flow cell). The flow cells may contain nucleic acid samples for sequencing where the flow cells are placed within the appropriate flow cell holders. The samples for sequencing can take the form of single nucleic acid molecules that are separated from each other so as to be individually resolvable, amplified populations of nucleic acid molecules in the form of clusters or other features, or beads that are attached to one or more molecules of nucleic acid. Accordingly, sequencing can be carried out on an array such as those set forth previously herein. The nucleic acids can be prepared such that they comprise an oligonucleotide primer adjacent to an unknown target sequence. To initiate the first SBS sequencing cycle, one or more differently labeled nucleotides, and DNA polymerase, etc., can be flowed into/through the flow cell by a fluid flow subsystem (not shown). Either a single type of nucleotide can be added at a time, or the nucleotides used in the sequencing procedure can be specially designed to possess a reversible termination property, thus allowing each cycle of the sequencing reaction to occur simultaneously in the presence of several types of labeled nucleotides (e.g. A, C, T, G). The nucleotides can include detectable label moieties such as fluorophores. Where the four nucleotides are mixed together, the polymerase is able to select the correct base to incorporate and each sequence is extended by a single base. Non-incorporated nucleotides can be washed away by flowing a wash solution through the flow cell. One or more lasers may excite the nucleic acids and induce fluorescence. The fluorescence emitted from the nucleic acids is based upon the fluorophores of the incorporated base, and different fluorophores may emit different wavelengths of emission light. A deblocking reagent can be added to the flow cell to remove reversible terminator groups from the DNA strands that were extended and detected. The deblocking reagent can then be washed away by flowing a wash solution through the flow cell. The flow cell is then ready for a further cycle of sequencing starting with introduction of a labeled nucleotide as set forth above. The fluidic and detection steps can be repeated several times to complete a sequencing run. Exemplary sequencing methods are described, for example, in Bentley et al., Nature 456:53-59 (2008), WO 04/018497; U.S. Pat. No. 7,057,026; WO 91/06678; WO 07/123744; U.S. Pat. Nos. 7,329,492; 7,211,414; 7,315,019; 7,405,281, and US 2008/0108082, each of which is incorporated herein by reference.

In some examples, nucleic acids can be attached to a surface and amplified prior to or during sequencing. For example, amplification can be carried out using bridge amplification to form nucleic acid clusters on a surface. Useful bridge amplification methods are described, for example, in U.S. Pat. No. 5,641,658; U.S. Patent Publ. No. 2002/0055100; U.S. Pat. No. 7,115,400; U.S. Patent Publ. No. 2004/0096853; U.S. Patent Publ. No. 2004/0002090; U.S. Patent Publ. No. 2007/0128624; and U.S. Patent Publ. No. 2008/0009420. Another useful method for amplifying nucleic acids on a surface is rolling circle amplification (RCA), for example, as described in Lizardi et al., Nat. Genet. 19:225-232 (1998) and US 2007/0099208 A1, each of which is incorporated herein by reference. Emulsion PCR on beads can also be used, for example as described in Dressman et al., Proc. Natl. Acad. Sci. USA 100:8817-8822 (2003), WO 05/010145, or U.S. Patent Publ. Nos. 2005/0130173 or 2005/0064460, each of which is incorporated herein by reference in its entirety.

Other sequencing techniques that are applicable for use of the methods and systems set forth herein are pyrosequencing, nanopore sequencing, and sequencing by ligation. Exemplary pyrosequencing techniques and samples that are particularly useful are described in U.S. Pat. Nos. 6,210,891; 6,258,568; 6,274,320 and Ronaghi, Genome Research 11:3-11 (2001), each of which is incorporated herein by reference. Exemplary nanopore techniques and samples that are also useful are described in Deamer et al., Acc. Chem. Res. 35:817-825 (2002); Li et al., Nat. Mater. 2:611-615 (2003); Soni et al., Clin Chem. 53:1996-2001 (2007) Healy et al., Nanomed. 2:459-481 (2007) and Cockroft et al., J. am. Chem. Soc. 130:818-820; and U.S. Pat. No. 7,001,792, each of which is incorporated herein by reference. In particular, these methods utilize repeated steps of reagent delivery. An instrument or method set forth herein can be configured with reservoirs, valves, fluidic lines and other fluidic components along with control systems for those components in order to introduce reagents and detect optical signals according to a desired protocol such as those set forth in the references cited above. Any of a variety of samples can be used in these systems such as substrates having beads generated by emulsion PCR, substrates having zero-mode waveguides, substrates having integrated CMOS detectors, substrates having biological nanopores in lipid bilayers, solid-state substrates having synthetic nanopores, and others known in the art. Such samples are described in the context of various sequencing techniques in the references cited above and further in US 2005/0042648; US 2005/0079510; US 2005/0130173; and WO 05/010145, each of which is incorporated herein by reference.

Exemplary labels that can be detected in accordance with various examples, for example, when present on or within a support structure include, but are not limited to, a chromophore; luminophore; fluorophore; optically encoded nanoparticles; particles encoded with a diffraction-grating; electrochemiluminescent label such as Ru(bpy)32+; or moiety that can be detected based on an optical characteristic. Fluorophores that may be useful include, for example, fluorescent lanthanide complexes, including those of Europium and Terbium, fluorescein, rhodamine, tetramethylrhodamine, eosin, erythrosin, coumarin, methyl-coumarins, pyrene, Malacite green, Cy3, Cy5, stilbene, Lucifer Yellow, Cascade Blue™, Texas Red, alexa dyes, phycoerythin, bodipy, and others known in the art such as those described in Haugland, Molecular Probes Handbook, (Eugene, Oreg.) 6th Edition; The Synthegen catalog (Houston, Tex.), Lakowicz, Principles of Fluorescence Spectroscopy, 2nd Ed., Plenum Press New York (1999), or WO 98/59066, each of which is hereby incorporated by reference. In some examples, the one pair of labels may be excitable by a first excitation wavelength and another pair of labels may be excitable by a second excitation wavelength.

Although examples are exemplified with regard to detection of samples that include biological or chemical substances supported by an optical substrate, it will be understood that other samples can be imaged by the examples described herein. Other exemplary samples include, but are not limited to, biological specimens such as cells or tissues, electronic chips such as those used in computer processors, and the like. Examples of some of the applications include microscopy, satellite scanners, high-resolution reprographics, fluorescent image acquisition, analyzing and sequencing of nucleic acids, DNA sequencing, sequencing-by-synthesis, imaging of microarrays, imaging of holographically encoded micro-particles and the like.

SUMMARY

In accordance with examples herein, a cartridge assembly for use with a fluidics analysis instrument is provided. The cartridge assembly comprises housing, including a flow cell chamber to receive a flow cell, and a well plate having liquid wells to receive desired amounts of liquids. The well plate includes a valve station, a pump station and a fluidics analysis station. The well plate includes channels associated with the wells, the valve station, pump station and fluidics analysis station. A pump assembly is provided on the well plate at the pump station. The pump assembly manages fluid flow through the channels between the pump station and the fluidics analysis station. A rotary valve assembly is positioned on the well plate at the valve station. The rotary valve assembly includes a rotor shaft and rotor valve positioned to rotate about a rotational axis and to selectively couple the wells to the pump station. The rotor shaft has a distal end exposed through the housing. The rotor shaft includes a dual spline configuration at the distal end thereof. The dual spline configuration has first and second sets of splines. The first set of splines forms a drive interface and the second set of splines forms a position encoding interface. The position encoding interface is utilized by the valve drive assembly to track a position of the rotor shaft.

Optionally, the first set of splines represent exterior splines extending about an exterior of the distal end, wherein lateral sides of adjacent splines are separated by a first predetermined spline to spline spacing. The spline to spline spacing corresponds to a spline pattern on a drive shaft of a valve drive assembly. The second set of splines may represent interior splines formed about an interior of a cavity provided at the distal end of the rotor shaft. The interior splines may have lateral sides that are angled such that adjacent lateral sides form a predetermined non-parallel angle with respect to one another. The adjacent lateral sides may merge at a bottom to form pockets to receive mating splines on a drive shaft of the valve drive assembly.

Optionally, the rotor valve may be mounted to a proximal end of the rotor shaft through a coupling flange. The coupling flange may allow a predetermined amount of tilting movement between the rotor valve and rotor shaft. The rotor valve may include a rotor base having one or more ribs positioned about a proximal end of the rotor shaft. The coupling flange may be held between the ribs and the proximal end of the rotor shaft. The rotor valve may include well plate engaging face having a central port and a radial port. The rotor valve may include a channel oriented to extend in a radial direction outward from the central port to the radial port.

Optionally, the central port may be aligned to correspond with a rotational axis of the rotor shaft and align with a central feed port in the well plate. The rotor valve may rotate about the rotational axis to align the radial port with a corresponding well port. The rotary valve may include a well plate engaging face formed with an interface ring thereon. The interface ring may extend about a perimeter of the well plate engaging face. The cartridge assembly may further comprise a valve cap including an interior cavity to rotatably receive the rotary valve. The valve cap may include one or more latch arms to secure the valve cap to the wells and downward against the well plate. A biasing element may be within the interior cavity and may apply a biasing force against the rotary valve to maintain a sealed interface between ports in the rotary valve and ports in the well plate.

Optionally, the pump assembly may include a plunger having a drive end and a biasing surface located at opposite ends of the plunger. The drive end and biasing surface may be exposed at upper and lower surfaces of the housing such that corresponding unidirectional drive and biasing forces are applied thereto in connection with moving the plunger in a reciprocating motion. The plunger may have a drive arm and a plunger arm joined with one another through a bridge segment in a U-shape and may be formed together in a monolithic structure. The drive and plunger arms may be received within support posts located on the well plate. The plunger may comprise a plunger arm and plunger element that are molded together from different materials. The plunger element may be formed on a leading end of the plunger arm. The plunger element may move within the corresponding support post to form high and low pressure states at the pumping station.

Optionally, the pump station may include a channel segment functionally divided into a preparation segment, a discharge segment and a pump work segment, all of which are formed continuous with one another to support fluid flow in either direction. The pump station may include a work area sandwiched between a pair of pinch valves located upstream and downstream of the work area. The pump assembly may comprise a plunger aligned with the work area. The plunger may reciprocally move toward and away from the work area to introduce high and low pressure states. The pump assembly may further comprise push pins aligned with the pinch valves. The push pins may be alternately moved to open and close the pinch valves. A piercer unit may be provided in the housing and positioned proximate to the wells. The piercer unit may include a piercer element. The piercer unit may be moved to a piercing position where the piercer element pierces a cover for the corresponding well.

Optionally, the housing may include a cover having a piercer access opening that provides an instrument access to an upper end of the piercer unit. The piercer unit may include a body that is shaped in a conical tubular manner with a lower platform, an intermediate segment and an upper flange, at least one of the lower platforms or upper flange including piercing elements distributed in a predetermined manner. The piercing elements may be arranged to align with the wells on the well plate. A piercer unit may have a platform that fits over the rotor shaft. The platform may include indexing features that engage mating features on the rotary valve assembly to locate the piercer unit in a predetermined rotational orientation with respect to the rotor shaft in order to align piercer elements with corresponding wells.

Optionally, the well plate may include well transition ports arranged in a predetermined pattern corresponding to the rotary valve assembly. The well plate may include well discharge ports aligned with corresponding wells. The well plate may include well discharge channels extending between corresponding well discharge ports and well transition ports. The well plate may include a base having top and bottom surfaces, at least one of which includes the channels. The channels may include open sided channels. The base may be joined to a backing layer to close the open sided channels. The well plate may include an optical interface window, provided within the optical analysis station. A top side of the well plate may include an insertion limit element to engage an illumination element on an instrument. The insertion limit element may represent one or more ribs that are provided about the optical interface window. The ribs may define a Z-tolerance between an illumination element and the optical interface window.

In accordance with examples herein, a fluidics system is provided comprising a cartridge assembly that has a housing that includes an illumination chamber and a well plate. The well plate is maintained within the housing and has liquid wells to receive desired amounts of liquids. The well plate includes a fluidics analysis station aligned with the illumination chamber. The well plate includes an interface window and interface ports located at the fluidics analysis station. A flow cell cartridge has a frame that contains an analysis circuit therein. The frame includes a flow cell window aligned with the analysis circuit. The frame includes flow cell ports that are fluidly coupled to an active area in the analysis circuit. The housing includes a flow cell chamber to receive the flow cell cartridge. The flow cell chamber to position the flow cell cartridge at the fluidics analysis station with the flow cell window and ports aligned with the corresponding interface window and ports, respectively.

Optionally, the flow cell chamber may include side rails and end stop, at least one of which has an end limit to position the flow cell cartridge, when in a fully loaded position, at a predetermined datum point such that the flow cell window and ports aligned with the corresponding interface window and ports, respectively. The flow cell chamber may include a biasing arm that may be oriented to extend along at least one of the side rails. The biasing arm may extend inward toward the flow cell chamber and to apply a lateral biasing force upon the flow cell cartridge to maintain the flow cell cartridge at the predetermined datum point. The biasing arm may include a latch element positioned to fit with a notch provided in a lateral side of the flow cell cartridge. The latch element may maintain the flow cell cartridge at an X datum point relative to an XYZ coordinate system (as described herein).

Optionally, the flow cell cartridge may include top and bottom frames. The top frame may include the flow cell window and ports. The top frame may include a rib extending upward from the top frame by a predetermined height to define a Z datum point relative to an XYZ coordinate system. The flow cell cartridge may include gaskets formed in a monolithic manner from an elastomer material. The well plate may include a valve station, pump station and interface channels. The interface channels may provide a first fluidic path between the valve station and one of the interface ports and a second fluidic path between the pump station and one of the interface ports. The illumination chamber may be oriented to extend along an illumination axis that may extend through the interface window, flow cell window and the active area within the analysis circuit.

BRIEF DESCRIPTIONS OF THE DRAWINGS

FIG. 1C illustrates a front perspective view of internal components within the cartridge assembly in accordance with an example herein.

DETAILED DESCRIPTION

Cartridge Assembly Overview

Figure 1A:
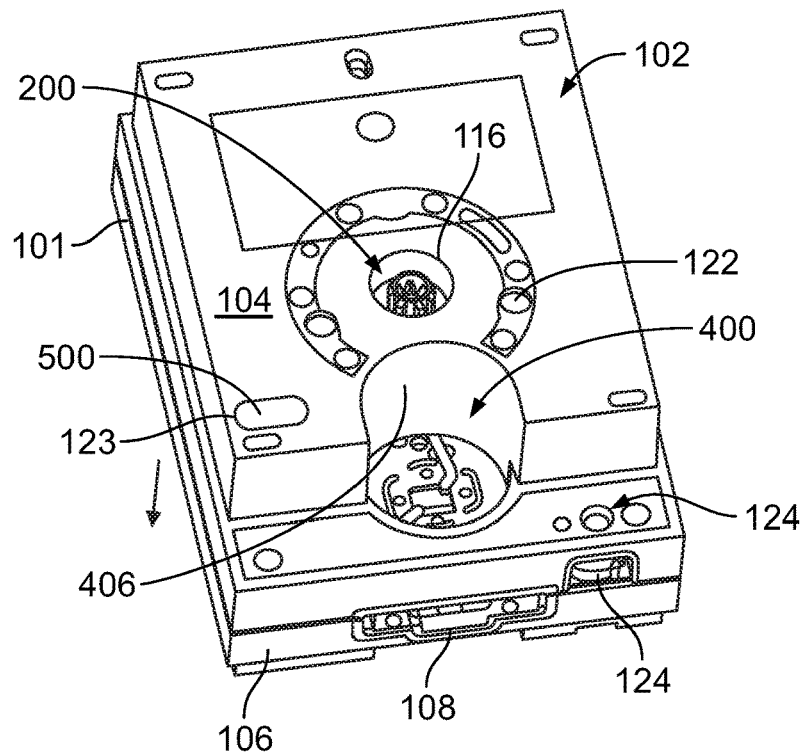
FIG. 1A illustrates a front top perspective view of a cartridge assembly formed in accordance with an example herein.

FIG. 1A illustrates a front top perspective view of a cartridge assembly 100 formed in accordance with an example herein. By way of example the cartridge assembly 100 may represent an SBS cartridge assembly. The cartridge assembly 100 includes a housing to be inserted into a micro-fluidics instrument. While examples herein are described in connection with micro-fluidics systems, instruments and cartridges, optionally examples may be implemented with fluidics systems that may not otherwise be considered "micro" fluidics system, instruments, cartridges, etc. The housing includes a base 101 and a cover 102. The cover 102 includes an instrument engaging surface 104 that includes openings to expose internal components that are engaged by multiple instrument components described below in more detail. During operation, the cartridge assembly 100 is positioned proximate to an instrument that physically, optically and electrically couples to the cartridge assembly 100 in connection with performing a fluidics operation. The cartridge assembly 100 includes a front face 106 that includes a flow cell chamber 108 to receive a flow cell in connection with performing a fluidics operation.

In accordance with examples herein, the cartridge assembly 100 includes various subassemblies including a rotary valve assembly 200 (described below in more detail in connection with FIGS. 2A-2D), a piercer unit 300 (described below in more detail in connection with FIGS. 3A-3D), an illumination chamber 400 (described below in more detail in connection with FIG. 4), and a syringe pump assembly 500 (described below in more detail in connection with FIGS. 6A-6C).

The cover 102 includes a shaft well 116 that exposes a valve shaft within the rotary valve assembly 200. The cover 102 also includes piercer access openings 122 that provide the instrument access to an upper end of the piercer unit 300 in connection with operations described herein. During operation, a drive shaft on the instrument is physically coupled to the valve shaft of the rotary valve assembly 200 to manage movement of the rotary valve assembly 200. The cover 102 includes piercer access openings 122 that provide one or more piercer shafts on the instrument access to an upper end of the piercer unit 300 in connection with a well foil piercing operation. By way of example, multiple piercer access openings 122 may be provided in a distributed manner across an upper end of the piercer unit 300 in order to maintain planar motion of the piercer unit 300 when being activated. A sample well 124 is provided proximate to the front face 106. The sample well 124 is to receive a sample quantity of interest to be analyzed by the instrument. A heating element 125 may be provided proximate to the sample well 124 to adjust the temperature of incoming samples as desired (e.g., to preheat). A pump access opening 123 is provided in the upper surface 104 of the cover 102. The pump access opening 123 is to allow a biasing element within the instrument to engage a spring engaging surface 542 on a plunger of the pump assembly 500. For example, the biasing element may be a metal wave spring, an elastomeric spring, or another structure that provides a uniform force.

Figure 1B:
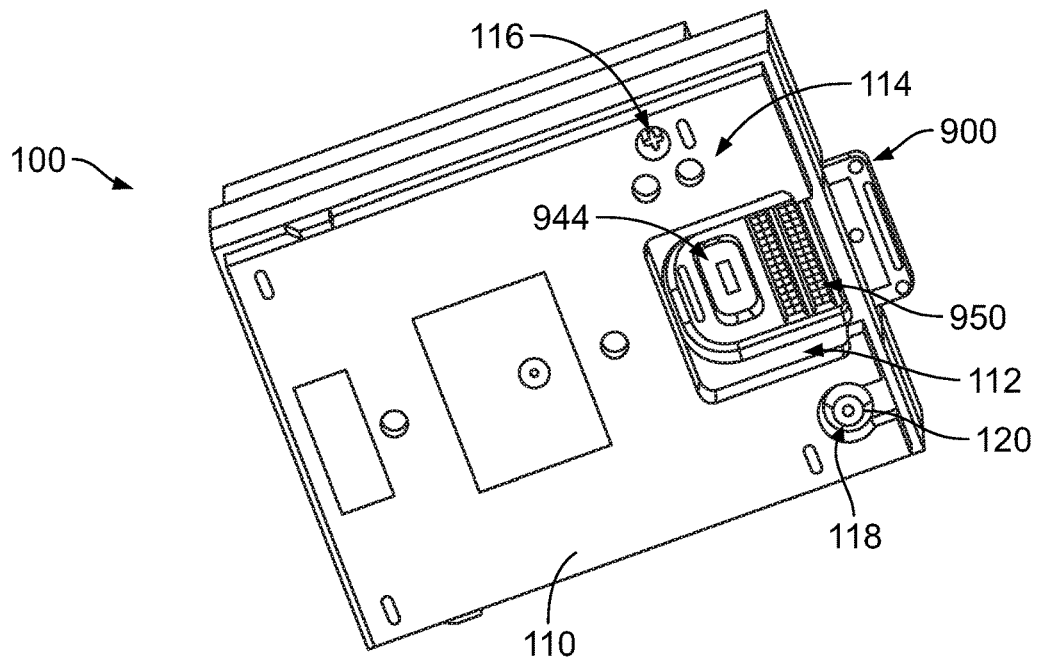
FIG. 1B illustrates a bottom perspective view of the cartridge assembly of FIG. 1A in accordance with an example herein.

FIG. 1B illustrates a bottom perspective view of the cartridge assembly 100 of FIG. 1A. In FIG. 1B, a flow cell cartridge 900 is provided within the flow cell chamber 108. The cartridge assembly 100 includes a bottom surface 110 having a flow cell cartridge access area 112 that exposes portions of interest on the flow cell cartridge 900, such as an array of electrical contact pads 950 and an opening 944 to receive a heater element. The bottom surface 110 also includes a pair of pushpin openings 114 and a pump drive opening 116. The pushpin openings 114 expose pushpins within the pump 500. As explained herein, the pushpins are engaged by valve drive shafts within the instrument to open and close corresponding pinch valves in connection with managing fluid flow. The pump drive opening 116 exposes a proximal end 548 of a valve shaft 546 within the pump 500. As explained herein, the valve shaft 546 is engaged by a pump drive shaft within the instrument to introduce a pumping action in connection with managing fluid flow. The bottom surface 110 also includes an opening 118 to expose a pierceable waste discharge port 120 that is utilized to drain used fluids from a waste container within the cartridge assembly 100.

FIG. 1C illustrates a front perspective view of internal components within the cartridge assembly 100 in accordance with an example herein. As shown in FIG. 1C, the cartridge assembly 100 includes a rotary valve 200 assembly rotatably mounted onto a well plate 150 in a valve operating station. A syringe pump assembly 500 is mounted onto the well plate 150 in a pumping station. The well plate 150 includes a base 152 (e.g., a generally planar later) with multiple reagent wells 154, 156 formed with and extending upward from the base 152. The reagent wells 154, 156 are provided at various positions at least partially surrounding the rotary valve assembly 200. The reagent wells are to receive desired amounts of liquids. Optionally, the wells 154, 156 may include samples and other liquids. As explained herein, the rotary valve assembly 200 selectively couples the reagent wells 154, 156 (generally referred to as liquid wells) to the fluidics analysis station 170.

The reagent wells 154, 156 may be formed with different cross-sectional areas and have different heights extending above the base 152 to define different well volumes to receive a desired quantity of liquid for the corresponding reagent. Optionally, one or more of the wells 154, 156 may be utilized as solution wells in accordance with examples herein. The wells 154, 156 include filling ends 158, 160 that are open to receive a desired amount of liquid during a filling operation. Once the desired amount of liquid is added to the wells 154, 156, the filling ends 158, 160 are covered with a foil or other sealing cover to form an airtight volume within each of the wells 154, 156. While not visible in FIG. 1C, the wells 154, 156 include one or more discharge ports provided in the bottom thereof. During operation, the cover is pierced to allow air to enter one or more of the well volumes, thereby permitting the liquid to freely flow (e.g. through gravity or under pressure) through the discharge ports to the fluidics analysis station 170 under control of the rotary valve 200 and pump assembly 500.

Figure 1D:
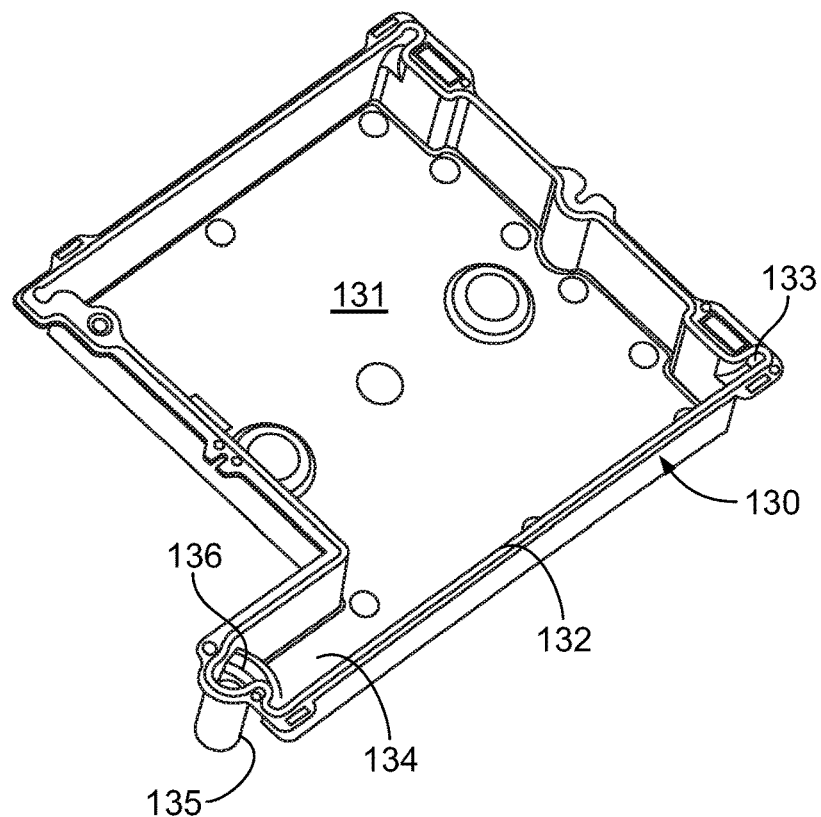
FIG. 1D illustrates a top perspective view of a waste tray that is mounted below the well plate and forms part of the housing of the cartridge assembly in accordance with examples herein.

FIG. 1D illustrates a top perspective view of a waste tray 130 that is mounted below the well plate 150 and forms part of the housing of the cartridge assembly 100. The waste tray includes a waste collection volume 131 that spans an area below a relatively large portion of the well plate 150. By way of example, the waste tray 130 is located below the rotary valve assembly 200 and at least a portion of the wells 154, 156. The waste tray 130 includes a ridge 132 that extends about a perimeter thereof and is sealed to a mating surface (e.g. on the bottom surface of the well plate 150). The ridge 132 may include vents 133 in the corners thereof that communicate with openings through the well plate 150. The vents 133 permit air to discharge from the volume 131 as waste liquids enter the volume 131. The vents 133 are positioned above the area in which the liquid is retained to prevent leakage. The vents 133 are distributed to allow the cartridge assembly 100 to be slightly tilted during operation such that at least one of the vents 133 will always be usable as an air inlet. The vents 133 allow the size of the waste tray 130 to be limited as waste liquids are permitted to slosh up to the surface of the vents 133 without leaking. The vents 133 may be formed of a porous material, such as expanded poly propylene, polyethylene or polytetrafluoroethylene.

The waste tray 130 also includes a funnel region 134 and a discharge tube 135. The funnel region 134 terminates at a ledge area 136 that communicates with an opening to the tube 135. The bottom end of the tube 135 is initially closed with a cover. To empty the waste tray 130, the cover 136 may be pierced and the cartridge assembly 100 (including the waste tray 130) tilted with the funnel region 134 at the lowest point therein. The waste liquids flow through the funnel region 134 over the ledge area 136 and out of the tube 135.

Flow Cell Chamber

Figure 1E:
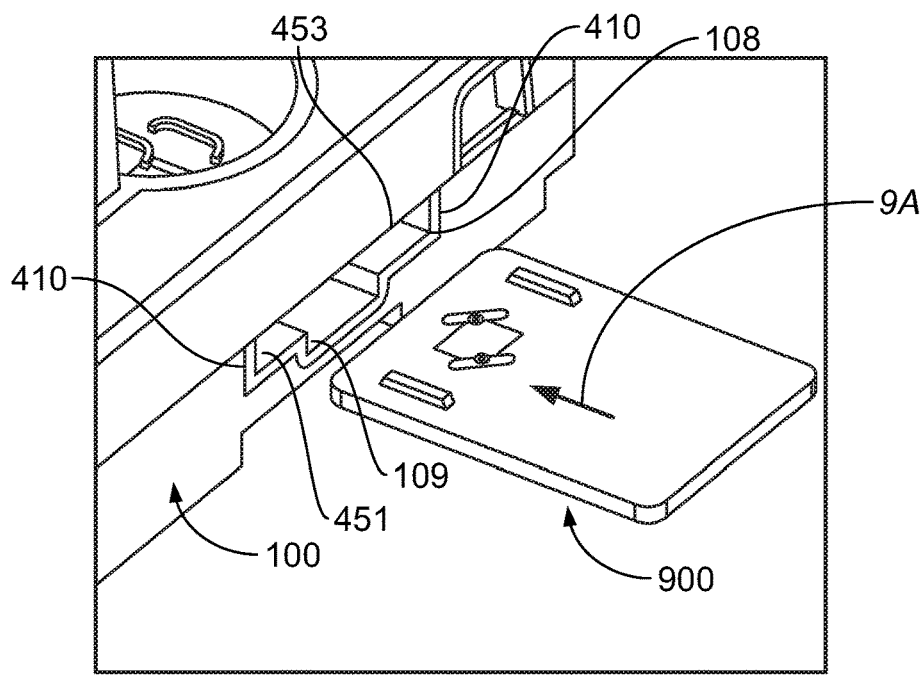
FIG. 1E illustrates a front perspective view of a portion of the cartridge assembly and a flow cell cartridge align with the flow cell chamber in accordance with examples herein.

FIG. 1E illustrates a front perspective view of a portion of the cartridge assembly 100 and a flow cell cartridge 900 align with the flow cell chamber 108. The flow cell chamber 108 includes a key feature 109 which may be shaped as a channel and provided in the bottom surface of the flow cell chamber 108. The key feature 109 is shaped and dimensioned to receive a corresponding keying feature (e.g. stand-off 914 FIG. 9C) on a bottom of the flow cell cartridge 900 to ensure that the flow cell cartridge 900 is loaded in the correct direction and orientation. The flow cell chamber 108 includes side rails 413 and upper and lower walls 451 and 453. The cartridge 900 is inserted in a loading direction 9A.

Figure 1F:
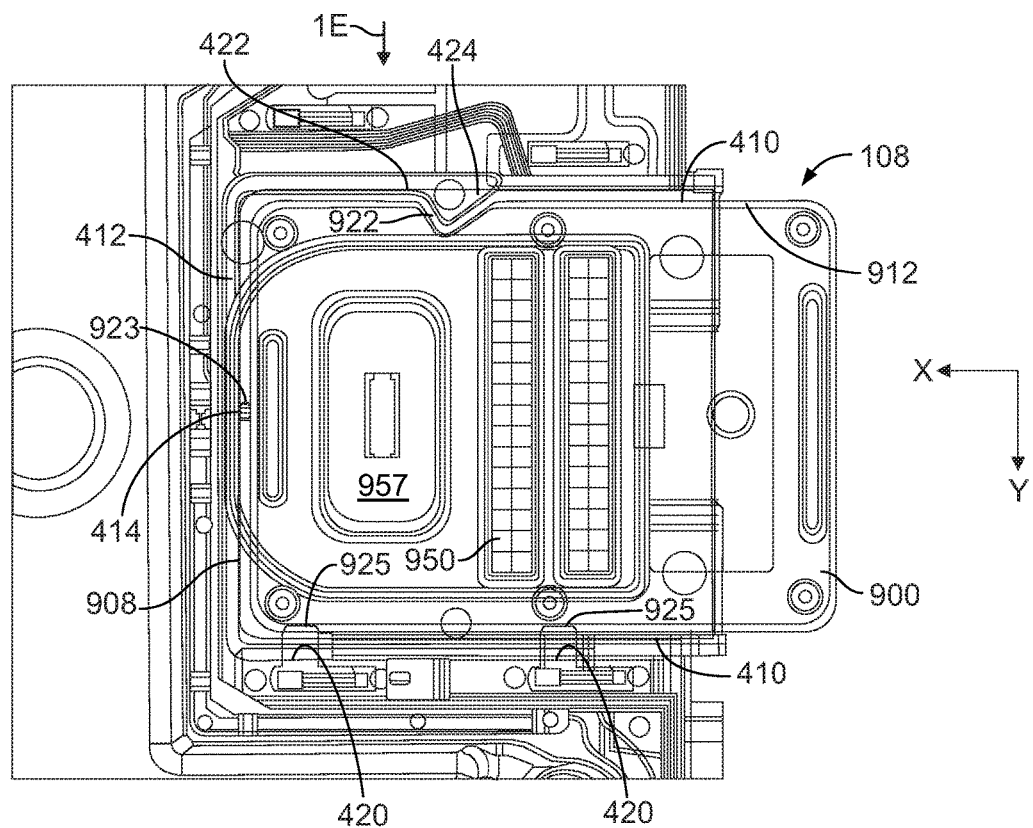
FIG. 1F illustrates a bottom plan view of the flow cell chamber with a flow cell cartridge inserted therein in accordance with an example herein.

FIG. 1F illustrates a bottom plan view of the flow cell chamber 108 with a flow cell cartridge 900 inserted therein in accordance with an example herein. The flow cell cartridge 900 is inserted into the flow cell chamber 108 to a fully loaded position in FIG. 1F. As described herein, in more detail in connection with FIGS. 9A-9E, the flow cell cartridge 900 includes a loading end 908 and lateral edges 912. The loading end 908 includes a reference post 923, while at least one of the lateral edges 912 includes one or more lateral reference posts 925. An opposite lateral edge 912 includes a notch 927. A bottom side of the flow cell cartridge 900 includes openings to expose a heat spreader 957 and contact pads 950.

The flow cell chamber 108 includes top and bottom surfaces, and lateral side rails 413 that extend parallel to one another along opposite lateral sides of the chamber 108. An end stop 417 is provided at an innermost depth of the chamber 108. The top and bottom surfaces, lateral side rails 413, and end stop 417 are positioned to orient the flow cell cartridge 900 at predetermined datum points (e.g., reference points referred to as an X datum point, Y datum point and Z datum point) relative to a coordinate system (e.g., XYZ coordinate system). The end stop 417 includes an end limiter 414 provided at a desired position along the end stop 417. The end limiter 414 aligns with a reference post 923 provided on the loading end 908. One of the side rails 413 includes lateral limits 420 that extend inward towards the flow cell chamber 108. The lateral limits 420 align with the lateral reference post 923. The opposite side rail 413 includes a biasing arm 422 that is oriented to extend along the side rail 413 and to apply a lateral biasing force in the direction of arrow 1E. The biasing arm 422 includes a latch element 424 on a distal end thereof. The latch element 424 is shaped to fit in the notch 927 in the side edge 912.

During a loading operation, the loading end 908 is inserted into the flow cell chamber 108 until the reference post 923 firmly abuts against a limit feature in the flow cell chamber 108 to define a limit of movement in the loading direction 9A. As flow cell cartridge 900 is inserted, the biasing arm 422 rides along the side edge 912 that includes the notch 927 until the latch element 424 fits within the notch 927. The biasing arm 422 applies a lateral force in the direction of arrow 1E (also represents a lateral positioning force) to shift the flow cell cartridge 900 in the lateral direction (corresponding to the Y-axis) until the lateral reference posts 923 engage the lateral limits 420. The lateral limits of the flow cell chamber 108 define a limit of movement in the lateral Y-direction. The biasing arm maintains the flow cell cartridge 900 at the desired Y-position (corresponding to a Y datum point). The latch element 424 within the notch 927 at a predefined position to maintain the flow cell cartridge 900 at the desired X-position (corresponding to an X datum point).

The flow cell chamber 108 enables a snap-in arrangement for the flow cell cartridge 900. By enabling the flow cell cartridge 900 to be inserted into and removed from the cartridge assembly 100, examples herein allow the flow cell cartridge to be managed and shipped separately from the reagents and samples. In addition, by separating the flow cell cartridge 900 from the reagents, examples herein allow separate manufacturing workflows. In addition, examples herein allow flow cell cartridges to be mixed and matched with various combinations of reagents, reagent volumes and flow cell cartridge sizes. For example, one protocol may utilize larger volumes of certain reagents, while another protocol utilizes a greater number of different reagents, but in smaller volumes. The various criteria for the number and volume of reagents may be satisfied by different cartridge assemblies, while any of the foregoing cartridge assemblies are able to utilize the same flow cell cartridge. As a further example, the same type of cartridge assembly may be utilized with different protocols that have different requirements within the analysis circuit. For example, one protocol may utilize an analysis circuit that has a large optical footprint, while another protocol may utilize an analysis circuit that has a smaller optical footprint. In addition, some protocols may utilize analysis circuits that have more complex electronics and interconnections, as compared to other analysis circuits, while any of the foregoing analysis circuits may be embodied within a flow cell cartridge having a common overall envelope that fits into the same cartridge assembly.

Examples described herein provide an interface having a small height (e.g. a minimized height) between the analysis circuit and the light source within the illumination element of the instrument.

Piercer Unit

Figure 3A:
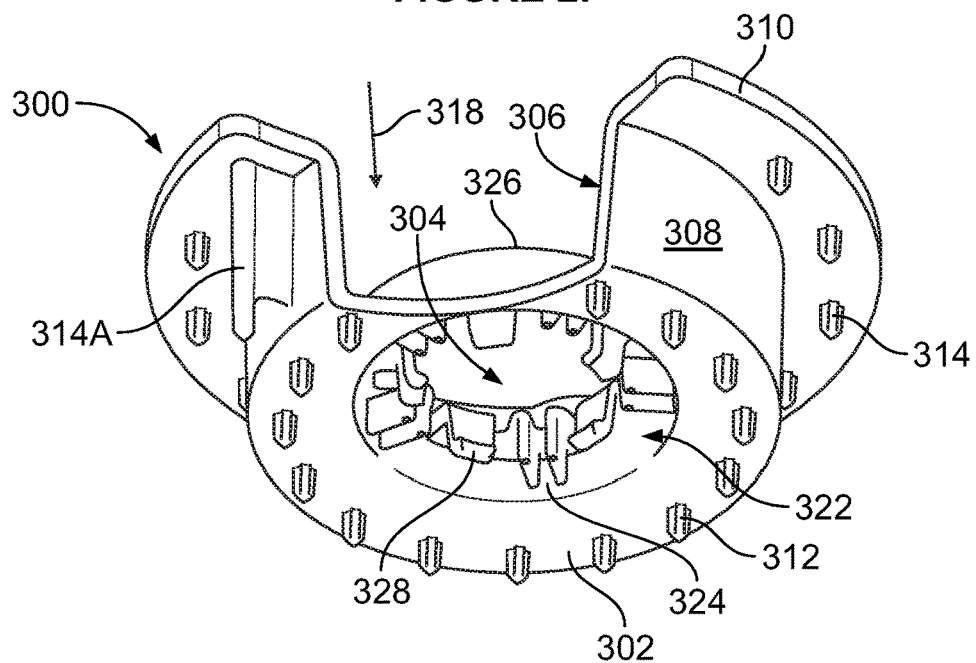
FIG. 3A illustrates a bottom perspective view of the piercer unit formed in accordance with an example herein

A piercer unit 300 is provided in the housing and positioned proximate to the wells 154, 156. The piercer unit 300 is moved to a piercing position where piercer elements pierce a foil or cover for the corresponding well(s) 154, 156. In the example of FIG. 3A, the piercer unit 300 is mounted on the rotary valve assembly 200 and is managed during operation by the instrument to pierce one or more of the wells 154, 156.

FIG. 3A illustrates a bottom perspective view of the piercer unit 300 is formed in accordance with an example herein. The piercer unit 300 is illustrated with a partial cut out to better present the overall structure therein. The piercer unit 300 includes a body 306 that is shaped in a conical tubular manner with a lower platform 302, an intermediate segment 308 and an upper flange 310. The platform 302, segment 308, and flange 310 are formed in a monolithic manner. The lower platform 302 includes a plurality of piercing elements 312 distributed in a predetermined manner about the platform 302. In the example of FIG. 3A, the piercing elements 312 are arranged in a circular pattern. The upper flange 310 also includes piercing elements 314 provided on a lower surface thereof and projecting in a common direction as the piercing elements 312. The piercing elements 314 are distributed about the upper flange 310 in a predetermined manner, such as in a circular pattern.

During operation, the piercing unit 300 is activated by a piercer actuator assembly on the instrument. For example, with reference to FIG. 1A, the instrument may extend one or more piercer shafts through the piercer access ports 122 in the cover 102. The piercer shafts push downward in a piercing direction 318 to force the piercing unit 300 downward, thereby driving the piercing elements 312, 314 through the foil/cover on the corresponding wells 154, 156. The piercer shafts are distributed to evenly apply the piercing force to the piercer unit 300.

In accordance with at least one example, the piercing elements 312, 314 are formed with an X-shaped cross-section to facilitate piercing the foil/cover and to provide venting through the foil/cover. The X-shaped cross-section allows air to enter the corresponding well volume even while the piercing elements 312, 314 extend through the foil/covers.

In the example of FIG. 3A, a majority the piercing elements 312, 314 have a generally common length. However, optionally various ones of the piercing elements 312, 314 may be longer or shorter, such as shown by piercing element 314A. With joint reference to FIGS. 10 and 3A, the piercing elements 312, 314 are positioned to align with corresponding wells 154, 156. In the example of FIGS. 10 and 3A, the piercing elements 312, 314 generally have a common length to pierce each of the corresponding wells 154, 156 at the same time when the piercing element 300 is activated. Optionally, the piercing unit 300 may be operated (by the piercer actuator assembly) as a multistage piercing system such that only a portion of the piercing elements 312, 314 pierce corresponding wells 154, 156 during a first piercing operation, while a different portion of the piercing elements 312, 314 pierce corresponding wells 154, 156 during a second piercing operation. For example, the piercing elements 312 may be formed longer than the piercing elements 314 such that the piercing elements 312 pierce corresponding foils during the first piercing operation, and the piercing elements 314 pierce corresponding foils during the second piercing operation.

The lower platform 302 includes an internal rim 326 that is formed about the opening 304. The rim 326 includes multiple indexing features 322 provided about the opening 304. The indexing features 322 engage mating features on the rotary valve assembly 200 in order to locate the piercer unit 300 in a predetermined rotational orientation with respect to the rotor shaft 202 in order to align the piercer elements 312, 314 with corresponding wells 154, 156. The indexing features 322 include one or more notches 324 which are provided about the internal rim 326. The rim 326 projects slightly upward into an interior portion of the body 306 toward the upper flange 310. The notches 324 are distributed in a predetermined pattern about the opening 304. The notches 324 align with ribs or teeth that are provided on the rotary valve assembly 200 (as described below in more detail). In the example of FIG. 3A, notches 324 are relatively evenly positioned about the perimeter of the opening 304. Additionally or alternatively, more or fewer notches 324 may be utilized and may be positioned in alternative locations in an even or uneven distribution. Optionally, an indexing feature other than notches 324 may be utilized.

The rim 326 also includes one or more flexible standoff 328 that extend downward into the opening 304 in a direction common with the piercing elements 312. The standoffs 328 engage a ledge 216A extending about a perimeter of the base extension 216. Once the notches 324 align with corresponding teeth on the rotary valve assembly 200, the piercer unit 300 is loaded until the standoffs 328 rest on a top surface of the ledge 216A. The standoffs 328 remain on the ledge 216A to maintain the piercing unit 300 positioned vertically in a non-piercing/ready position. During operation, the piercer unit 300 is forced downward (in the direction of arrow 318) by a piercer shaft, in response to which the standoffs 328 flex outward and ride down over the ledge 216A to permit the piercer unit 300 to slide downward in the piercing direction 318 further onto the rotor cap 210.

Figure 3B:
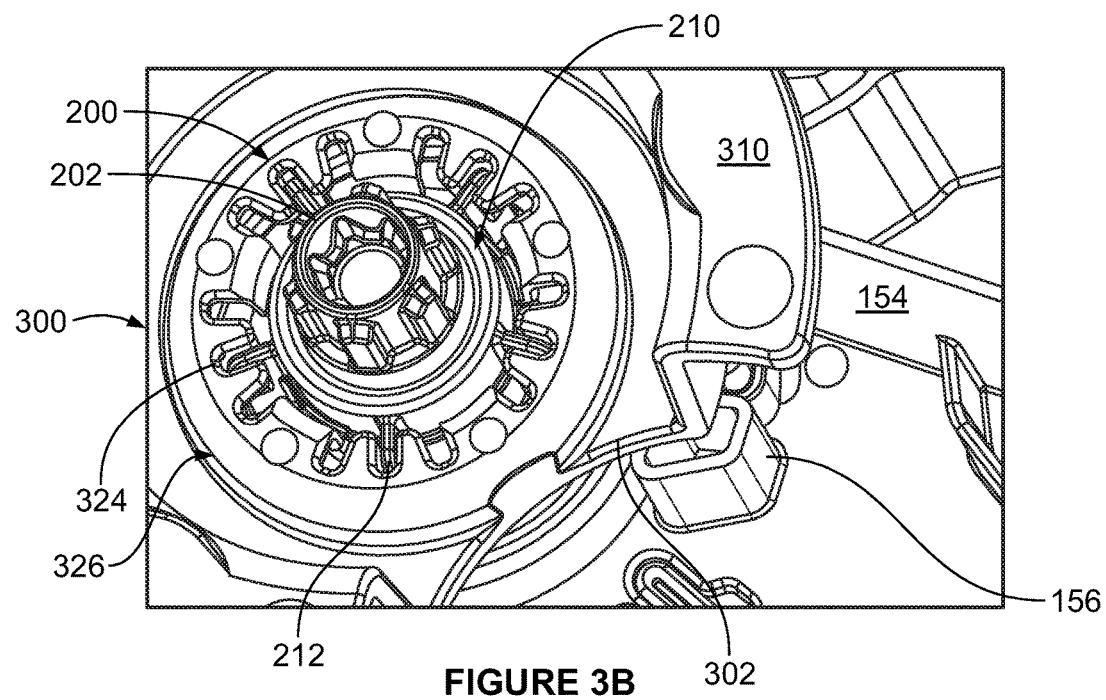
FIG. 3B illustrates a top view of a portion of the piercing unit when installed on the rotary valve assembly in accordance with an example herein.

FIG. 3B illustrates a top view of a portion of the piercing unit 300 when installed on the rotary valve assembly 200. As explained herein, the rotary valve assembly 200 includes a rotor shaft 202 with a valve cap 210 mounted over the rotor shaft 202. The valve cap 210 includes a plurality of teeth 212 distributed peripherally about a central rim of the valve cap 210. The teeth 212 align with, and are received in, the notches 324 on the piercer unit 300 in order to rotationally position the piercing unit 300 in a predetermined rotational angle relative to the rotary valve assembly 200. While not shown, the latches 328 (FIG. 3A) are securely joined with latching features on the valve cap 210 to maintain the piercing unit 300 in a mounted position along a rotational axis extending along a central axis of the rotor shaft 202 of the rotary valve assembly 200.

Figure 3C:
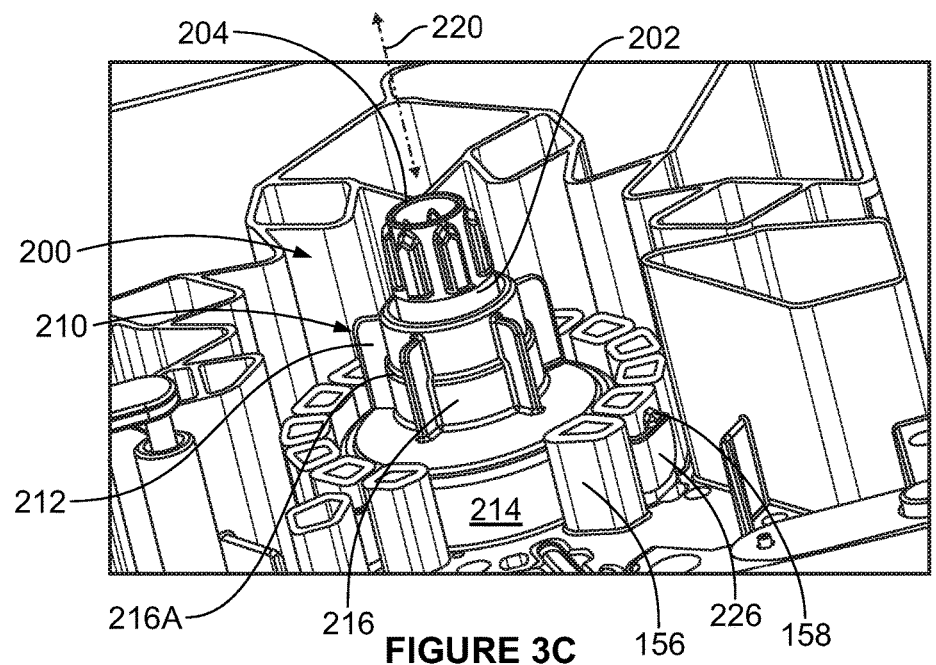
FIG. 3C illustrates the rotary valve assembly with the piercing unit removed to better illustrate the valve shaft in accordance with an example herein.

FIG. 3C illustrates the rotary valve assembly 200 with the piercing unit 300 removed to better illustrate the rotor shaft 202. The rotor shaft 202 is elongated and rotates about a rotational axis 220. The rotor shaft 202 includes a proximal end (not visible in FIG. 3C) and a distal end 204. The valve cap 210 is loaded over the distal end 204 of the rotor shaft 202 to an installed position as shown in FIG. 3C. The valve cap 210 includes a cap base 214 that has an enlarged diameter that is dimensioned to fit within a collection of wells 156 that are arranged adjacent one another in a generally circular manner. The cap base 214 is joined with a cap extension 216 that extends upward from the cap base 214 along a length of the rotor shaft 202. The cap extension 216 has a smaller diameter than the diameter of the cap base 214 in the example of FIG. 3C. However, it is recognized that alternative dimensions may be utilized for the cap extension 216 and cap base 214. The cap extension 216 includes teeth 212 formed upon a periphery of the cap extension 216 and projects outward radially (relative to the rotational axis 220) therefrom.

The cap base 214 includes one or more latch arms 226 that extend radially outward from the cap base 214. The latch arms 226 are formed in an L-shape and dimensioned such that a leg of the latch arm 226 fits between adjacent wells 156, while an outer portion or foot on the latch arm 226 bends about and rests securely against an outer surface of one of the wells 156. The corresponding well 156 includes a detent 158 provided on an outer wall of the well 156. The L-shaped latch arm 226 snaps over and is held securely below the detent 158 when the valve cap 210 is inserted over the rotor shaft 202.

Rotary Valve Assembly

Next, the operation of the rotary valve assembly 200 will be described in connection with FIGS. 2A-2F.

Figure 2A:
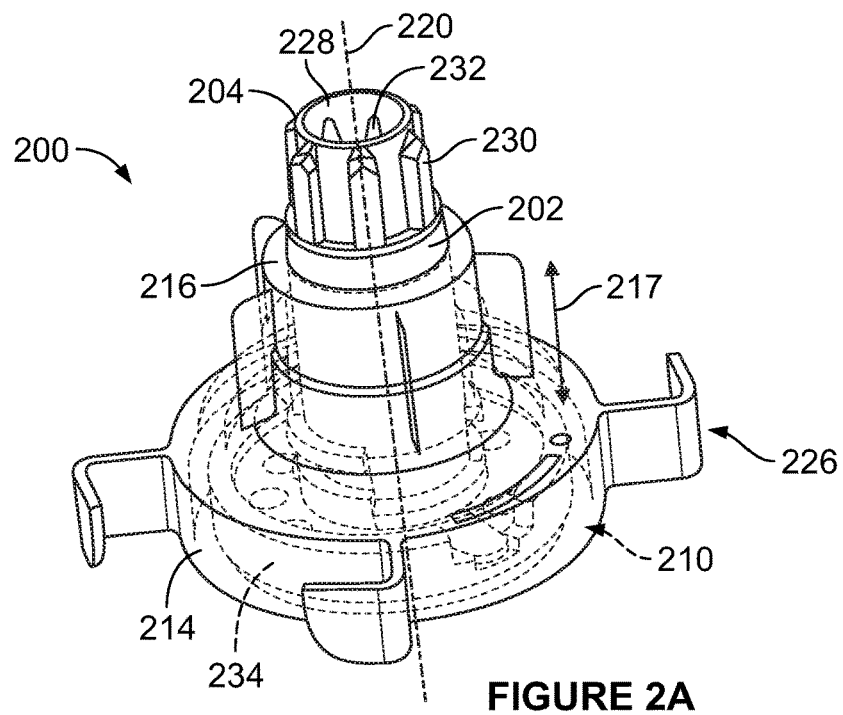
FIG. 2A illustrates a perspective view of a rotary valve assembly formed in accordance with an example herein.

FIG. 2A illustrates a perspective view of a rotary valve assembly 200 formed in accordance with an example herein. FIG. 2A better illustrates the valve cap 210 provided over the rotor shaft 202. The rotor shaft 202 rotates within the valve cap 210, with the valve cap 210 maintaining the rotor shaft 202 at a predetermined position with respect to the well plate 150. The valve cap 210 includes multiple latch arms 226 distributed evenly about a perimeter of the cap base 214. A distal end 204 of the rotor shaft 202 projects beyond the cap extension 216. The distal end 204 includes a plurality of exterior splines 230 distributed about the rotor shaft 202. The distal end 204 also includes a cavity 228 that includes interior splines 232 distributed about the cavity 228. The rotor shaft 202 includes a dual spline configuration having the interior and exterior splines 232, 230 (also referred to as first and second sets of splines) that mate with a matching spline configuration on a drive shaft of a valve drive assembly within the instrument that engages the cartridge assembly during a fluidics operation. The dual spline configuration of interior and exterior splines 232, 230 provides a drive interface and a position encoding interface to precisely track a rotational relation between the drive shaft of the instrument and the rotor shaft 202.

The valve cap 210 is illustrated in a partially transparent manner to show a rotor valve 234 below the valve cap 210 and mounted about a proximal end of the rotor shaft 202. The rotor valve 234 is secured to the rotor shaft 202 and rotates with the rotor shaft 202. The rotor valve 234 rotates within (and relative to) the cap base 214, while the cap base 214 remains stationary with the latch arms 226 secured about corresponding wells on the well plate 150. An inner diameter of the cap extension 216 corresponds to an outer diameter of the rotor shaft 202 to provide a close tolerance there between. The cap extension 216 has a length 217 that may be varied, provided that the cap extension 216 affords sufficient structural and rotational support to the rotor shaft 202, whereby the rotational axis of the rotor shaft 202 is maintained at a predetermined fixed point relative to the well plate 150. By way of example, the rotational axis of the rotor shaft 202 may correspond with a central port provided in the well plate through which fluids travel. As explained herein, the valve drive assembly of the instrument rotates the rotor shaft 202, which in turn rotates the rotary valve 234 in order to fluidly couple a desired one of the wells 154, 156 with the central port below the rotor shaft 202.

Figure 2B:
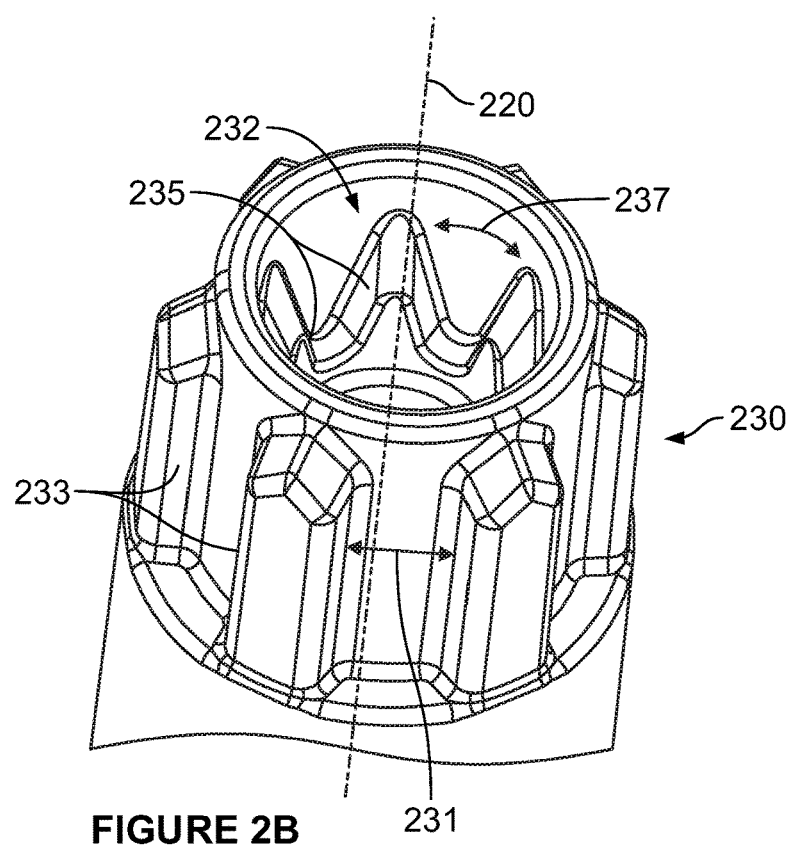
FIG. 2B illustrates an enlarged perspective view of the distal end of the rotor shaft in accordance with examples herein.

FIG. 2B illustrates an enlarged perspective view of the distal end 204 of the rotor shaft 202. The interior and exterior splines 232, 230 have different spline shapes. The exterior splines 230 represent a first set of splines that form a drive interface, such that the first/exterior splines are engaged by mating splines of a driveshaft of a valve drive assembly. The interior splines 232 represent a second set of splines that form a position encoding interface that is utilized by the valve drive assembly to maintain a fully mated (and closely tracked) interconnection between the driveshaft of the valve drive assembly and the rotor shaft 202. The exterior splines 230 have spline lateral sides 233 that extend substantially parallel to one another. The exterior splines 230 are oriented to extend substantially parallel to one another with lateral sides 233 of adjacent splines separated by a first predetermined spline to spline spacing 231. The spline to spline spacing 231 corresponds to a spline pattern on a drive shaft of a valve drive assembly. The spline displaying spacing 231 is defined to be slightly larger than the mating splines from the shaft drive assembly in order to facilitate engagement. By providing the spline to spline spacing 231 larger than the incoming splines, a slight amount of slack is introduced that may otherwise permit a limited amount of relative rotational shift between the rotor shaft and the driveshaft. Accordingly, the splines of the driveshaft may not be an exact indicator of the rotational position of the rotor shaft 230. Instead, the interior splines 232 form a position encoding interface that is utilized to provide position encoding information when joined with a separate position encoding/tracking element of the drive assembly as explained herein. The position encoding interface is utilized by the valve drive assembly to closely and precisely track a position of the rotor shaft independent of the drive splines the join the exterior splines 230. The interior splines 232 have lateral sides 235 that extend in a V-shape such that adjacent lateral sides form a predetermined non-parallel angle 237 with respect to one another (e.g., a 30 degree angle). The lateral sides 235 merge at the bottom of the interior splines 232 to form V-shaped pockets that receive mating splines on the drive shaft of the valve drive assembly. The splines 232 fully engage the mating splines on the drive shaft and cooperate to avoid backlash. The splines 232 also allow the drive shaft to operate at a somewhat "skewed" orientation or angle to the rotor shaft 202. The splines 230, 232 and distal edge of the distal end may be configured with beveled edges to facilitate alignment of the drive shaft and avoid the drive shaft from merely butting against a distal end of the rotor shaft 202 without the splines aligning.

The dual spline configuration of FIG. 2B utilizes the exterior splines 230 to be relatively "loosely" engaged and driven by splines of the valve drive assembly, while utilizing the interior splines 232 to be relatively "closely" engaged by a position encoder that monitors the rotational position of the rotor shaft 202.

Figure 2C:
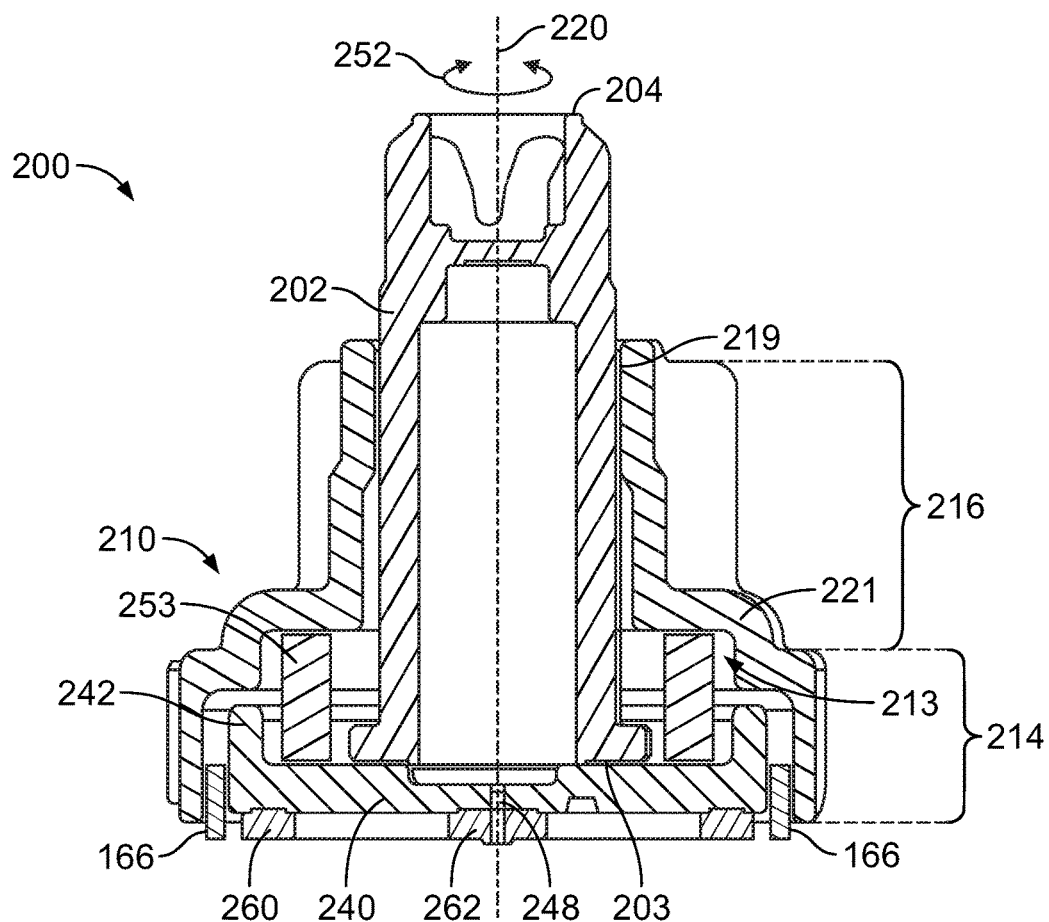
FIG. 2C illustrates a side sectional view of the rotary valve assembly which includes the valve shaft in accordance with examples herein.

FIG. 2C illustrates a side sectional view of the rotary valve assembly 200 which includes the rotor shaft 202, valve cap 210, and rotary valve 234. FIG. 2B illustrates proximal and distal ends 203, 204 of the rotor shaft 202. The rotor shaft 202 is elongated and held in position by the valve cap 210 to rotate about the rotational axis 220. FIG. 2B illustrates a cross-sectional envelope of the valve cap 210 which illustrates the cap base 214 to have a greater diameter than the cap extension 216. The cap extension 216 includes an interior passage 219 having an inner diameter that substantially corresponds to the outer diameter of the rotor shaft 202. The interior passage 219 of the cap extension 216 holds the rotor shaft 202 in a predetermined orientation with the rotational axis 220 centered at a desired point on the well plate (e.g., corresponding to a central feed port).

Figure 2D:
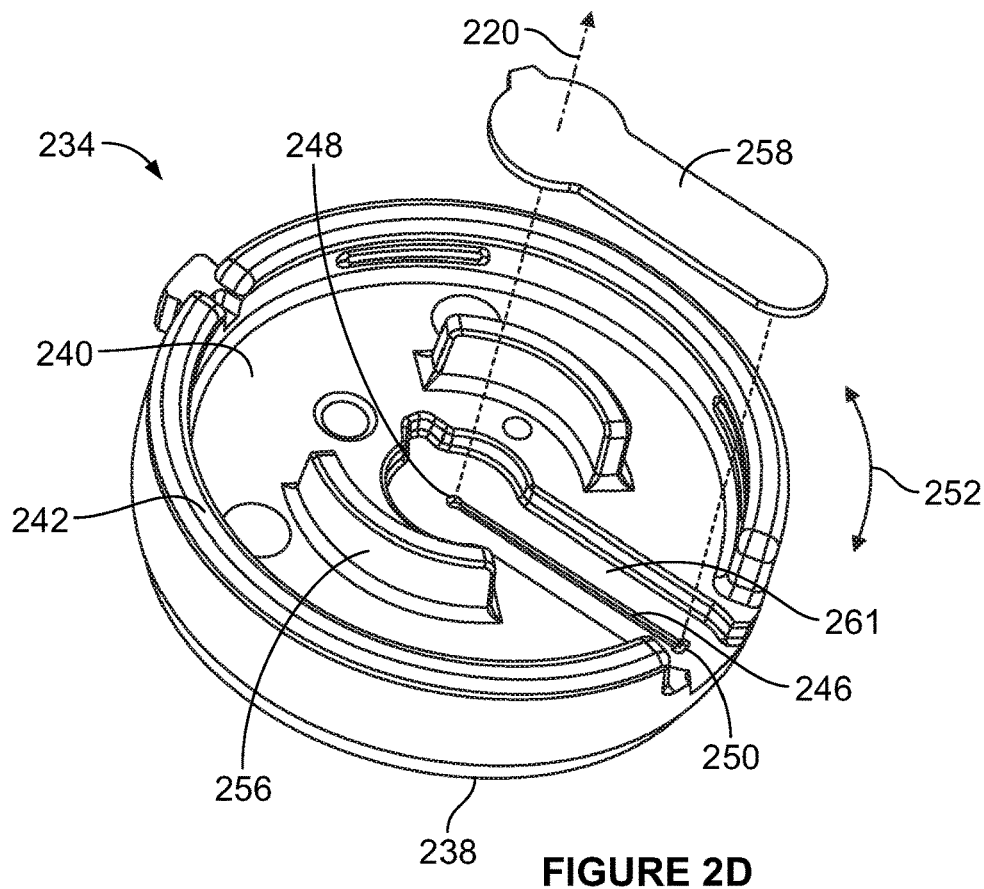
FIG. 2D illustrates a top perspective view of the rotor valve formed in accordance with an example herein.

FIG. 2D illustrates a top perspective view of the rotor valve 234 formed in accordance with an example herein. The rotor valve 234 includes a rotor base 240 having an upper surface and a well plate engaging face 238. The rotor base 240 may be injection molded with polypropylene or another material with desired properties. A fluid channel 246 is provided within the rotor base 240. The fluid channel 246 is oriented to extend in a radial direction outward from a central point of the rotor base 240, corresponding to a central port 248. The fluid channel 246 extends to a peripheral point on the rotor base 240 and terminates at a radial port 250. The central and radial ports 248, 250 extend through the rotor base 240 to open onto a well plate engaging face 238. The central port 248 may be aligned to correspond with the rotational axis 220 of the rotor shaft 202 and aligned with a central feed port in the well plate 150. The rotor valve 234 is rotated about the rotational axis 220 in either radial direction 252 to align the radial port 250 with a corresponding well transition port 162 in connection with pulling a reagent or sample of interest from a well.

The upper surface of the rotor base 240 includes a recessed cavity 261 surrounding the fluid channel 246. The recessed cavity 261 is shaped to receive a channel cover 258 to cover an open face of the fluid channel 246. The channel cover 258 extends a full length of the fluid channel 246 to entirely enclose the fluid channel 246. The channel cover 258 may be laser bonded or otherwise joined to the rotor base 240. In the present example, an open faced fluid channel 246 and channel cover 258 are utilized to afford an easy and reliable manufacturing process. Optionally, alternative structures may be utilized to provide the fluid channel, while eliminating the channel cover 258, such as by forming a fluid channel within the monolithic structure of the rotor base 240, thereby avoiding the need to provide the channel cover 258.

The upper surface of the rotor base 240 has a peripheral rib 242 and an interior rib 256 which extend upward from the rotor base 240. The well plate mating face 238 faces in a direction opposite to the peripheral and interior ribs 242, 256. A biasing element 253 (e.g., a wave spring or other structure) is provided within the interior cavity 213 and applies a biasing force against the rotary valve 234. The biasing element 253 is located on the rotor base 240 about the interior rib 256. The biasing element 253 applies an expansion force against the rotor base 240 and the valve cap 210 to maintain a sealed interface between the ports 248, 250 on the rotor valve 234 and ports on the well plate 150.

Figure 2E:
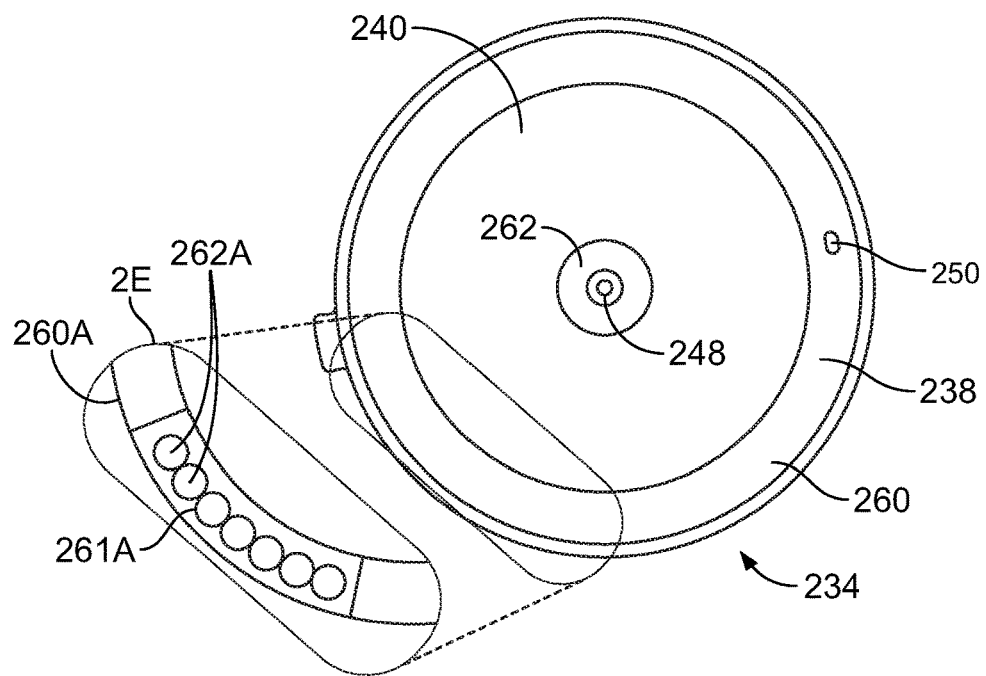
FIG. 2E illustrates a bottom plan view of the rotor valve formed in accordance with an example herein.

FIG. 2E illustrates a bottom plan view of the rotor base 240. The well plate engaging face 238 is formed by an interface ring 260 and an interface pad 262. The interface ring 260 extends about a perimeter of the rotor base 240. With reference to FIG. 2C, the interface pad 262 in the interface ring 260 form a slight standoff to maintain the rotor base 240 off of the well plate 150. In one example, the interface ring 260 may be formed with a smooth flat lower surface. In another example, the interface ring 260 may be formed with a predetermined pattern formed on the outer surface of the interface ring 260 in order to reduce the contact area between the interface pad 260 and the well plate 150. For example, the pattern may comprise a collection of inter-connected circular or O-ring shaped features formed on the interface ring 260 (e.g., in a chain pattern). For example, detail 2E is illustrated with an alternative configuration for the surface of the interface ring 260. At detail 2E, the interface ring 260A is provided with a series of circular raised rings/portions 261A that surround recesses 262A. For example, the pattern in detail 2E may resemble a chain or series of adjoining eights, although alternative patterns maybe used. When not in use, the interface ring 260A may be rotated to a position at which the recesses 262A align with the ports in the well plate to avoid creep in the port structure.

The rotor base 240, interface ring 260 and interface pad 262 may be formed from a multi-shot (e.g. two shot) molding process with the rotor base formed of one type of material, while the interface ring 260 and interface pad 262 are formed of another type of material. For example, the interface pad 262 and the interface ring 260 may be formed from a thermoplastic elastomer (TPE) or other similar materials. The radial port 250 extends through the interface ring 260. The interface pad 262 is formed about the central port 248. The central port 248 is positioned to align with the central feed port 161 on the well plate 150, while the radial port 250 is rotated to align with different well transition ports 162. The central interface pad 262 and interface ring 260 are formed during a common injection molding operation by injecting a thermoplastic elastomer at one or more gates. The radial port 250 may be formed as an oval with an elongated dimension extending along an arc (relative to the central port 248) about the interface ring 260. The oval shape of radial port 250 affords a predetermined amount of tolerance when aligning with a mating well port.

Figure 2F:
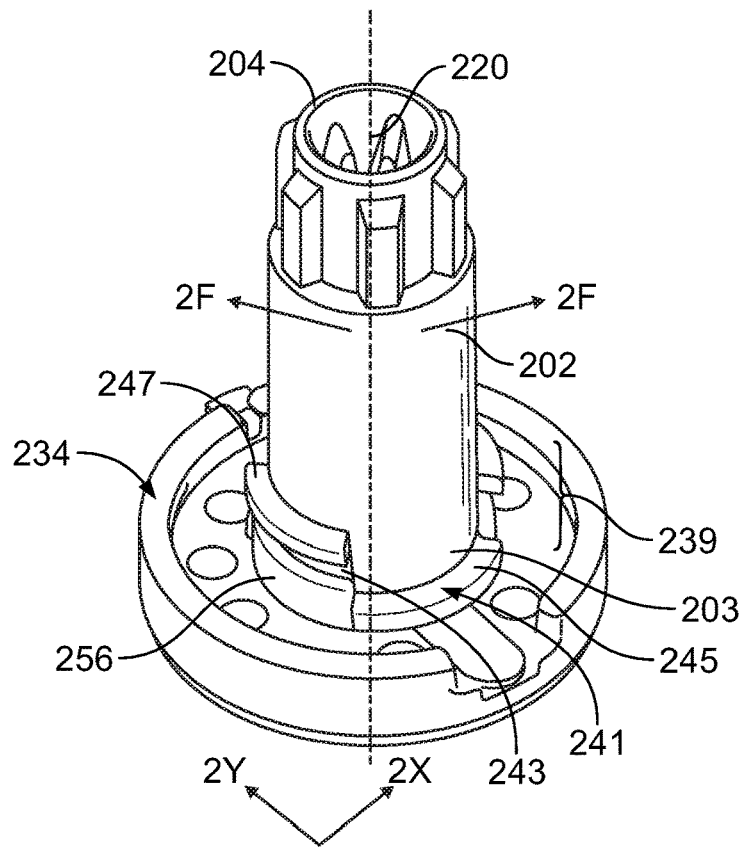
FIG. 2F illustrates a side perspective view of the rotor shaft and rotor valve with the rotor cap removed in accordance with an example herein.

FIG. 2F illustrates a side perspective view of the rotor shaft 202 and rotor valve 234 (with the rotor 210 removed). FIG. 2F illustrates the rotor shaft 202 extending along the rotational axis 220. The proximal end 203 of the rotor shaft 202 is securely mounted to the rotary valve 234 through a load coupling interface 239. The load coupling interface 239 is formed with the interior ribs 256 which hold a coupling flange 241 therein. The coupling flange 241 includes a sidewall 243 that extends along desired segments of the rotor shaft 202. The sidewall 243 includes a base segment 245 and upper segment 247 that extend at least partially about the rotor shaft 202. The coupling flange 241 enables the rotor shaft 202 to be decoupled (e.g. separately molded) from the rotor valve 234, thereby offering molding advantages. In addition, the coupling flange 241 decouples side loads experienced upon the rotor shaft 202 from the rotor valve 234. For example, side loads may be experienced in various radial directions as noted by arrows 2F which may cause slight deflections of the rotor shaft 202 in the corresponding radial direction. The coupling flange 241 allows a predetermined amount of tilting movement between the rotor shaft 202 and rotor valve 234, such as in the directions of arrows 2F, while the rotor valve 234 remains at a relatively fixed orientation with respect to the surface of the well plate. As a further example, the rotor valve 234 may be maintained in a predetermined plane as denoted by coordinate XY.

Returning to FIGS. 2A, 2B, and 3C, the rotary valve assembly 200 is maintained at a predetermined fixed position on the well plate through various features. The latch arms 226 fixedly locate the valve cap 210 at a predetermined XY position on the well plate 150 relative to the wells 156 (FIG. 3C). The detents 158 (FIG. 3C) on the walls of the wells 156 hold the latch arms 226 and valve cap 210 downward. The cap extension 216 maintains the rotor shaft 202 at a predetermined XY position, and orients and permits rotation around the rotational axis 220. The biasing element 253 provided about the interior ribs 256 abuts against an interior shelf 221 provided within an interior cavity 213 within the cap base 214 (FIG. 2B). The interior shelf 221 maintains a downward force on the biasing element 253, thereby holding the rotor base 240, the interface ring 260 and the central interface pad 262 firmly against a surface of the well plate 250, while permitting rotation movement.

Illumination Chamber

Figure 4A:
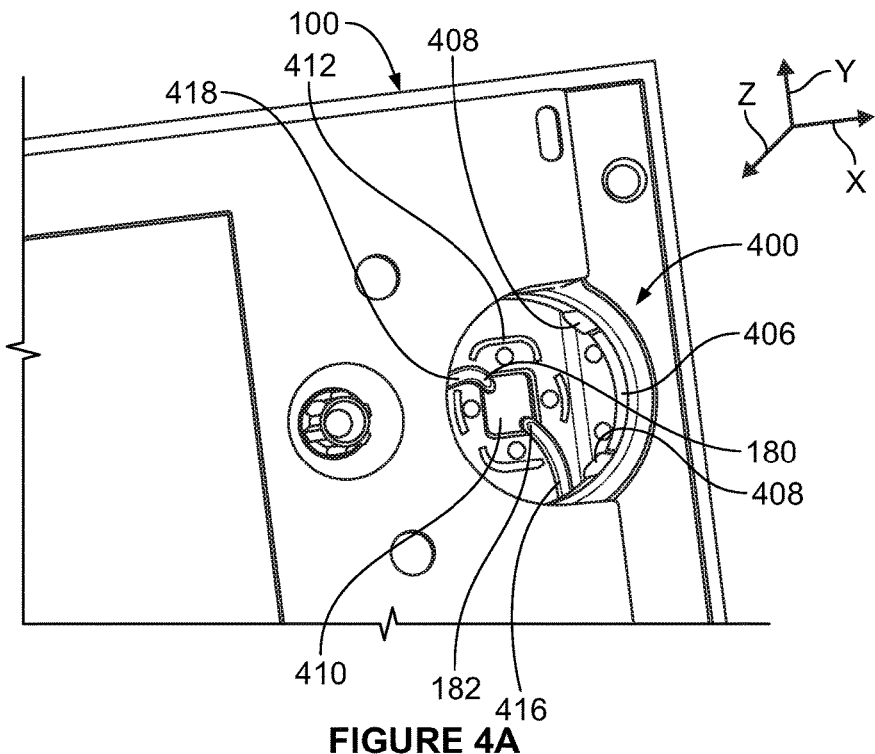
FIG. 4A illustrates a bottom view of a portion of the cartridge assembly to illustrate the illumination chamber in more detail in accordance with examples herein.

FIG. 4A illustrates a bottom view of a portion of the cartridge assembly 100 to illustrate the illumination chamber 400 in more detail. The illumination chamber 400 is to receive an illumination element on the instrument. For example, the illumination element may represent one or more LEDs. The illumination element is positioned within the illumination chamber 400 in accordance with predefined XYZ coordinates. As explained hereafter, the LED illumination element is inserted into (e.g., docks within) the illumination chamber 400 at a well-defined XYZ position, where the position of the LED illumination element is defined by position limiting features within the illumination chamber 400.

Figure 5A:
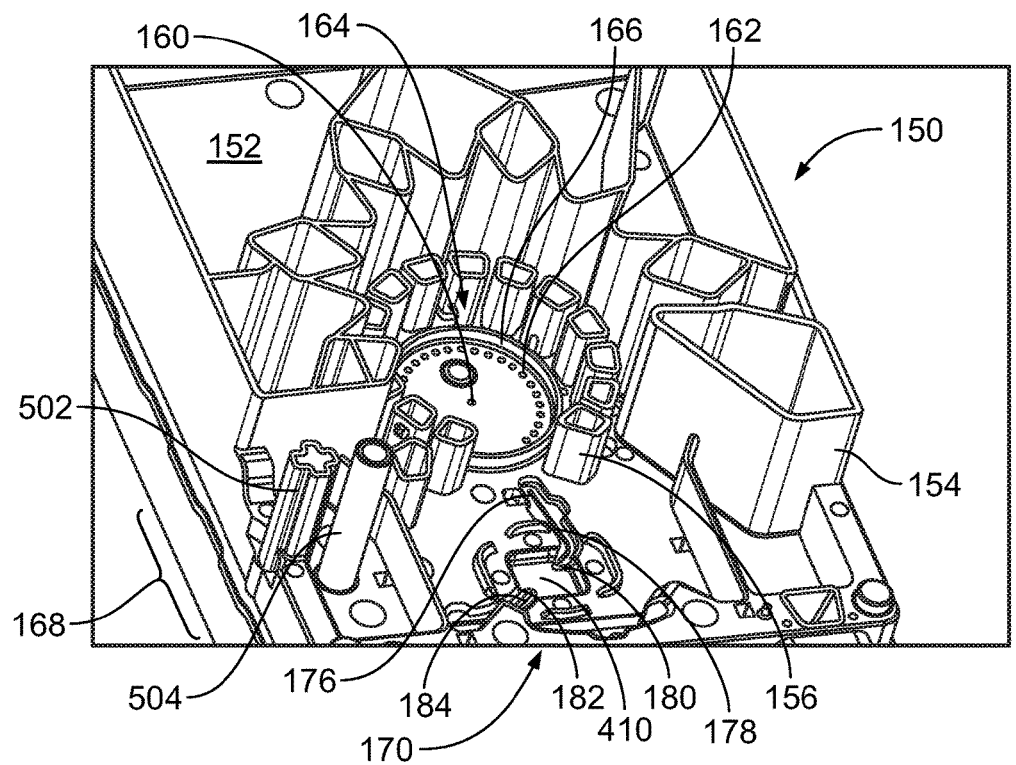
FIG. 5A illustrates a front perspective view of the well plate formed in accordance with an example herein.
Figure 5B:
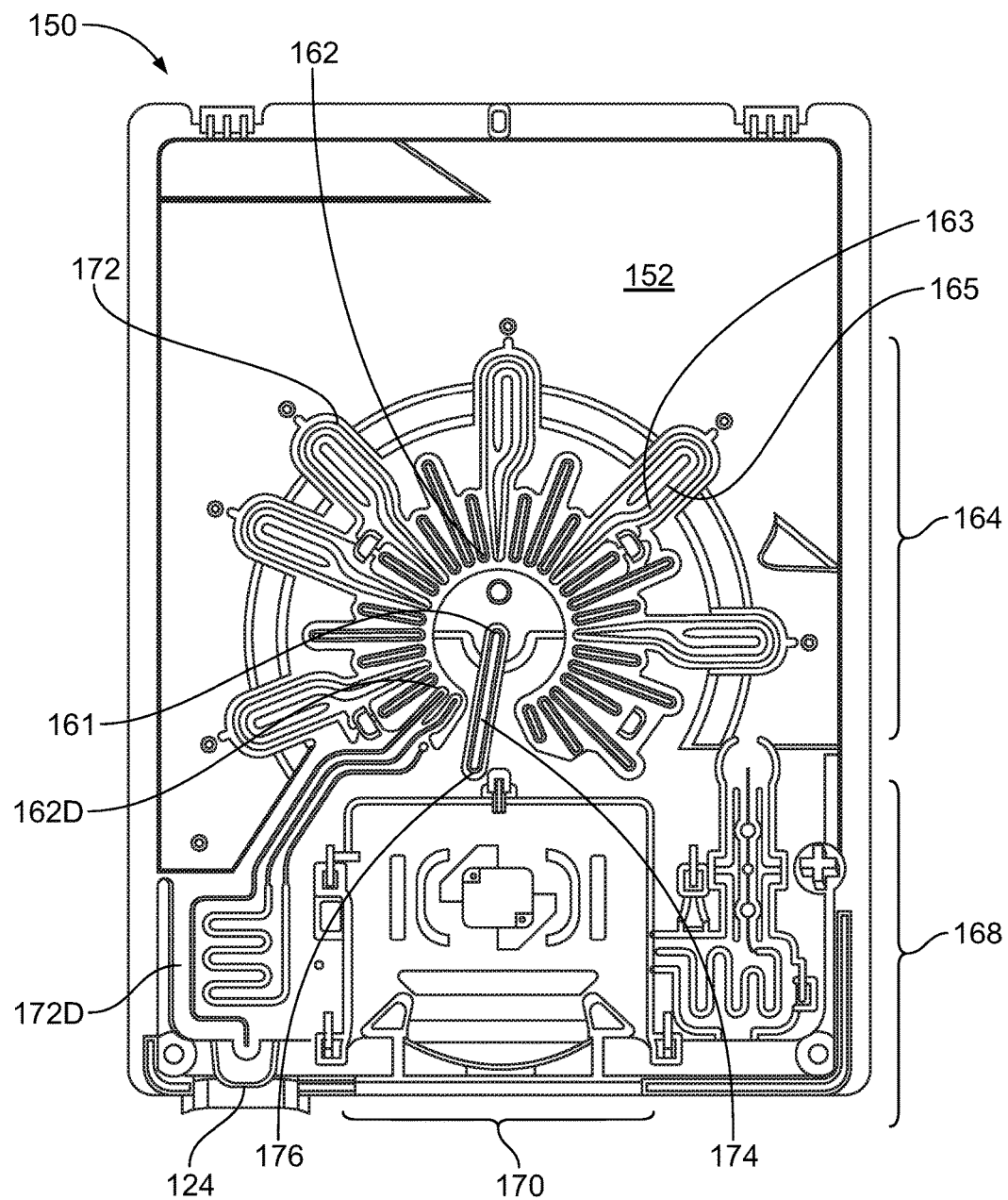
FIG. 5B illustrates flow channels provided on the back surface of the base of the well plate in accordance with an example herein.
Figure 5C:
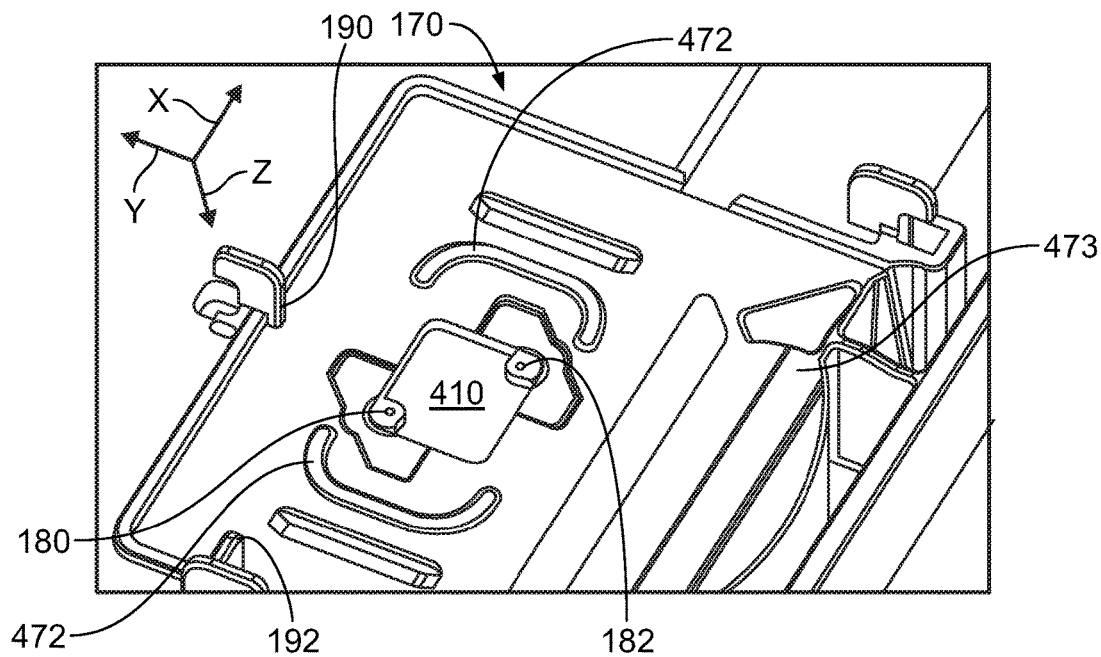
FIG. 5C illustrates a bottom plan view of a portion of the base to provide a more detailed view of the fluidics analysis station on the back surface of the well plate in accordance with examples herein.
Figure 5D:
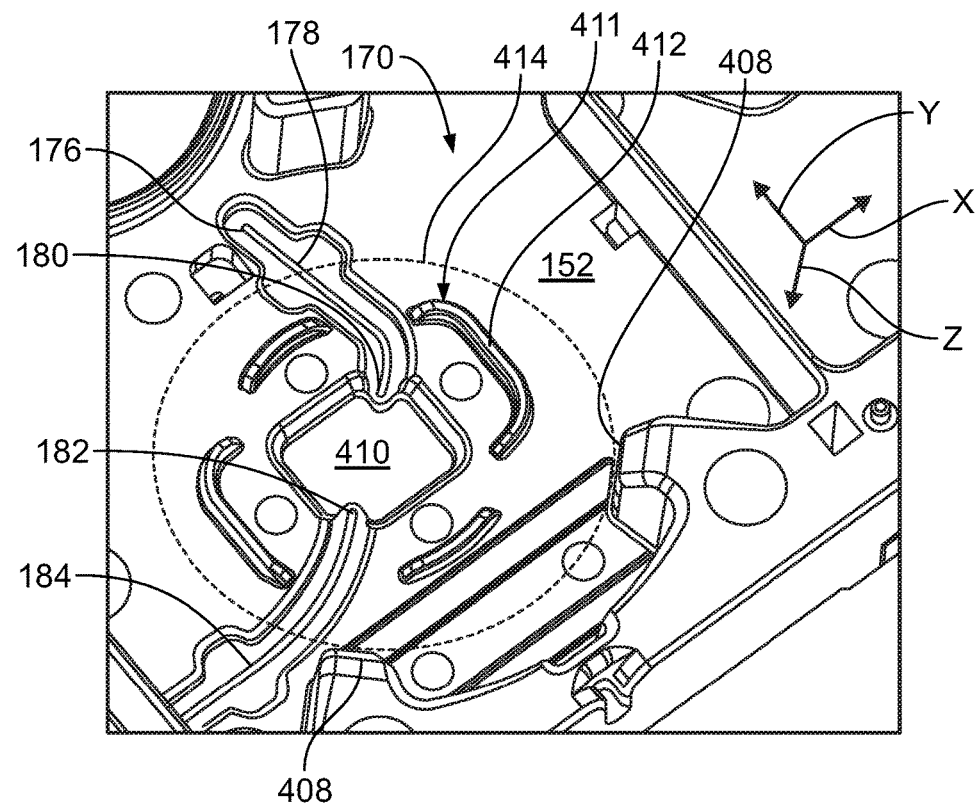
FIG. 5D illustrates a top plan view of a front/top portion of the base corresponding to FIG. 5C to provide a more detailed view of the fluidics analysis station on a front surface of the well plate in accordance with examples herein.

With joint reference to FIGS. 1A, 5C, and 5D, the illumination chamber 400 is formed with a circular peripheral wall 406 on one side and position limiters 408 (FIG. 5D) on an opposite side. The position limiters 408 are provided at select points around the fluidics analysis station 170. The position limiters 408 engage mating features on a peripheral outer wall of the illumination element to position the illumination element at a known desired position, such as in an XY direction relative to an optical interface window 410 provided on the well plate 150. In the present example, the XY direction extends in a plane substantially parallel to a surface of the optical interface window 410. In addition, one or more ribs 412 are provided on the well plate 150 and positioned about the optical interface window 410. The illumination element abuts against (docks to) the ribs 412 when inserted in the Z-direction (providing a Z datum point for the illumination element). The ribs 412 abut against a front face of the illumination element to manage movement of the illumination element in the Z-direction (i.e. toward and away from the optical interface window 410). Optionally, additional or fewer limiters 408 and ribs 412 may be utilized in connection with managing a position of the illumination element. Optionally, the XYZ directions may be oriented in different manners.

As described herein in more detail, channel covers are formed over fluid channels that communicate with the optical interface window 410. By way of example, the fluid channels may be formed in the upper surface of the well plate 150 with an open side, such that the channel covers are laser bonded (or otherwise joined with) over the fluid channels.

Figure 4B:
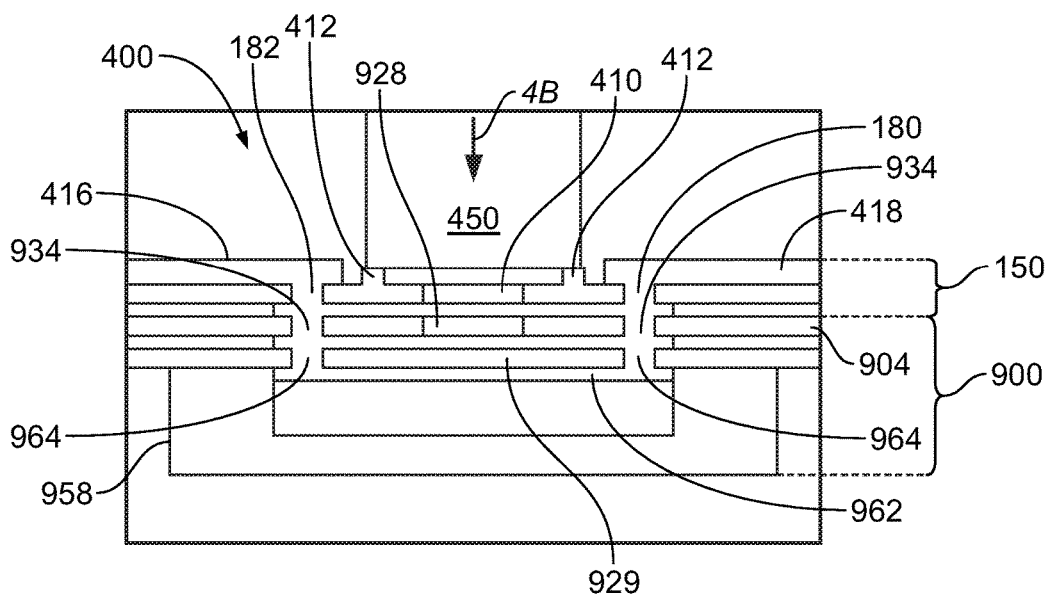
FIG. 4B illustrates a model side sectional view through the various structures provided at the fluidics analysis station once a flow cell cartridge is inserted and an illumination element is inserted into the illumination chamber in accordance with an example herein.

FIG. 4B illustrates a model side sectional view through the various structures provided at the fluidics analysis station 170 once a flow cell cartridge 900 is inserted and an illumination element is inserted into the illumination chamber in accordance with an example herein. In FIG. 4B, an illumination element 450 is illustrated in an operative position above a well plate 150 while a flow cell cartridge 900 is inserted into the flow cell chamber 108. The structures of the well plate 150, visible in FIG. 4B, include the window 410, ribs 412, ports 180, 182 and channel covers 416 and 418. The structures of the flow cell cartridge 900, visible in FIG. 4B, include the top frame 904, flow cell window 928, ports 934, and analysis circuit 958. The analysis circuit 958 includes the active area 962 and active area ports 964. The illumination chamber 400 is oriented to extend along an illumination axis 4B that extends through the interface window 410, flow cell window 928, the transparent layer 429, and the active area 962 within the analysis circuit 958.

The illumination element 450 is inserted into the illumination chamber 400 until resting against the ribs 412 on the well plate 150. The ribs 412 defined the Z datum point (Z reference point) for the illumination element 450 at a predetermined (e.g. minimum) distance above the window 410. Light radiating from the illumination element 450 passes through the window 410, the flow cell window 928 and a transparent layer 929 on the top surface of the analysis circuit 958. The ports 180, 182 in the well plate 150 manage inlet and discharge of fluid through channels below the channel covers 416, 418. The ports 180, 182 align with ports 934 in the top frame 904 of the flow cell cartridge 900, while the ports 934 align with ports 968 into the analysis circuit 958. As one direction of flow, fluid may travel in through the channel corresponding to channel cover 418 and pass downward through ports 180, 194 and 964. The fluid travels across the active area 962 until discharged from ports 964, 934, and 182 into the channel corresponding to channel cover 416. Optionally, the direction of flow may be reversed.

Optionally, one or more electrodes may be positioned proximate to one or more of the ports 180, 182, 934, or 964 with the electrodes maintained at a desired voltage. In addition, the analysis circuit may function as an opposite voltage potential to create a voltage potential through the fluid within the active area.

Well Plate

Next, the well plate 150 and a network of fluid channels through the well plate 150 is described in more detail in connection with FIGS. 5A-5E. The well plate 150 provides a low profile channel construction. By way of example, the well plate 150 may be formed with a base layer having a network of open sided fluid channels formed on one or both sides thereof. The top and/or bottom sides of the base layer are joined, in a sealed manner, to a corresponding backing layer (e.g., a plastic film) to close the open sides of the fluid channels. For example, when only the bottom side of the base layer includes open sided channels, a backing layer may only be provided over the bottom side. Similarly, when the top side of the base layer is the only sided includes open sided channels, a backing layer may be only provided over the top side. When the top and bottom sides of the base layer include open sided channels, top and bottom backing layers may be provided over the corresponding top and bottom sides of the base layer.

Optionally, one or both of the base and backing layers may be formed as a polypropylene film, thermoplastic elastomer, vulcanized thermoplastic elastomer and the like. The base and backing layers may be joined with one another in various manners, such as laser bonding. The base layer includes a network of ports extending through the base layer to provide a manner to interconnect channels provided on the top or bottom sides of the base layer.

All or portions of the base may be formed from a carbon filled black plastic or similar material. The carbon filling facilitates laser bonding with mating structures and renders the corresponding areas at least partially nontransparent. By utilizing a black plastic or another nontransparent material, the well plate 150 affords a desired amount of immunity to light exposure and reduces auto fluorescence of a flow cell cartridge by preventing undesired transmission or reflection of florescent light. The well plate 150 also reduces optical noise within the system by preventing undesired transmission or reflection of light.

FIG. 5A illustrates a front perspective view of the well plate 150 formed in accordance with an example herein. FIG. 5B illustrates a bottom surface of the base 152 of the well plate 150 to better illustrate an example of a network of open sided channels therein. As noted above, a backing layer may be provided over the bottom surface of the base 152 to close the open sided channels. The well plate 150 includes a valve station 164, pump station 168 and fluidics analysis station 170. A sample inlet channel 172D extends from the sample inlet 124 to a sample transition port 162D. A front surface of the base 152 includes the plurality of wells 154, 156 located about the valve station 164. A portion of the wells 156 are arranged in a circular pattern about a valve station 164. Within the valve station 164, a circular flange 166 is formed on (and extends upward from) the base 152. The flange 166 has an internal circular shape that matches the shape of the rotor base 240. The flange 166 and area of the well plate within the flange 166 act as a starter for the rotary valve assembly 200. An internal surface of the flange 166 has an interior diameter that substantially corresponds to an outer diameter of the rotor base 240, thereby forming a guide within which the rotor base 240 rotates. Optionally, the flange 166 may also facilitate maintaining the sealed relation between the rotor-base 240 and well plate 150.

An array of well transition ports 162 are provided in the base 152 within the region interior to the flange 166. The well transition ports 162 are formed in a predetermined pattern corresponding to a pattern and range of motion of the rotary valve assembly 200, such as along a circular arc having a predefined radius. For example, the well transition ports 162 may be formed along a circle having a radius that is equal to the length of the fluid channel 246 (FIG. 2C). A central feed port 160 is provided at a center of the flange 166 and a center of the circle defined by the well transition ports 162. The central feed port 161 is positioned to align with the rotational axis 220 of the rotor shaft 202, which also corresponds to the central port 248 formed through the rotor valve 234.

The pump station 168 includes first and second support posts 502, 504 that extend upward from the base 152. The support posts 502, 504 receive a drive shaft and a syringe arm of the pump assembly 500. The support posts 502, 504 guide movement of the drive shaft and syringe arm along predetermined reciprocating linear paths move fluids through the cartridge assembly 100. The fluidics analysis station 170 delivers fluid to, and removes fluid from, a flow cell.

FIG. 5B illustrates a network of open sided flow channels 172 provided on the bottom surface of the base 152 of the well plate 150. The flow channels 172 extend through the pump station 168, valve station 164, and fluidics analysis station 170. Additionally or alternatively, the flow channels 172 may pass through additional stations. The flow channels 172 may be formed in various patterns and have varying lengths and diameters.

Figure 5E:
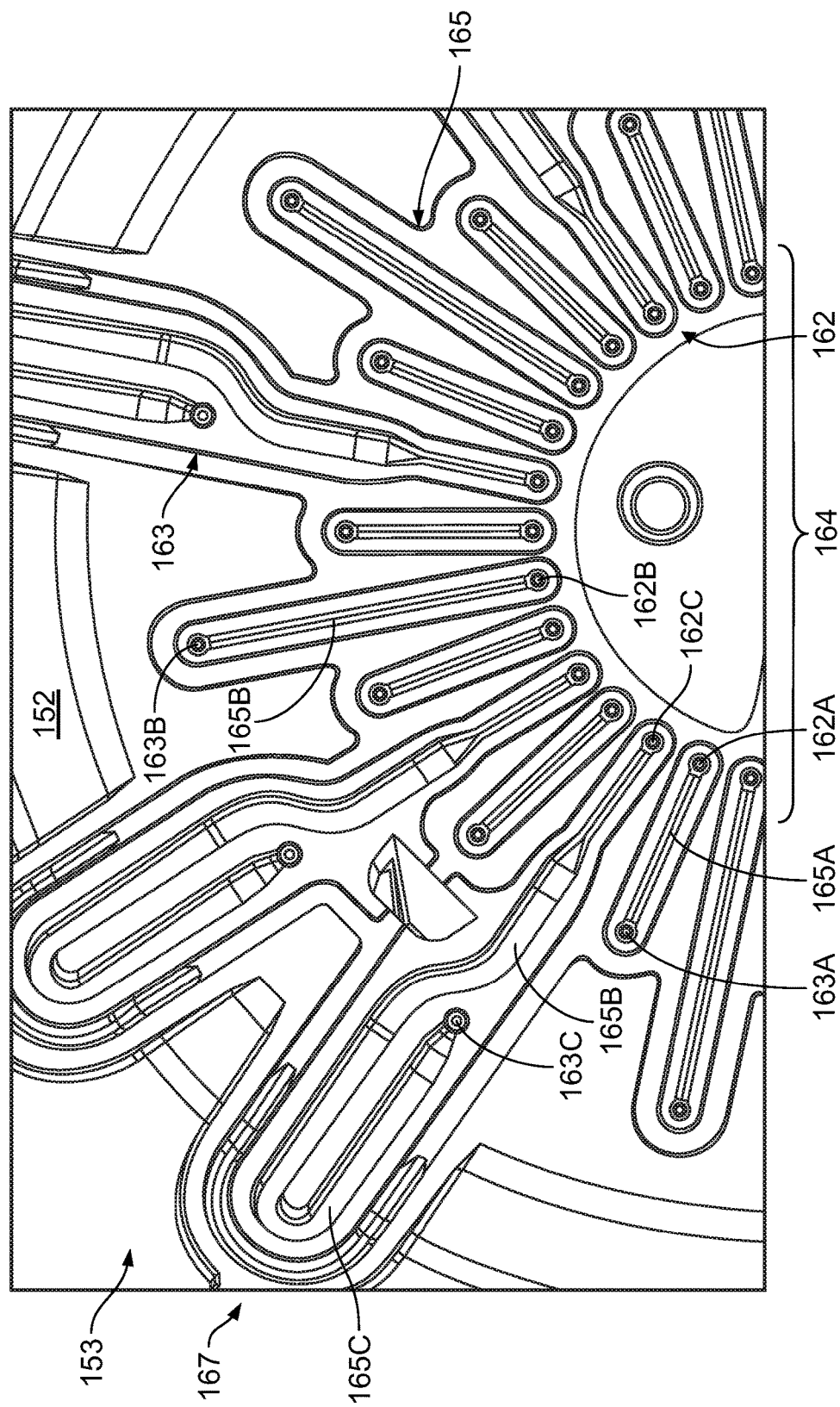
FIG. 5E illustrates an enlarged portion of the bottom surface of the base proximate to the valve station in accordance with examples herein.

FIG. 5E illustrates an enlarged portion of the bottom surface 153 of the base 152 proximate to the valve station 164. The valve station 164 includes the well transition ports 162 arranged in the predetermined pattern (e.g. circular pattern) corresponding to a path followed by the rotary valve assembly 200. The well plate 150 further includes well discharge ports 163 that extend through the base 152 and open onto a top side of the base 152 within a corresponding well (not visible in FIG. 5A). Each well discharge port 163 is joined to a corresponding well transition ports 162 through a well discharge channel 165. The well plate 150 includes a plurality of the well discharge channels 165 dependent upon the number and position of the wells 154, 156. The well discharge channels may be shaped in various manners, such as a straight line, serpentine path, U-shaped path and otherwise. In the example of FIG. 5E, a collection of short straight well discharge channels 165A extend between corresponding well transition ports 162A and well discharge ports 163A that align with the smaller closer wells 156 (FIG. 5A). A collection of longer straight well discharge channels 165B extend between corresponding well transition ports 162B and well discharge ports 163B that align with the larger wells 154 located radially outward beyond the wells 156. In addition, cache storage areas 167 are provided that include storage channels 165C that are loaded and unloaded at storage ports 162C. At various points during operation, it may be desirable to temporarily store a portion of the fluid without dumping to waste. Accordingly, the fluid is moved to an available storage channel 165C. Optionally, an opposite end of the storage channels 165C may include a port 163C to allow air (or an inert fluid) to enter and leave the storage channel 165C. Optionally, the ports 163C may be joined to corresponding storage wells on the well plate 150.

FIG. 5C illustrates a bottom plan view of a portion of the base 152 to provide a more detailed view of the fluidics analysis station 170 on the back surface of the well plate 150. A flow cell is inserted to align with station 170 during operation. The fluidics analysis station 170 includes the optical interface window 410, which is bordered diagonally on opposite corners by interface ports 180 and 182. The interface ports 180 and 182 are coupled to ports on a flow cell when the flow cell is inserted. Limit posts 190 and 192 are located along one or more sides of the fluidics analysis station 170. The limit posts 190, 192 are engaged by the flow cell when inserted to properly align the flow cell relative to the optical interface window 410 and interface ports 180, 182 in the XY direction.

The back surface of the well plate 150 also includes ribs 472 that extend outward (downward) from the bottom surface of the well plate 150. For example, the ribs 472 may align with an extension in the opposite direction from ribs 412 (FIG. 5D). The bottom surface of the well plate 150 also includes a Z position pad 473. An outermost surface of the Z position pad 473 and the ribs 472 are aligned in a common predetermined plane to define a Z datum point, at which the flow cell cartridge 900 is to be positioned when loaded. As explained herein, the flow cell cartridge 900 includes a top frame having an upper surface that abuts against the Z position pad 473 and ribs 472 to maintain the flow cell window and ports at a predetermined Z position relative to the bottom surface of the well plate at the fluidics analysis station 170.

FIG. 5D illustrates a top plan view of a front/top portion of the base 152 corresponding to FIG. 5C to provide a more detailed view of the fluidics analysis station 172 on a front surface of the well plate 150. The front/top portion of the base 152 within the fluidics analysis station 172 corresponds to the illumination chamber 400 (FIG. 4) and accordingly the reference numbers used in connection with FIG. 4 are utilized in connection with FIG. 5D. As shown in FIG. 5D, position limiters 408 are provided along one or more sides of the illumination station 172 and engage mating features on a peripheral outer wall of an illumination element. By way of example only, a dashed circular line 414 is provided to indicate the footprint of the illumination element once inserted by the instrument. The position limiters 408 locate the illumination element at a predefined XY coordinate position (where the XY coordinate system extends in a plane substantially parallel to the surface of the well plate 150 and optical interface window 410).

The well plate 150 includes, on the top side thereof, one or more insertion limit elements 411 to register the illumination element of the instrument at a predetermined distance from the optical interface window 410. The insertion limit elements 411 engage an illumination element on the instrument during a micro-fluidics analysis operation. By way of example, the insertion limit elements 411 may include one or more ribs 412 that are provided along one or more sides of the optical interface window 410 and project upward from the optical interface window 410 by a predetermined distance that is defined to maintain a desired offset between a distal surface of the illumination element (e.g., a lens) and the optical interface window 410. The ribs 412 on the top side of the well plate 150 align with the ribs 472 on the bottom side of the well plate 150. The ribs 412 locate the illumination element at a predefined Z-tolerance or Z-coordinate position (where the Z axis of the reference coordinate system extends in a plane substantially perpendicular to the surface of the well plate 150 and the surface of the optical interface window 410). By way of example, the ribs 412 may register an LED light within an illumination element to a predetermined surface (e.g. the optical interface window 410) while minimizing a Z-tolerance between the LED light source on the instrument and the flow cell below the optical interface window 410.

Within the valve station 164, a select well transition port 162 is coupled (through the rotor valve 234) to the central feed port 160. The central feed port 160 is coupled through a channel 174 to a transition port 176 which transfers the direction of flow to the opposite side of the base 152. With reference to FIG. 5A, the transition port 176 is illustrated in the fluidics analysis station 170. An illumination channel 178 continues from the transition port 176 to interface port 180 which is located proximate to the optical interface window 410. The fluids pass through flow cell channels on the flow cell until the fluids are discharged from the flow cell at a flow cell port 182. The fluid is then conveyed from the interface port 182 along a flow cell channel 184.

FIG. 5D also illustrates in more detail the illumination channels 178 and 184 formed in accordance with one example, with the illumination channels 178, 184 terminating proximate to the optical interface window 410 at corresponding interface ports 180, 182. The illumination channels 178, 184 may be formed as open sided channels on the front surface of the well plate 150 where the open sides are covered with channel covers 416, 418 (FIG. 4). The illumination channel 178 begins and terminates at transition port 176 and interface port 180, respectively. The illumination channel 184 begins and ends at interface port 182 and a pump station port (not visible in FIG. 5D), respectively.

The examples described herein generally described one direction of fluid flow. However, it is recognized that the fluidics analysis operations may be performed in connection with fluid flow traveling in the opposite direction. Additionally or alternatively, fluids may be managed to flow in different directions within the various channels at different stages of a fluidics analysis. Therefore, to the extent any port, channel or other structure is assigned a name descriptive of a flow direction, it is recognized that such descriptor is merely an example and that the port, channel or other structure may be utilized to convey fluids in the opposite direction.

Syringe Pump Assembly

Next, the syringe pump assembly 500 will be described in connection with an example herein with reference to FIGS. 6A-6E. As explained herein, the syringe pump assembly 500 provides a bidirectional pumping action that avoids adverse backlash effects. The syringe pump assembly 500 is reciprocally moved by applying a drive force in one direction and permitting a biasing force to move a plunger arm in an opposite direction, thereby avoiding a need to apply a pulling force to the pump assembly 500.

Figure 6A:
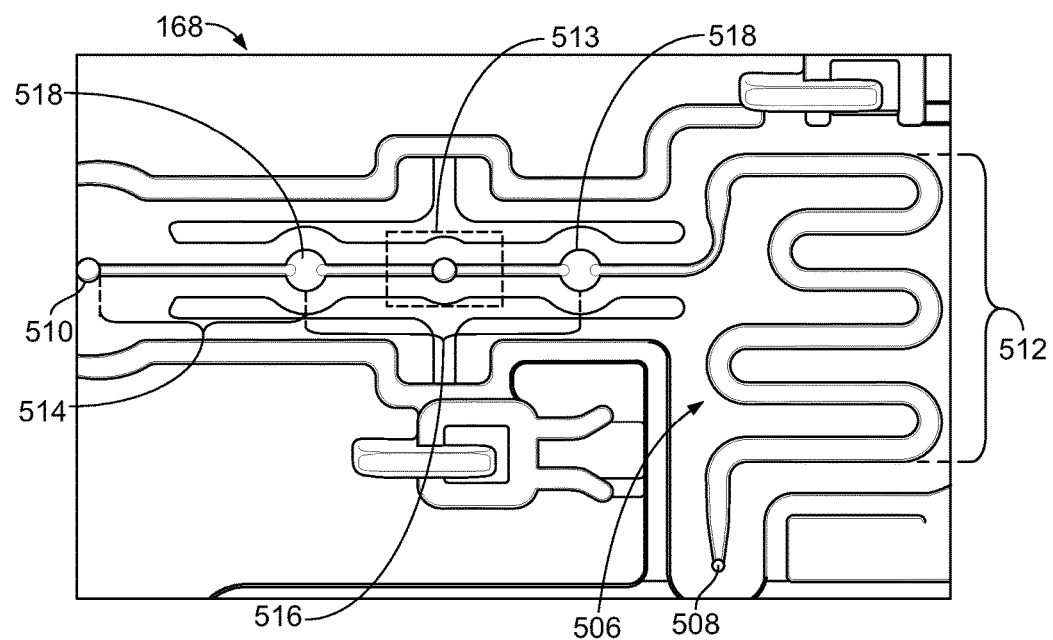
FIG. 6A illustrates a top plan view of the pump station on the well plate in accordance with an example herein.

FIG. 6A illustrates a top plan view of the pump station 168 on the well plate 150 provided in accordance with an example herein. The pump station 168 includes a pump channel segment 506 that is joined at one end to a station inlet port 508 and at an opposite end to a station discharge port 510. The pump channel segment 506 may be functionally divided into a preparation segment 512, a discharge segment 514 and a pump work segment 516, all of which are formed continuous with one another to support fluid flow in either direction. The work segment 516 includes a work area 513, in which a plunger 540 moves in a reciprocating manner to introduce alternately a low pressure (e.g. vacuum) and high pressure. The work area 513 is sandwiched between a pair of pinch valves 518 located upstream and downstream of the work area 513. The pinch valves 518 determine the direction of flow from the work area 513, such as toward waste or towards a flow cell. By way of example, the pinch valves 518 may be formed by pressing a material of interest (e.g. a thermoplastic elastomer) into a circular indentations formed along the channel within the work segment 516. As explained herein, the pinch valves 518 are alternately opened and closed in a coordinated manner in connection with the introduction of low pressure and high pressure states within the work area 513 to pull or push fluid through the pump station 168. The preparation segment 512 is located upstream of the work segment 516 between the work segment 516 and the station inlet port 508. The present example, the preparation segment 512 includes a channel that is arranged in a serpentine shape to form a storage area within the pump channel segment 506 to hold a predetermined amount of fluid before the fluid passes through the work segment 516. Optionally, the preparation segment 512 may be lengthened or shortened or entirely eliminated, such as by providing the station inlet port 508 proximate an end of the work segment 516. The discharge segment 514 is located downstream of the work segment 516 between the work segment 516 and the station discharge port 510. In the present example, the discharge segment 514 is provided as a relatively short straight channel, all thorough alternative configurations may be provided with the discharge segment 514 varying in length and pattern, or removed entirely.

Figure 6B:
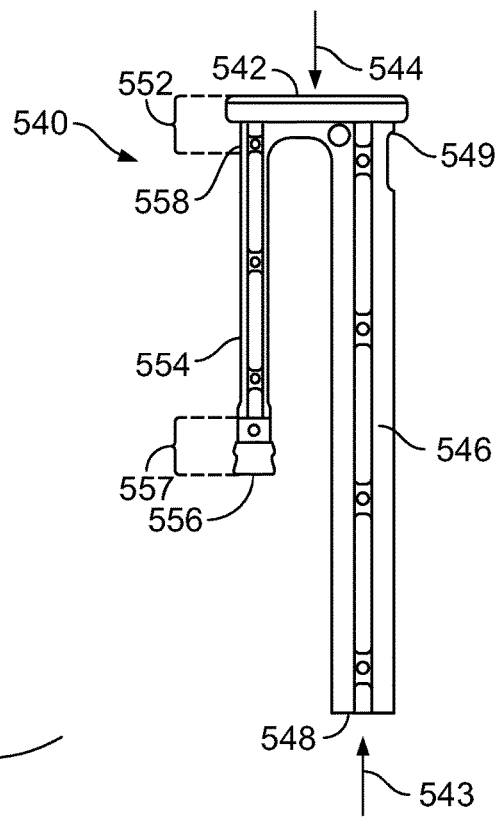
FIG. 6B illustrates a side view of a plunger provided within the pump in accordance with an example herein.

FIG. 6B illustrates a side view of a plunger 540 provided within the pump 500. The plunger 540 generally includes a drive arm 546 and a plunger arm 554 that are joined with one another through a bridge segment 552, all of which are formed together in a monolithic structure (e.g., molded together). The drive arm 546 has a drive end 548 and a distal end 549. The plunger arm 554 includes a work end 556 and a distal end 558. A plunger element 557 that is mounted on the work end 556 of the plunger arm 554. The distal ends 549 and 558 of the drive arm 546 and plunger arm 554 are joined to the bridge segment 552. The plunger arm 554 and drive arm 546 extend downward from the bridge segment 552 in a common direction with the plunger arm 554. The plunger arm 554 is oriented to extend in a direction substantially parallel to the length of the drive arm 546 such that the drive arm 546 and plunger arm 554 move together in a common direction and alignment in response to a drive force 543 and a bias force 544. The drive force 543 and bias force 544 represent uni-directional pushing forces without a corresponding reverse pulling force. The bridge segment 552 includes a biasing surface 542 that is positioned at, and exposed through, the pump access opening 123 (FIG. 1A) formed in the cover 102. A biasing element of the instrument (e.g. a spring) is to engage, and apply a biasing force against, the biasing surface 542. The drive end 548 of the drive arm 546 is positioned at a drive opening 116 in the bottom surface 110 of the cartridge assembly 100 (FIG. 1B) to be engaged by the pump drive assembly of the instrument. The pump drive assembly intermittently applies and removes a drive force 543 to and from the drive arm 546. The drive end 548 and biasing surface 542 are located at opposite ends of the plunger 540. The drive end 548 and biasing surface 542 are exposed at upper and lower surfaces of the housing of the cartridge assembly 100 such that corresponding unidirectional drive and biasing forces 543, 544 are applied thereto in connection with moving the plunger 540 in a reciprocating motion without introducing backlash, while providing direct instrument encoder measurements. The drive and biasing forces 543, 544 apply a bi-directional push system which avoids the need for a push/pull pump driver.

Figure 6C:
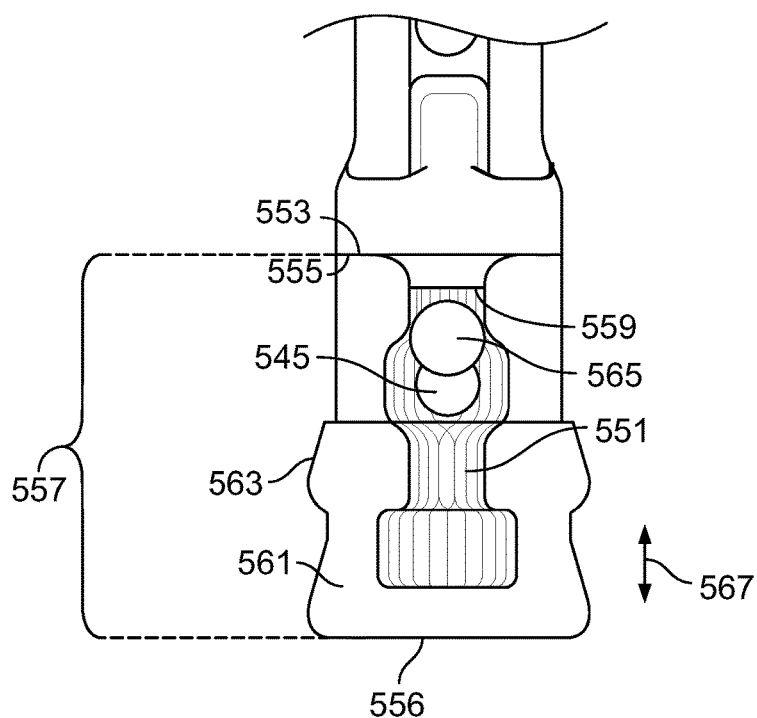
FIG. 6C illustrates an enlarged side view of the plunger element as mounted to the plunger arm in accordance with an example herein.

FIG. 6C illustrates an enlarged side view of the plunger element 557 as mounted to the plunder arm 554. The plunger element 557 is illustrated in a partially transparent manner to illustrate internal structures. The plunger arm 554 includes a leading edge 553, to which one or more stems 559 are formed integrally and in a monolithic structure there with. The stems 559 include a hinge pin 565 extending there between. A support beam 551 is provided with an eye 545 in a proximal end thereof. The eye 545 is elongated and receives hinge pin 565 such that the support beam 551 is movable over a slight predetermined range in the direction of arrow 567 which extends generally parallel to a length of the plunger arm 554 and plunger element 557. Optionally, the stem and support beam 559, 551 may be formed as a common monolithic structure.

The plunger element 557 includes a body 561 that is formed in a generally tubular shape with predetermined contours about a periphery of the body 561. The body 561 includes a trailing edge 555 that is formed in a row with the leading edge 553 of the plunger arm 554 (e.g. through a cold molding operation). The body 561 includes one or more peripheral plunger ribs 563 extending there about that are shaped and positioned to maintain an airtight seal within the interior passage of the support post 504, in which the plunger arm 554 reciprocates.

The plunger element 557 may be formed from a vulcanized thermoplastic elastomer (TPV) or other material that is relatively more flexible and compressible than the plunger arm 554. The drive arm 546, bridge segment 552, and plunger arm 554 are formed from a relatively hard plastic material (e.g., polycarbonate plastic). The plunger element 557 is formed to the plunger arm 554 in a non-snap on manner. As one example, the plunger arm 554 may be molded over the stem 559 and support beam 551. By way of example, a two shot molding process may be used, wherein the plunger arm 554 is molded during an initial molding operation, while the plunger element 557 is added during the second molding operation. By utilizing a molding process, the plunger element 557 is secured to the plunger arm 554 with relatively little or no tolerance or clearance there between (at the leading and trailing edges 553, 555), with the plunger element 557 and plunger arm 554 physically and chemically interlocked to one another (at the leading and trailing edges 553, 555).

By providing a close tolerance between the plunger element 557 and the plunger arm 554, the plunger 540 substantially eliminates or avoids "hysteresis" that might otherwise occur if the plunger element 557 were merely snapped on or otherwise more loosely attached to the plunger arm 554. In addition, by molding the plunger element 557 over the support beam 551 and stem 559, a final structure is provided that facilitates avoidance of hysteresis.

The non-snap on interface between the plunger element 557 and plunger arm 554 affords improvements over a snap on type plunger element which would introduce the potential for the plunger element to move upward and downward relative to the plunger arm each time the direction of motion is changed. When movement is experienced between a snap on plunger and plunger arm, such a configuration creates a potential for backlash, also referred to as hysteresis.

In accordance with examples herein, the plunger 540 moves in both directions numerous times (e.g. a few hundred or thousand pump cycles per run) during operation. The plunger 540 may move at a speed between 0.3 mm/sec to 10 mm/sec. Thus, a snap on type plunger element would create the potential for backlash or hysteresis numerous times throughout a run (e.g. a micro-fluidics analysis operation). By forming the plunger element 557 on a portion of the plunger arm 554 (in a non-snap on manner), examples herein avoid the risk of hysteresis or backlash by maintaining a fixed relation there between.

Returning to FIG. 6B, during operation, the pump drive assembly of the instrument intermittently applies a drive force 543 to the drive end 548 of the drive arm 546 to move the plunger 540 upward in the direction of the drive force 543. When the drive force 543 is removed, the biasing force 544 moves the plunger 540 downward in the direction of the biasing force 544. By applying a biasing force 544, examples herein avoid the need for the pump drive assembly to attach to the drive arm 546 and to avoid the need to apply a pulling force to the drive arm 546. The drive force 543 is intermittently applied and removed, thereby causing the plunger 542 move upward and downward repeatedly throughout operation. As the plunger 540 moves upward and downward, the work and 556 introduces low pressure and high pressure states within the work area 513 (FIG. 6A). As the high and low pressure states are introduced into the work area 513, fluid is pulled and pushed along the channel segment 506. The direction of movement of the fluid through the pump channel segment 506 is controlled by opening and closing the pinch valves 518.

Figure 6D:
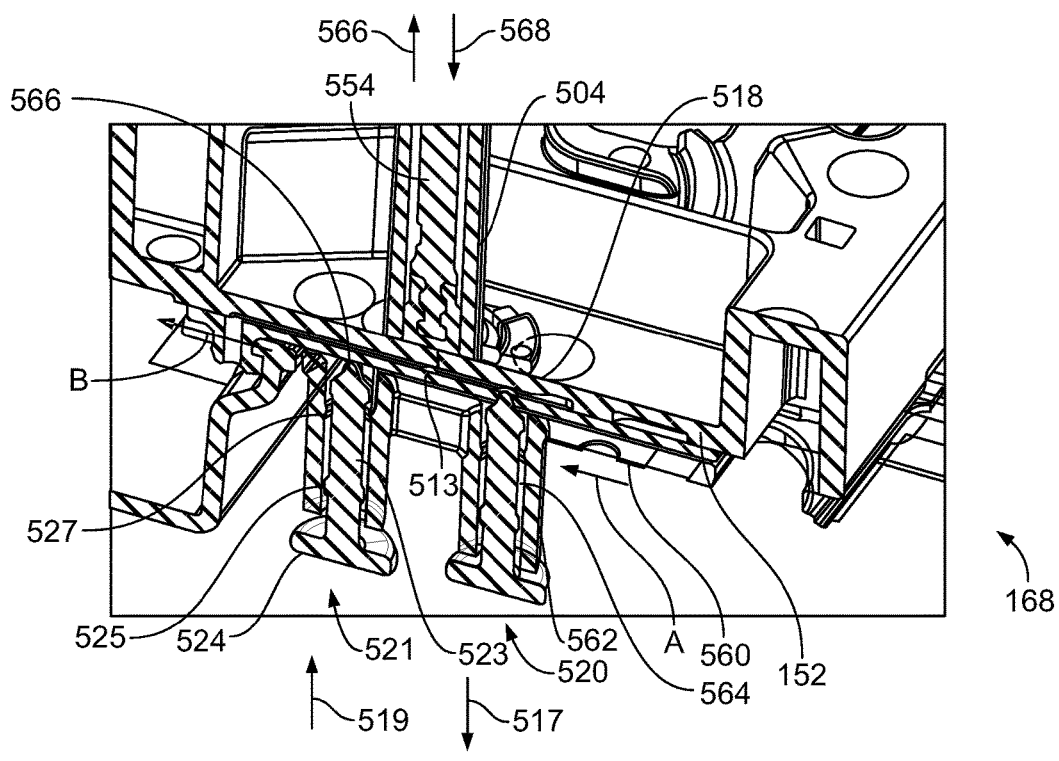
FIG. 6D illustrates a side sectional view of the pump station to better illustrate the pumping operation in accordance with an example herein.

FIG. 6D illustrates a side sectional view of the pump station 168 to better illustrate the pumping operation. Within the pump station 168, a pushpin brace 560 is mounted to a lower surface of the base 152 of the well plate 150. The brace 560 includes support posts 562 that have passages 564 therein. The passages 564 receive corresponding pushpins 520, 521. The pushpins 520, 521 include shafts 523 that include work ends 566 and opposite contact pads 524. The work ends 566 are positioned at the pinch valves 518, while the contact pads 524 are flared radially outward beyond outer ends of the support posts 562. The shafts 523 include one or more exterior ribs 525 extending thereabout. The passages 564 also include one or more interior ribs 527. The exterior and interior ribs 525, 527 cooperate to retain the pushpins 520, 521 within the corresponding passages 564, while permitting the pushpins 520, 521 to move back and forth along the support posts 562 in a valve opening direction 519 and a valve opening direction 517. The contact pads 524 are positioned at the pushpin openings 114 (FIG. 1B) in the bottom surface 110.

During operation, a valve drive element of the instrument is positioned to engage the contact pads 524. The valve drive element applies a valve closing force (in the valve closing direction 519) to one of the pushpins 520, 521, while applying no closing force to the other pushpin 520, 521. When no valve closing force is applied to a pushpin 520, 521, the pushpin 520, 521 moves in the valve opening direction 517 to a valve open state, such that the corresponding pinch valve 518 is open. When a valve closing force is applied and the corresponding pushpin 520, 521 moves in the valve closing direction 519, the corresponding pinch valve 518 is closed. The pushpins 520, 521 and the corresponding pinch valves 518 alternately move between open and closed states.

FIG. 6D also illustrates the plunger arm 554 when loaded within the support post 504. The plunger arm 554 reciprocally moves in a pulling direction 566 and a pushing direction 568 to create corresponding low pressure and high pressure states, respectively, in the work area 513. As the plunger arm 554 is moved in the pulling direction 566, fluid is drawn into the work area 513, where the amount of fluid drawn into the work area 513 is dependent upon the range of motion of the plunger arm 554. When the syringe arm is moved in the pushing direction 568, the fluid within the work area 513 is pushed from the work area 513 back into the flow channel. The direction in which fluid is drawn into the work area 513 from the fluid channel depends on which of the pushpins 520, 521 have closed the corresponding pinch valve 518. For example, to introduce a pulling force in the direction of arrow A, the pushpin 521 would be moved to the closed state to close the corresponding pinch valve 518 while the syringe arm is moved in the pulling direction 566. As the plunger arm 554 withdraws from the work area 513, fluid advances along the flow channel in the direction of arrow A. When the plunger arm 554 reaches an end of a range of motion, the pushpin 521 is released and permitted to move in the opening direction 517 to permit the corresponding pinch valve 518 to open. At the same time, the pushpin 520 is moved in the closing direction 519 to close the corresponding pinch valve. Thereafter, the plunger arm 554 is moved in the push direction 568 to force the fluid from the work area 513 into the fluid channel in the direction of arrow B. When it is desirable to move fluid in the opposite direction, the operation of the pushpins 520, 521 is reversed relative to movement of the plunger arm 554.

Figure 6E:
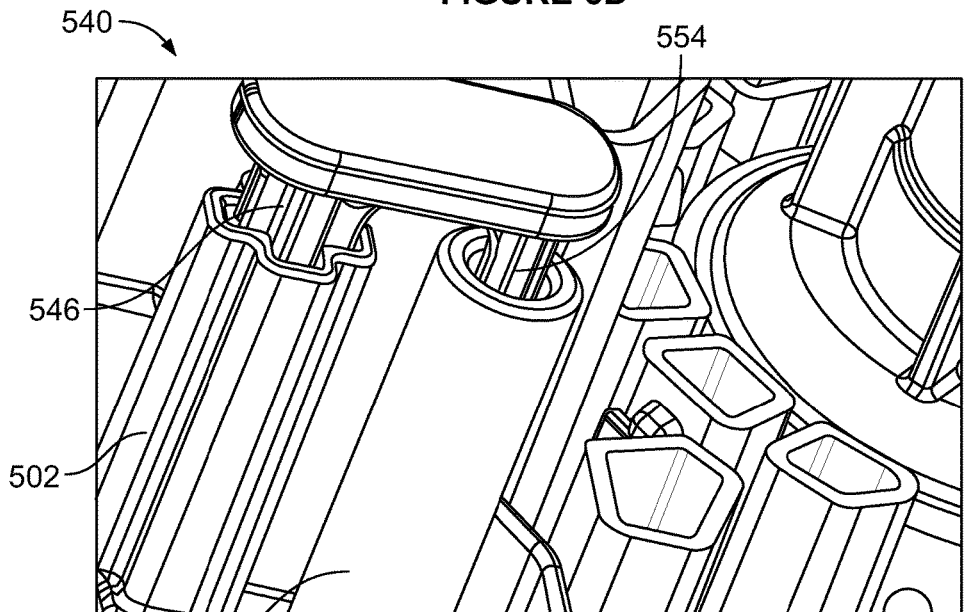
FIG. 6E illustrates an enlarged side perspective view of a portion of the plunger inserted into the support post in accordance with an example herein.

FIG. 6E illustrates an enlarged side perspective view of a portion of the plunger 540 inserted into the support post 502, 504. The plunger arm 554 is slidably received within the support post 504, while the drive arm 546 is slidably received within the support shaft 502. The support shaft 502 and drive arm 546 are formed with a cross section that is X shaped in order to guide the plunger 540 along a predetermined reciprocating path with a relatively small tolerance for error.

Figure 6F:
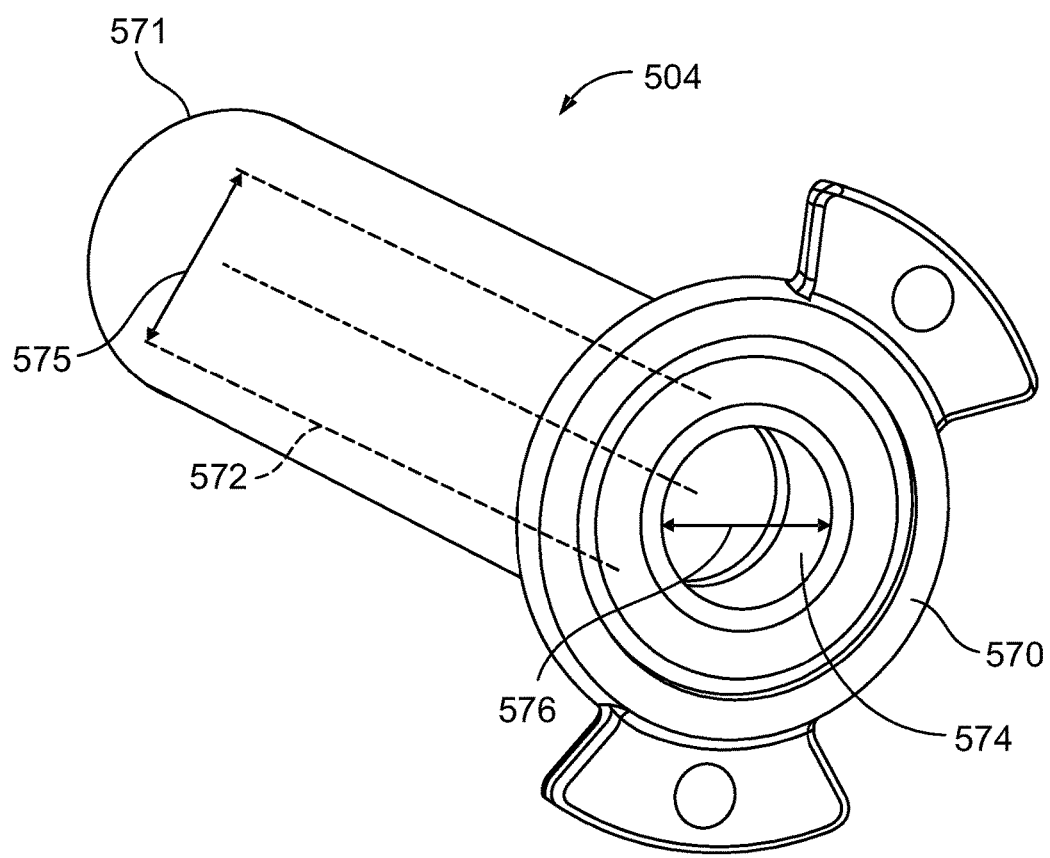
FIG. 6F illustrates a perspective view of the support shaft to receive the plunger arm in accordance with examples herein.

FIG. 6F illustrates a perspective view of the support shaft 504 to receive the plunger arm 554 in accordance with examples herein. The support shaft 504 includes a proximal end 570 and a distal end 571. The proximal end 570 is mounted on the well plate 150 at the pump station 168, while the distal end 571 extends upward from the pump station 168. The support shaft 504 is elongated and includes a passage 572 extending between the proximal and distal ends 570, 571. The passage 572 has a first interior diameter 571 for a segment of the passage 572 that extends from the distal end 571 toward an area near the proximal end 570. The passage 572 has a second larger diameter 576 at the proximal end 570 to form a parking station 574. The parking station 574 is to receive at least the portion of the plunger element 557 that includes the plunger ribs when located in a storage position. The plunger element 557 may be located at the parking station 574 during storage, transportation, or generally when not in use. By allowing the plunger ribs of the plunger element 557 to be retained in the parking station 574 with an enlarged diameter, examples herein avoid creep of the plunger element 557 such that the plunger element 557 and plunger ribs maintain an original shape for a longer period of time without being unduly compressed. Otherwise, creep (or changes in the shape) of the plunger element 557 and plunger ribs may result if stored for extended periods of time within the portion of the passage 572 having the first narrower diameter 575.

Fluidics Instrument

Figure 7:
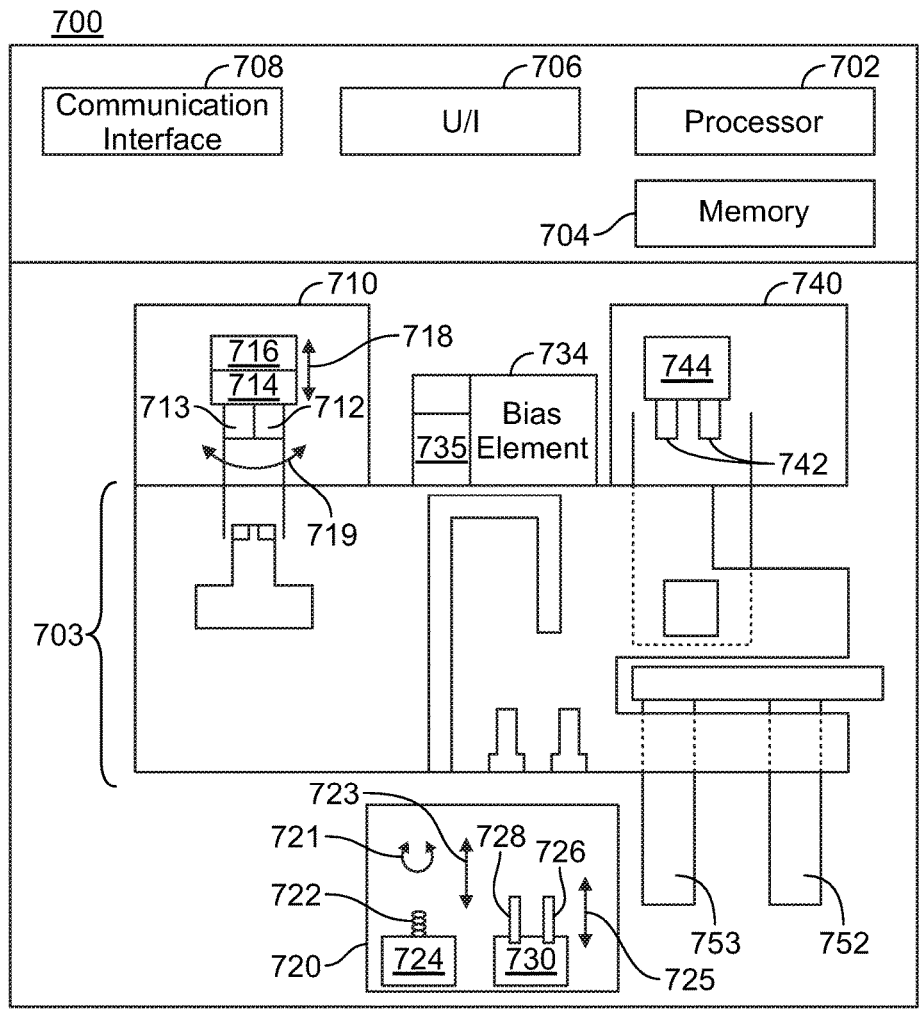
FIG. 7 illustrates a block diagram of a portion of a fluidics instrument utilized in accordance with an example herein.

FIG. 7 illustrates a block diagram of a fluidics instrument 700 implemented in accordance with an example herein. The instrument 700 includes a docking station 703 to receive a cartridge assembly 100. Various electrical, optical and mechanical subassemblies within the instrument 700 interact with the cartridge assembly 100 during a micro-fluidics analysis operation.

The instrument 700 includes, among other things, one or more processors 702 that are to execute program instructions stored in memory 704 in order to perform the micro-fluidics analysis operations. The processor 702 is communicatively coupled to a valve drive assembly 710, pump drive assembly 720, a piercer actuator assembly 740, an illumination element 750, an electrical contact array 752, and a heating element 753.

A user (U/I) interface 706 is provided for users to control and monitor operation of the instrument 700. One or more communications interfaces 708 convey data and other information between the instrument 700 and remote computers, networks and the like. For example, the communications interface 708 may receive protocols, patient records, and other information related to a particular fluidics analysis operation. The communications interface 708 may also convey raw resultant data, as well as data derived from analysis of one or more samples.

The valve drive assembly 710 includes a drive shaft 712 to engage the rotary valve assembly 200. The valve drive assembly 710 also includes a rotation motor 714 and a translation motor 716. The translation motor 716 moves the drive shaft 712 in a translational direction 718 between an engaged state and a disengaged state with the rotor shaft 202 of the rotary valve assembly 200. Once the drive shaft 712 is physically and securely engaged with the rotor valve assembly 200, the rotation motor 714 manages rotation of the drive shaft 712 in a rotary direction 719 to direct the rotary valve assembly 200 to connect and disconnect various wells of reagents to the channels of the well plate.

The valve drive assembly 710 includes a position encoder 713 that monitors a position of the drive shaft 712 relative to the rotor shaft 202 (FIG. 2B). The encoder 713 provides position data to the processor 702 in order to ensure that the splines of the drive shaft 712 are fully engaged with the interior splines 232 of the rotor shaft 202, thereby ensuring that the position encoder 713 closely tracks the rotational position of the rotor shaft 202. By way of example, the encoder 713 may include a shaft having a male encoder spline configuration that is shaped and dimensioned to match the interior splines 232 (FIG. 2B) described above in connection with the rotary valve assembly 200. The encoder splines fully made with and bottom out within the interior splines 232 to maintain a fixed relation there between. The encoder splines do not apply a driving force, but instead merely follow movement of the rotor shaft 202 to provide precise and accurate angular position data to the processor 702. The drive shaft 712 includes a separate set of drive splines that fit over the distal end of the rotor shaft 202. The drive splines fit between and apply a driving force to the exterior splines 230 on the rotor shaft 202.

By maintaining the rotor and drive shafts 202, 712 in a fixed rotational relation, the processor 702 can utilize rotational data obtained from the motor 714 to determine the particular rotational position of the rotary valve 234.

The valve drive assembly 710 is to move (e.g., rotate) the rotor shaft 202 in order to selectively connect the flow channels to one or more of the ports. In many operations, the rotor shaft 202 is rotated varying degrees based on locations of well ports for reagent wells that are successively utilized. For example, when adjacent wells are utilized in order, the valve drive assembly 710 will rotate the rotor shaft 202 only a few degrees. However, when first and second wells are to be used that are on opposite sides of the well plate, the valve drive assembly 710 will rotate the rotor shaft 202 180° or more or less. After rotating the rotor shaft 202, the rotor valve assembly 200 is momentarily stationary to permit a fluid to flow therethrough or to permit a sample to be detected.

The piercer actuator assembly 740 includes one or more piercer shafts 742 and a translation motor 744 to drive the piercer shafts 742 between retracted and extended positions. When the piercer shafts 742 are moved to the extended position, the piercer shaft 742 engages an upper surface of the piercing unit 300 and forces the piercing unit 300 downward to cause the piercing elements on the piercing unit 300 to puncture foils covering corresponding reagent wells. The piercing shafts 742 may remain extended throughout a fluidics analysis operation, or alternatively may be retracted.

A pump drive assembly 720 includes a pump shaft 722 that is coupled to a motor 724 and moves between extended and retracted positions along a pump direction 723. By way of example, the pump shaft 722 may be formed as a screw shaft that is rotated in the directions of arrow 721. By changing the direction in which the pump shaft 722 is screwed, the pump shaft 722 moves inward (in a retracted direction) and outward (in an extended direction) along the pumping direction 723. By repeatedly moving the shaft 723 between retracted and extended positions, the pump shaft 722 applies drive forces 543 to the drive arm 546 to move the pump assembly 500 in a direction that causes the syringe arm 554 to create a low-pressure state at the work area to draw/pull fluid into the pumping station. The drive shaft 722 is repeatedly moved to the retracted position, and a biasing element 734 applies a biasing force to the biasing surface 542 on the pump assembly 500 to move the pump assembly 500 downward in the direction of the biasing force 544, thereby causing the syringe arm 554 to form a high-pressure state at the work area to push fluid from the pumping station.

A position encoder 735 is provided with the biasing element 734. The position encoder 735 tracks a position of the biasing element 734 as the biasing element 734 moves upward and downward with the plunger 540. The position encoder 735 provides position data to the processor 702 in order to track the position of the plunger 540 throughout operation.

The pump drive assembly 720 also includes valve drive shafts 726 and 728 that are positioned to align with the pushpins 520, 521. The valve drive shafts 726, 728 move between extended and retracted positions along arrow 725 by a motor 730. The valve drive shafts 726, 728 are moved in opposite directions, such that when the valve drive shaft 726 is extended, the valve drive shaft 728 is retracted, and vice versa. The valve drive shafts 726, 728 are moved in opposite directions in an alternating manner, synchronized with movement of the pump shaft 722, in order to move fluid through the pump station 168, and thus through the flow cell.

The illumination element 756 is moved into and out of the illumination chamber 400. The illumination element 750 includes an optics system to provide one or more types of illumination light into the elimination chamber 400. By way of example, the elimination element 756 may include an LED light tube and the like, to generate a desired amount and type of light. An electrical contact array 752 and a heating element 753 are inserted into a flow cell cartridge access area 112 in the bottom surface 110 of the cartridge assembly 100. The contact array 752 engages a corresponding array of electrical contact pads 950 on the flow cell cartridge 900. The heating element 753 engages a heat spreader within the flow cell cartridge 900.

In accordance with at least one example, the processor 702 manages operation of the motors, optics, contact arrays and the like. Optionally, numerous processors may be provided that cooperate (e.g. under control of the processor 702) to manage operation of each of the motors, optics, contact arrays, assemblies and components described in connection with the instrument 700.

By way of example, the motors may be direct drive motors. However, a variety of alternative mechanisms may be used, such as direct current (DC) motors, solenoid drivers, linear actuators, piezoelectric motors, and the like.

Fluidics Control System

Figure 8:
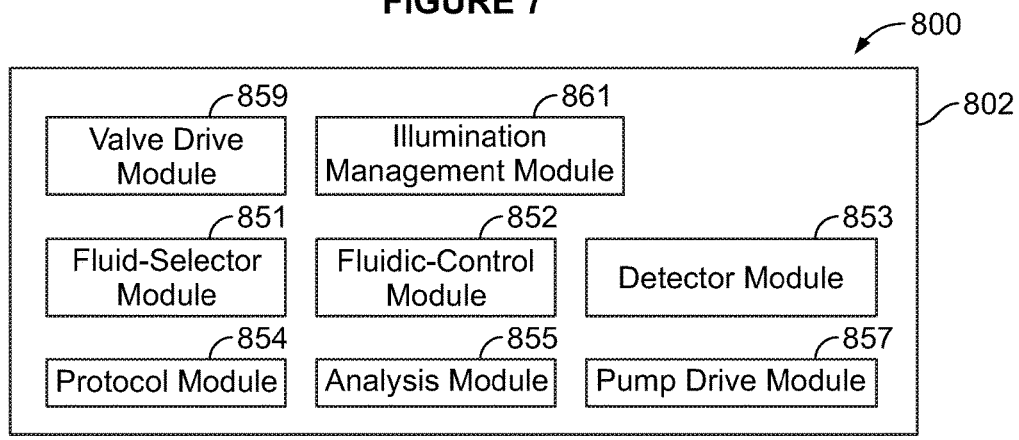
FIG. 8 is a schematic view of a system configured for biological or chemical analysis formed in accordance with one example.

FIG. 8 is a schematic view of a computer system 800, implemented by the instrument 700 of FIG. 7, in accordance with one example. For example, the computer system 800 may be implemented by one or more processors 702 under control of the user interface 708 and program instructions stored in memory 704. Although FIG. 8 shows representative illustrations or blocks of the various components of the computer system 800, it is understood that FIG. 8 is merely schematic or representative and that the computer system 800 may take various forms and configurations.

The computing system 800 may communicate with the various components, assemblies, and systems (or sub-systems) of the instrument. The computing system 800 may include a fluid-selector module 851, a fluidic-control module 852, a detector module 853, a protocol module 854, an analysis module 855, a pump drive module 857, a valve drive module 859 and an illumination management module 861. Although the modules 851-861 are represented by separate blocks, it is understood that each of the modules may be hardware, software, or a combination of both and that each of the modules may be part of the same component, such as a processor. Alternatively, at least one the modules 851-861 may be part of a separate processor. Moreover, each of the modules 851-861 may communicate with each other or coordinate commands/instructions for performing a particular function.

The computing system 800 and/or the modules 851-861 may include any processor-based or microprocessor-based system, including systems using microcontrollers, reduced instruction set computers (RISC), application specific integrated circuits (ASICs), field programmable gate array (FPGAs), logic circuits, and any logic-based device that is capable of executing functions described herein. The above examples are exemplary only, and are thus not necessarily intended to limit the definition and/or meaning of the terms modules or computing system. In the exemplary example, the computing system 800 and/or the modules 851-861 execute a set of instructions that are stored in one or more storage elements, memories, or modules in order to generate a sample, obtain detection data, and/or analyze the detection data.

The set of instructions may include various commands that instruct the instrument 802 to perform specific operations such as the methods and processes of the various examples described herein. The set of instructions may be in the form of a software program. As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

The software may be in various forms such as system software or application software. Further, the software may be in the form of a collection of separate programs, or a program module within a larger program or a portion of a program module. The software also may include modular programming in the form of object-oriented programming.

The computing system 800 is illustrated conceptually as a collection of modules, but may be implemented utilizing any combination of dedicated hardware boards, DSPs, processors, etc. Alternatively, the computing system 800 may be implemented utilizing an off-the-shelf PC with a single processor or multiple processors, with the functional operations distributed between the processors. As a further option, the modules described herein may be implemented utilizing a hybrid configuration in which certain modular functions are performed utilizing dedicated hardware, while the remaining modular functions are performed utilizing an off-the-shelf PC and the like. The modules also may be implemented as software modules within a processing unit. One or more of the computational modules can be located, for example, in a network or in a cloud computing environment.

As explained herein, the valve drive assembly and pump drive assembly include encoders that transmits signals to the computing system 810 that are indicative of rotational and translational positions of the corresponding components (e.g., the rotor valve and plunger).

In some examples, the detector module 853 may command an imaging assembly (that includes the illumination element 750 and the analysis circuit within the flow cell cartridge) to image a portion of an imaging window (which includes the interface window 410, flow cell window 928 and transparent layer of the analysis circuit 958), which may include commanding an excitation source (the illumination element) to direct an incident light onto the imaging window to excite labels in the sample within the active area of the analysis circuit 958. The detector module 853 communicates through the contact array 752 and contact pads 950 with the analysis circuit 958 to obtain image data. In the case of SBS sequencing, each image includes numerous point sources of light from DNA clusters. Also shown, the fluid-selector module 851 may command the valve drive assembly to move the rotary valve assembly. The fluidic-control module 852 may command the various pumps and valves to control a flow of fluids. The protocol module 854 may include instructions for coordinating the operations of the system 800 so that a designated protocol may be executed. The protocol module 854 may also command any thermal control elements to control a temperature of the fluid. By way of example only, protocol module 854 may be a sequencing-by-synthesis (SBS) module to issue various commands for performing sequencing-by-synthesis processes. In some examples, the protocol module 854 may also process detection data. After generating the amplicons through bridge PCR, the protocol module 854 may provide instructions to linearize or denature the amplicons to make sstDNA and to add a sequencing primer such that the sequencing primer may be hybridized to a universal sequence that flanks a region of interest. Each sequencing cycle extends the sstDNA by a single base and is accomplished by modified DNA polymerase and a mixture of four types of nucleotides delivery of which can be instructed by the protocol module 854. The different types of nucleotides have unique fluorescent labels, and each nucleotide has a reversible terminator that allows only a single-base incorporation to occur in each cycle. After a single base is added to the sstDNA, the protocol module 854 may instruct a wash step to remove non-incorporated nucleotides by flowing a wash solution through the flowcell. The protocol module 854 may further instruct the illumination element and the analysis circuit to perform an image session(s) to detect the fluorescence in each of the four channels (i.e., one for each fluorescent label). After imaging, the protocol module 854 may instruct delivery of a deblocking reagent to chemically cleave the fluorescent label and the terminator from the sstDNA. The protocol module 854 may instruct a wash step to remove the deblocking reagent and products of the deblocking reaction. Another similar sequencing cycle may follow.

Exemplary protocol steps that can be coordinated by protocol module 854 include fluidic and detection steps used in reversible terminator-based SBS methods, for example, as set forth herein or described in US Patent Application Publication No. 2007/0166705 A1, US Patent Application Publication No. 2006/0188901 A1, U.S. Pat. No. 7,057,026, US Patent Application Publication No. 2006/0240439 A1, US Patent Application Publication No. 2006/0281109 A1, PCT Publication No. WO 05/065814, US Patent Application Publication No. 2005/0100900 A1, PCT Publication No. WO 06/064199 and PCT Publication No. WO 07/010251, each of which is incorporated herein by reference in its entirety. Exemplary reagents for reversible terminator-based SBS are described in U.S. Pat. Nos. 7,541,444; 7,057,026; 7,414,116; 7,427,673; 7,566,537; 7,592,435 and WO 07/135368, each of which is incorporated herein by reference in its entirety. Protocol steps and reagents used in commercial sequencing platforms such as the GA, HiSeq® and MiSeq® platforms from Illumina, Inc. (San Diego, Calif.) can also be used.

In some examples, the protocol module 854 may issue various commands for performing the steps of a pyrosequencing protocol. Exemplary steps include those set forth below and in the references cited below. Pyrosequencing detects the release of inorganic pyrophosphate (PPi) as particular nucleotides are incorporated into the nascent strand (Ronaghi, M. et al. (1996) "Real-time DNA sequencing using detection of pyrophosphate release." Analytical Biochemistry 242(1), 84-9; Ronaghi, M. (2001) "Pyrosequencing sheds light on DNA sequencing." Genome Res. 11(1), 3-11; Ronaghi, M. et al. (1998) "A sequencing method based on real-time pyrophosphate." Science 281(5375), 363; U.S. Pat. Nos. 6,210,891; 6,258,568 and 6,274,320, the disclosures of which are incorporated herein by reference in their entireties). In pyrosequencing, released PPi can be detected by being immediately converted to adenosine triphosphate (ATP) by ATP sulfurylase, and the level of ATP generated is detected via luciferase-produced photons. In this case, the reaction valve 816 may include millions of wells where each well has a single capture bead having clonally amplified sstDNA thereon. Each well may also include other smaller beads that, for example, may carry immobilized enzymes (e.g., ATP sulfurylase and luciferase) or facilitate holding the capture bead in the well. The protocol module 854 may issue commands to run consecutive cycles of fluids that carry a single type of nucleotide (e.g., 1st cycle: A; 2nd cycle: G; 3rd cycle: C; 4th cycle: T; 5th cycle: A; 6th cycle: G; 7th cycle: C; 8th cycle: T; and on). When a nucleotide is incorporated into the DNA, pyrophosphate is released thereby instigating a chain reaction where a burst of light is generated. The burst of light may be detected by the detector assembly. Detection data may be communicated to the analysis module 855 for processing.

In some examples, the user may provide user inputs through the user interface to select an assay protocol to be run by the system. In other examples, the system may automatically detect the type of flow cell cartridge that has been inserted into the instrument 802 and confirm with the user the assay protocol to be run. Alternatively, the system may offer a limited number of assay protocols that could be run with the determined type of flow cell cartridge. The user may select the desired assay protocol, and the system may then perform the selected assay protocol based on preprogrammed instructions.

The analysis module 855 may analyze detection data that is obtained by the analysis circuit within the flow cell cartridge. Although not shown, the instrument may also include a user interface that interacts with the user. For example, the user interface may include a display to display or request information from a user and a user input device to receive user inputs. In some examples, the display and the user input device are the same device (e.g., touch-sensitive display).

In some examples, nucleic acids can be attached to a surface and amplified prior to or during sequencing. Protocol module 854 can include instructions for the fluidic steps involved in an amplification process. For example, instructions can be provided for a bridge amplification technique used to form nucleic acid clusters on a surface. Useful bridge amplification methods are described, for example, in U.S. Pat. No. 5,641,658; U.S. Patent Publ. No. 2002/0055100; U.S. Pat. No. 7,115,400; U.S. Patent Publ. No. 2004/0096853; U.S. Patent Publ. No. 2004/0002090; U.S. Patent Publ. No. 2007/0128624; and U.S. Patent Publ. No. 2008/0009420. Another useful method for amplifying nucleic acids on a surface is rolling circle amplification (RCA), for example, as described in Lizardi et al., Nat. Genet. 19:225-232 (1998) and US 2007/0099208 A1, each of which is incorporated herein by reference. Emulsion PCR on beads can also be used, for example as described in Dressman et al., Proc. Natl. Acad. Sci. USA 100:8817-8822 (2003), WO 05/010145, or U.S. Patent Publ. Nos. 2005/0130173 or 2005/0064460, each of which is incorporated herein by reference in its entirety.

In some examples, the system is operated with minimal user intervention. For example, the generating and analyzing operations may be conducted in an automated manner by an assay system. In some cases, a user may only load the cartridge assembly and activate the instrument to perform the protocol.

Flow Cell Cartridge

Next, a flow cell cartridge 900 is utilized in accordance with at least one example herein.

Figure 9A:
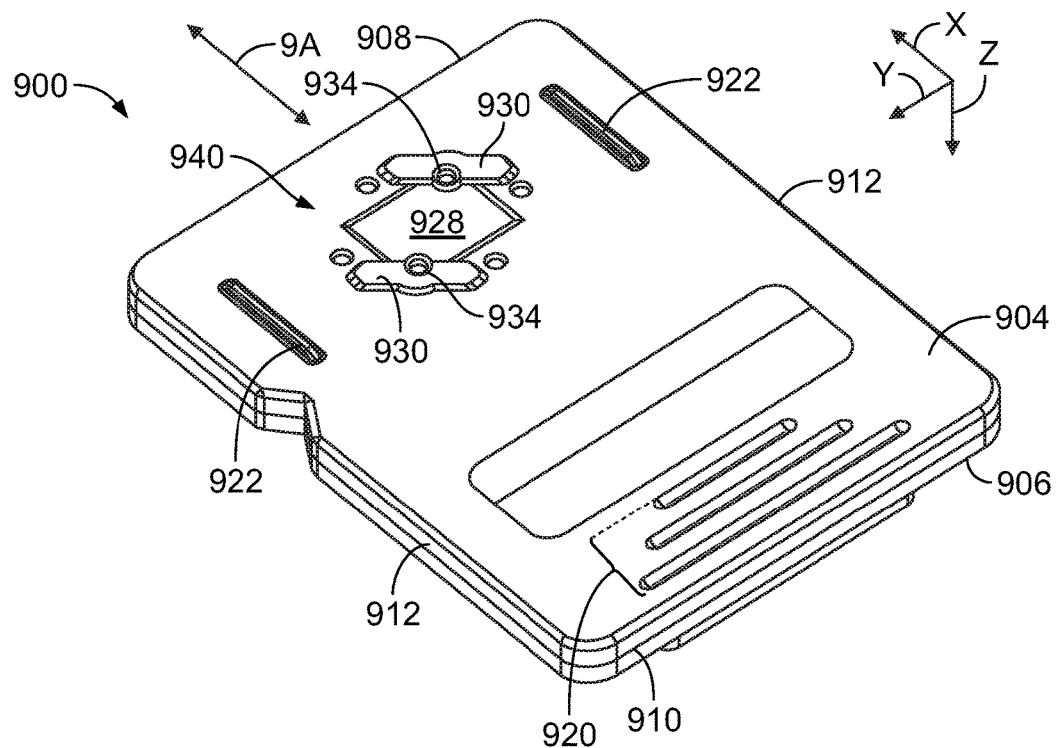
FIG. 9A illustrates a top perspective view of a flow cell cartridge formed in accordance with an example herein.

FIG. 9A illustrates a top perspective view of a flow cell cartridge 900 formed in accordance with an example herein. The flow cell cartridge 900 generally includes top and bottom frames 904 and 906 that are joined to form a generally rectangular structure that is elongated along a loading direction 9A. The loading direction 9A corresponds to the direction in which the flow cell cartridge 900 is loaded into the flow cell chamber 108 of the cartridge assembly 100. The flow cell cartridge 900 includes a loading end 908, a trailing end 910, and lateral side edges 912. The loading end 908 and side edges 912 include one or more positioning features to mate with corresponding features within the flow cell chamber 108 of the cartridge assembly 100 to ensure proper alignment within the flow cell chamber 108 in the XYZ directions.

Optionally, the top and bottom frames 904 and 906 may be formed from a conductive plastic, such as to provide electrostatic discharge (ESD) protection.

Optionally, the top frame 904 may include a gripping feature 920, such as a series of ribs extending upward from the top frame 904. The gripping features 920 facilitate gripping of the flow cell cartridge 900 by a user. Optionally, the grooves within the gripping feature 920 may be shaped to form an indication of direction, such as by shaping the ribs to form an arrow, thereby to further provide information to a user regarding a direction in which the flow cell cartridge 900 should be inserted.

Figure 9B:
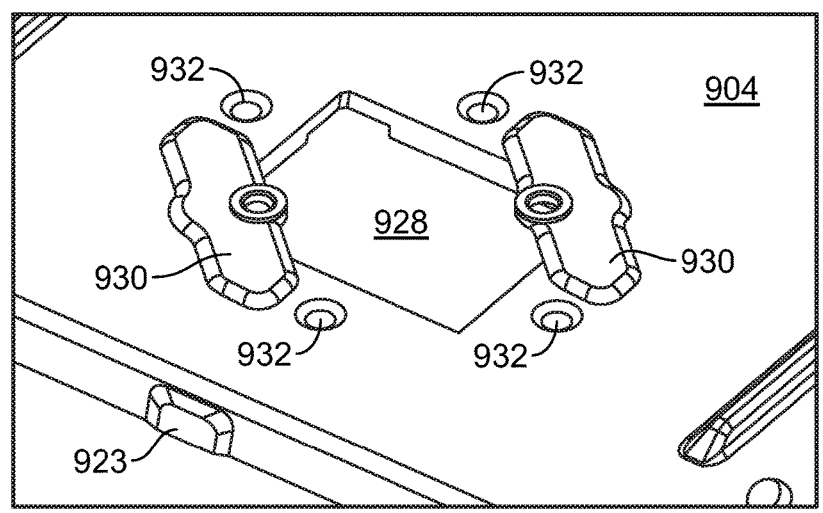
FIG. 9B illustrates an enlarged view of a portion of the top frame to better illustrate an optical fluidic (O-F) interface to the flow cell cartridge in accordance with examples herein.

FIG. 9B illustrates an enlarged view of a portion of the top frame 904 to better illustrate an optical fluidic (O-F) interface to the flow cell cartridge. With joint reference to FIGS. 9A and 9B, the top frame 904 includes an O-F interface 940 to communicate with optical and fluidics components of the cartridge assembly 100. The O-F interface 940 includes a flow cell window 928 aligned with an analysis circuit (and described below in more detail in connection with FIGS. 9D and 9E) that is housed within the flow cell cartridge 900. The flow cell window 928 permits light from an illumination element of the instrument to be directed onto the analysis circuit. The flow cell window 928 may be formed from glass or a similar transparent material, with the glass arranged in a substantially common plane with an upper surface of the top frame 904. By maintaining the glass within the flow cell window 928 in a planar alignment with the upper surface of the top frame 904, the Z position of flow cell window 928 may be more accurately monitored by monitoring the Z position of the upper surface of the top frame 904.

Flow cell ports 934 are located proximate to the flow cell window 928, where the flow cell ports 934 convey fluid from the cartridge assembly 100 through an active area within the analysis circuit. The ports 934 are provided within gasket seals 930 that are formed in an elongated manner. In the example of FIG. 9A, the gasket seals 930 are oriented to extend generally parallel to one another and arranged at an acute angle relative to the loading direction 9A. The flow cell ports 934 within the gasket seals 930 are positioned to mate with corresponding ports within the flow cell chamber 108 of the cartridge assembly 100.

Seals 930 are provided on opposite sides of the flow cell window 928. By way of example, the seals 930 may be oriented diagonally across the flow cell window 928 from one another. The seals 930 may be formed from TPE or another similar material. The seals 930 fit in cavities formed in the top frame 904 that are in fluid communication with injection gates 932. During a manufacturing process, TPE is injected through the injection gates 932 and permitted to flow through an internal channel within the top frame until forming as the seals 930. The injection molding process both physically and chemically bonds the seals 930 to the top frame 904 in order to maintain the seals 930 at a predefined position on the top frame 904 (to remain within a select tolerance). The gasket seals 930 provide a low profile, miniaturized seal configuration that affords a desired tolerance buildup (e.g. minimizing tolerance buildup).

Returning to FIG. 9A, the top frame 904 includes ribs 922 that are elongated and oriented to extend in a direction common (e.g. parallel) with the loading direction 9A. The ribs 922 provide a loading protection feature such that, as the flow cell cartridge 900 is loaded into the flow cell chamber, the gasket seals 930 and flow cell ports 934 do not contact or otherwise engage housing features surrounding the flow cell chamber 108. In addition, the ribs 922 may provide a standoff feature, such that in the event that the flow cell cartridge 900 is laid upside down on a table or other structure, the ribs 922 may prevent other features on the top frame 904 from touching dust and other material on a surface where the flow cell cartridge 900 is placed.

The top frame 904 includes one or more Z-position features (corresponding to a Z-datum point) that is utilized to register the LED light tube within the illumination element of the instrument to the flow cell window 928 of the flow cell cartridge 900. For example, the top surface of the top frame 904 abuts against the ribs 472 and pad 473 on the bottom surface of the well plate 150 to define a Z datum point for the flow cell cartridge 900. The Z-position limit feature affords a desired tolerance (e.g. a minimized tolerance) between the light source of the illumination element in the instrument and the flow cell cartridge.

Figure 9C:
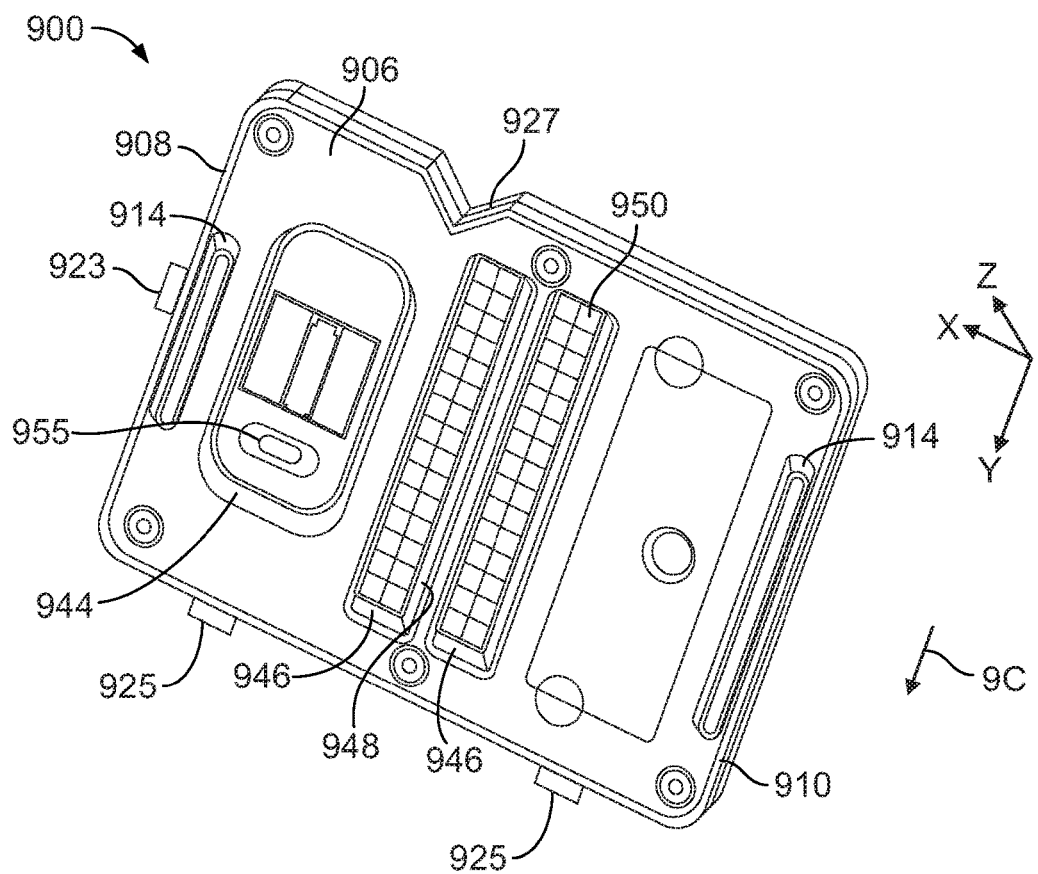
FIG. 9C illustrates a bottom perspective view of the flow cell cartridge of FIG. 9A in accordance with examples herein.

FIG. 9C illustrates a bottom perspective view of the flow cell cartridge of FIG. 9A. The lower shell 906 is formed with one or more standoffs 914 that are located near the loading and trailing ends 908 and 910. Optionally, the standoffs 914 may be located in other positions on the bottom frame 906. Additionally or alternatively, more or fewer standoffs 914 may be utilized. The standoffs 914 maintain a predetermined spacing between the features within the bottom frame 906 and any surface on which the flow cell cartridge 900 is set. For example, when storing the cartridge 900 on a desk, lab bench, storage area or otherwise, the standoffs 914 prevent the features in the bottom frame 906 from contacting dust and other particulate material on the desk, lab bench and the like. In addition, the standoffs 914 may be shaped and dimensioned as alignment keying features to prevent the flow cell cartridge 900 from being inserted incorrectly into the cartridge assembly 100 (e.g. backwards). For example, the standoffs 914 may be formed with different sizes, such as different lengths, thicknesses, standoff heights and the like. In the example of FIG. 9C, the standoff 914 that is proximate to the loading end 908 is shorter in length, as compared to a length of the standoff 914 that is located proximate to the trailing end 910.

The bottom frame 906 includes an opening 944 that is aligned with the optical-fluidics interface 940 on the top frame 904 (and the heat spreader 955 on the PCB 952). The opening 944 exposes a back side of a portion of the analysis circuit. The bottom frame 906 also includes contact pad openings 946 that are aligned with and expose arrays of contact pads 950 that are provided with the analysis circuit. The contact pad openings 946 are separated by a cross bar 948 that maintains a width of the contact pad openings 946 sufficiently small to prevent inadvertent insertion of undesired objects that might otherwise damage the contact pads 950 (e.g., a user's finger, test equipment, etc.). In the present example, the contact pad openings 946 are rectangular and each expose two or more rows of contact pads 950.

Figure 9D:
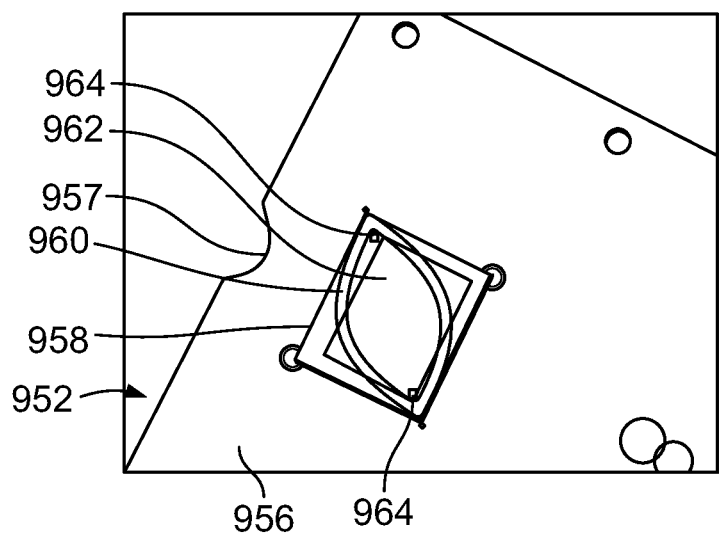
FIG. 9D illustrates a top view of a portion of a printed circuit board provided within the flow cell cartridge formed in accordance with an example herein.

FIG. 9D illustrates a top view of a portion of a printed circuit board 952 provided within the flow cell cartridge 900 formed in accordance with an example herein. The printed circuit board 952 includes a top surface 956 that includes an analysis circuit 958. By way of example, the analysis circuit 958 may represent a CMOS circuit. The analysis circuit 958 is to support flow of fluids crossing an active area 962, received incoming light from an illumination source within the instrument, and detect and capture digital images of the fluorescence emitted from the fluid in connection with a fluidics analysis operation. The analysis circuit 958 includes ports 964 that communicate with the active area 962 within the analysis circuit 958. The fluids enter the active area 962 through one of active area ports 964 and the fluid exits the active area 962 through the other of the active area ports 964. The analysis circuit 958 includes a top surface that is transparent to receive light that is emitted through the flow cell window 928 (and through window 410 of FIG. 4). The incoming light illuminates the fluids in the active area 962, and in response thereto, reagents within the fluid emitted fluorescence within different fluorescent spectrums depending upon the characteristics of the sample. The analysis circuit 958 detects the emitted fluorescent spectrums and captures images thereof that are then conveyed through the contact pads 950 to the instrument.

Figure 9E:
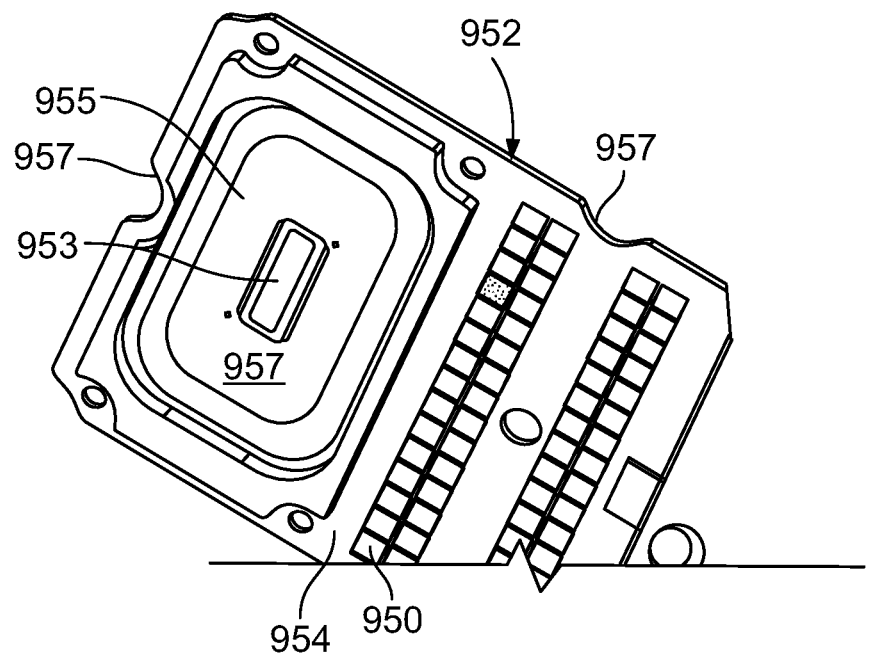
FIG. 9E illustrates a bottom view of the printed circuit board of FIG. 9D formed in accordance with an example herein.

FIG. 9E illustrates a bottom view of the printed circuit board 952 of FIG. 9D formed in accordance with an example herein. The PCB 952 includes a bottom surface 954 that includes the array of contact pads 950 visible through the contact pad openings 946. In the present example, the array of contact pads 950 are formed in multiple rows. Optionally, alternative contact array configurations may be utilized. The contact pads 950 are connected to corresponding pins within a socket connector 953. The socket connector 953 includes a plurality of contact pins facing in the direction of the top surface 956 (FIG. 9D). The socket connector 953 securely receives the analysis circuit 958 and provides power, data and communications connections between the inputs/outputs of the analysis circuit 958 and the contact pads 950.

The bottom surface 954 also includes a heat spreader 955 that includes a circuit engaging face (not visible in FIG. 9D) that abuts against a bottom surface of the analysis circuit 958. The heat spreader 955 includes a heat element engaging face 957 that is oriented to face downward through the opening 944 in the bottom frame 906 (FIG. 9C). During operation, a heating element on the instrument is inserted into the opening 944 to abut against the heat element engaging face 957 of the heat spreader 955, in connection with providing the desired amount of heat to the analysis circuit 958.

The printed circuit board 952 also includes indents 957 provided about a perimeter thereof. The indents 957 mate with corresponding features within the top and bottom frames 904, 906 to position the printed circuit board 952 at a particular location within the top and bottom frames 904 and 906.

The top and bottom frames 904 and 906 also include one or more XY-position features (corresponding to XY-datum points) that are utilized to register the flow cell cartridge 900 in the XY direction within the flow cell chamber 108. The XY position features include a front reference post 923 provided on the loading end 908 and one or more lateral reference posts 925 provided along one or both side edges 912. A notch 927 is provided in a side edge 912 on the side opposite the lateral reference posts 925.

During a loading operation, the loading end 908 is inserted into the flow cell chamber 108 until the reference post 923 firmly abuts against a limit feature in the flow cell chamber 108 to define a limit of movement in the loading direction 9A (also referred to as the X direction). As flow cell cartridge 900 is inserted, a biasing arm rides along the side edge 912 that includes the notch 927 until a latch element fits within the notch 927. The latch element is shaped to conform to the shape of the notch 927. The biasing arm applies a lateral force in the direction of arrow 9C (also represents a lateral positioning force) to shift the flow cell cartridge 900 in the lateral direction (corresponding to the Y-axis) until the lateral reference posts 925 engage mating features within the flow cell chamber 108. When the lateral reference posts 925 engage the mating features, the flow cell chamber 108 defines a limit of movement in the lateral direction 9C. The biasing arm maintains the flow cell cartridge 900 at the desired Y-position (corresponding to a Y datum point). The latch element on the biasing arm fits within the notch 927 at a predefined position to maintain the flow cell cartridge 900 at the desired X-position (corresponding to an X datum point).

Once the flow cell cartridge 900 is inserted to the XYZ datum points, a communications connector is inserted (in the Z direction) into the contact pad openings 946 until a mating array of contacts on the communications connector engage the contact pads 950. The communications connector provides power, collects data and controls the operation of, the analysis circuit in the flow cell cartridge 900. In addition, a heating element is inserted (in the Z direction) into the opening 944 until engaging the heat spreader 955.

ADDITIONAL EXAMPLES

Example 1

A cartridge assembly, comprising: a housing including a flow cell chamber to receive a flow cell; a well plate having liquid wells to receive desired amounts of liquids, the well plate including a valve station, a pump station and a fluidics analysis station, the well plate including channels associated with the wells, the valve station, pump station and fluidics analysis station; a pump assembly provided on the well plate at the pump station, the pump assembly to manage fluid flow through the channels between the pump station and the fluidics analysis station; and a rotary valve assembly positioned on the well plate at the valve station, the rotary valve assembly including a rotor shaft and rotor valve positioned to rotate about a rotational axis and to selectively couple the wells to the pump station, the rotor shaft having a distal end exposed through the housing, the rotor shaft including a dual spline configuration at the distal end thereof, the dual spline configuration having first and second sets of splines, the first set of splines forming a drive interface, the second set of splines forming a position encoding interface.

Example 2

The cartridge assembly of Example 1, wherein the distal end of the rotor shaft extends into a shaft well provided in the housing, thereby exposing the dual spline configuration to a valve drive assembly of a fluidics analysis instrument.

Example 3

The cartridge assembly of Example 1, wherein the first set of splines represent exterior splines extending about an exterior of the distal end, wherein lateral sides of adjacent splines are separated by a first predetermined spline to spline spacing, the spline to spline spacing corresponds to a spline pattern on a drive shaft of a valve drive assembly.

Example 4

The cartridge assembly of Example 1, wherein the second set of splines represent interior splines formed about an interior of a cavity provided at the distal end of the rotor shaft, the interior splines having lateral sides that are angled such that adjacent lateral sides form a predetermined non-parallel angle with respect to one another, wherein the adjacent lateral sides merge at a bottom to form pockets to receive mating splines on a drive shaft of the valve drive assembly, the position encoding interface utilized by the valve drive assembly to track a position of the rotor shaft.

Example 5

The cartridge assembly of Example 1, wherein the rotor valve is mounted to a proximal end of the rotor shaft through a coupling flange, the coupling flange to allow a predetermined amount of tilting movement between the rotor valve and rotor shaft.

Example 6

The cartridge assembly of Example 4, wherein the rotor valve including a rotor base having one or more ribs positioned about a proximal end of the rotor shaft, the coupling flange held between the ribs and the proximal end of the rotor shaft.

Example 7

The cartridge assembly of Example 1, wherein rotor valve includes well plate engaging face having a central port and a radial port, the rotor valve including a channel oriented to extend in a radial direction outward from the central port to the radial port.

Example 8

The cartridge assembly of Example 6, wherein the central port is aligned to correspond with a rotational axis of the rotor shaft and to align with a central feed port in the well plate, the rotor valve to rotate about the rotational axis to align the radial port with a corresponding well port.

Example 9

The cartridge assembly of Example 1, wherein the rotary valve includes a well plate engaging face formed with an interface ring thereon, the interface ring extending about a perimeter of the well plate engaging face.

Example 10

The cartridge assembly of Example 1, further comprising: a valve cap including an interior cavity to rotatably receive the rotary valve, the valve cap including one or more latch arms to secure the valve cap to the wells and downward against the well plate; and a biasing element provided within the interior cavity and to apply a biasing force against the rotary valve to maintain a sealed interface between ports in the rotary valve and ports in the well plate.

Example 11

The cartridge assembly of Example 1, wherein the pump assembly includes a plunger having a drive end and a biasing surface located at opposite ends of the plunger, the drive end and biasing surface exposed at upper and lower surfaces of the housing such that corresponding unidirectional drive and biasing forces are applied thereto in connection with moving the plunger in a reciprocating motion.

Example 12

The cartridge assembly of Example 11, wherein the plunger has a drive arm and a plunger arm joined with one another through a bridge segment in a U-shape and are formed together in a monolithic structure, the drive and plunger arms to be received within support posts located on the well plate.

Example 13

The cartridge assembly of Example 11, wherein the plunger comprises a plunger arm and plunger element that are molded together from different materials.

Example 14

The cartridge assembly of Example 13, wherein the plunger element is formed on a leading end of the plunger arm, the plunger element to move within the corresponding support post to form high and low pressure states at the pumping station.

Example 15

The cartridge assembly of Example 1, wherein the pump station includes a channel segment functionally divided into a preparation segment, a discharge segment and a pump work segment, all of which are formed continuous with one another to support fluid flow in either direction.

Example 16

The cartridge assembly of Example 1, wherein the pump station includes an work area sandwiched between a pair of pinch valves located upstream and downstream of the work area, the pump assembly comprising a plunger aligned with the work area, the plunger to reciprocally move toward and away from the work area to introduce high and low pressure states, the pump assembly further comprising push pins aligned with the pinch valves, the push pins to be alternately moved to open and close the pinch valves.

Example 17

The cartridge assembly of Example 1, further comprising a piercer unit provided in the housing and positioned proximate to the wells, the piercer unit including a piercer element, the piercer unit to be moved to a piercing position where the piercer element pierces a cover for the corresponding well.

Example 18

The cartridge assembly of Example 17, wherein the housing includes a cover having a piercer access opening that provides an instrument access to an upper end of the piercer unit.

Example 19

The cartridge assembly of Example 17, wherein the piercer unit includes a body that is shaped in a conical tubular manner with a lower platform, an intermediate segment and an upper flange, at least one of the lower platform or upper flange including piercing elements distributed in a predetermined manner, the piercing elements arranged to align with the wells on the well plate.

Example 20

The cartridge assembly of Example 1, further comprising a piercer unit having a platform that fits over the rotor shaft, the platform including indexing features that engage mating features on the rotary valve assembly to locate the piercer unit in a predetermined rotational orientation with respect to the rotor shaft in order to align piercer elements with corresponding wells.

Example 21

The cartridge assembly of Example 1, wherein the well plate includes well transition ports arranged in a predetermined pattern corresponding to the rotary valve assembly, the well plate including well discharge ports aligned with corresponding wells, the well plate including well discharge channels extending between corresponding well discharge ports and well transition ports.

Example 22

The cartridge assembly of Example 1, wherein the well plate includes a base having top and bottom surfaces, at least one of which includes the channels, the channels including open sided channels, the base joined to a backing layer to close the open sided channels.

Example 23

The cartridge assembly of Example 1, wherein the well plate includes an optical interface window, provided within the optical analysis station, a top side of the well plate including an insertion limit element to engage an illumination element on an instrument.

Example 24

The cartridge assembly of Example 23, wherein the insertion limit element represents one or more ribs that are provided about the optical interface window, the ribs defining a Z-tolerance between an illumination element and the optical interface window.

Example 25

A fluidics system, comprising: a cartridge assembly having a housing that includes an illumination chamber and a well plate, the well plate maintained within the housing and having liquid wells to receive desired amounts of liquids, the well plate including a fluidics analysis station aligned with the illumination chamber, the well plate including an interface window and interface ports located at the fluidics analysis station; and a flow cell cartridge having a frame that contains an analysis circuit therein, the frame including a flow cell window aligned with the analysis circuit, the frame including flow cell ports that are fluidly coupled to an active area in the analysis circuit, the housing including a flow cell chamber to receive the flow cell cartridge, the flow cell chamber to position the flow cell cartridge at the fluidics analysis station with the flow cell window and ports aligned with the corresponding interface window and ports, respectively.

Example 26

The fluidics system of Example 25, wherein the flow cell chamber includes side rails and an end stop, at least one of which has an end limit to position the flow cell cartridge, when in a fully loaded position, at a predetermined datum point such that the flow cell window and ports aligned with the corresponding interface window and ports, respectively.

Example 27

The fluidic system of Example 26, wherein the flow cell chamber includes a biasing arm that is oriented to extend along at least one of the side rails, the biasing arm extending inward toward the flow cell chamber, the biasing arm to apply a lateral biasing force upon the flow cell cartridge to maintain the flow cell cartridge at the predetermined datum point.

Example 28

The fluidic system of Example 27, wherein the biasing arm includes a latch element positioned to fit with a notch provided in a lateral side of the flow cell cartridge, the latch element to maintain the flow cell cartridge at an X datum point.

Example 29

The fluidic system of Example 25, wherein the flow cell cartridge includes top and bottom frames, the top frame including the flow cell window and ports, the top frame including a rib extending upward from the top frame by a predetermined height to define a Z datum point.

Example 30

The fluidic system of Example 25, wherein the flow cell cartridge includes gaskets formed in a monolithic manner from an elastomer material.

Example 31

The fluidic system of Example 25, wherein the well plate includes a valve station, pump station and interface channels, the interface channels providing a first fluidic path between the valve station and one of the interface ports and a second fluidic path between the pump station and one of the interface ports.

Example 32

The fluidic system of Example 25, wherein the illumination chamber is oriented to extend along an illumination axis that extends through the interface window, flow cell window and the active area within the analysis circuit.

Closing Statements

It should be appreciated that all combinations of the foregoing concepts (provided such concepts are not mutually inconsistent) are contemplated as being part of the inventive subject matter disclosed herein. In particular, all combinations of aforementioned Examples and claimed subject matter appearing at the end of this disclosure are contemplated as being part of the inventive subject matter disclosed herein.

All publications, patents, and patent applications cited in this Specification are hereby incorporated by reference in their entirety.

It will be appreciated that various aspects of the present disclosure may be embodied as a method, system, computer readable medium, and/or computer program product. Aspects of the present disclosure may take the form of hardware examples, software examples (including firmware, resident software, micro-code, etc.), or examples combining software and hardware aspects that may all generally be referred to herein as a "circuit," "module," or "system." Furthermore, the methods of the present disclosure may take the form of a computer program product on a computer-usable storage medium having computer-usable program code embodied in the medium.

Any suitable computer useable medium may be utilized for software aspects of the present disclosure. The computer-usable or computer-readable medium may be, for example but not limited to, an electronic, magnetic, optical, electromagnetic, infrared, or semiconductor system, apparatus, device, or propagation medium. The computer readable medium may include transitory examples. More specific examples (a non-exhaustive list) of the computer-readable medium would include some or all of the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a transmission medium such as those supporting the Internet or an intranet, or a magnetic storage device. Note that the computer-usable or computer-readable medium could even be paper or another suitable medium upon which the program is printed, as the program can be electronically captured, via, for instance, optical scanning of the paper or other medium, then compiled, interpreted, or otherwise processed in a suitable manner, if necessary, and then stored in a computer memory. In the context of this document, a computer-usable or computer-readable medium may be any medium that can contain, store, communicate, propagate, or transport the program for use by or in connection with the instruction execution system, apparatus, or device.

Program code for carrying out operations of the methods and apparatus set forth herein may be written in an object oriented programming language such as Java, Smalltalk, C++ or the like. However, the program code for carrying out operations of the methods and apparatus set forth herein may also be written in conventional procedural programming languages, such as the "C" programming language or similar programming languages. The program code may be executed by a processor, application specific integrated circuit (ASIC), or other component that executes the program code. The program code may be simply referred to as a software application that is stored in memory (such as the computer readable medium discussed above). The program code may cause the processor (or any processor-controlled device) to produce a graphical user interface ("GUI"). The graphical user interface may be visually produced on a display device, yet the graphical user interface may also have audible features. The program code, however, may operate in any processor-controlled device, such as a computer, server, personal digital assistant, phone, television, or any processor-controlled device utilizing the processor and/or a digital signal processor.

The program code may locally and/or remotely execute. The program code, for example, may be entirely or partially stored in local memory of the processor-controlled device. The program code, however, may also be at least partially remotely stored, accessed, and downloaded to the processor-controlled device. A user's computer, for example, may entirely execute the program code or only partly execute the program code. The program code may be a stand-alone software package that is at least partly on the user's computer and/or partly executed on a remote computer or entirely on a remote computer or server. In the latter scenario, the remote computer may be connected to the user's computer through a communications network.

The methods and apparatus set forth herein may be applied regardless of networking environment. The communications network may be a cable network operating in the radial-frequency domain and/or the Internet Protocol (IP) domain. The communications network, however, may also include a distributed computing network, such as the Internet (sometimes alternatively known as the "World Wide Web"), an intranet, a local-area network (LAN), and/or a wide-area network (WAN). The communications network may include coaxial cables, copper wires, fiber optic lines, and/or hybrid-coaxial lines. The communications network may even include wireless portions utilizing any portion of the electromagnetic spectrum and any signaling standard (such as the IEEE 802 family of standards, GSM/CDMA/TDMA or any cellular standard, and/or the ISM band). The communications network may even include powerline portions, in which signals are communicated via electrical wiring. The methods and apparatus set forth herein may be applied to any wireless/wireline communications network, regardless of physical componentry, physical configuration, or communications standard(s).

Certain aspects of present disclosure are described with reference to various methods and method steps. It will be understood that each method step can be implemented by the program code and/or by machine instructions. The program code and/or the machine instructions may create means for implementing the functions/acts specified in the methods.

The program code may also be stored in a computer-readable memory that can direct the processor, computer, or other programmable data processing apparatus to function in a particular manner, such that the program code stored in the computer-readable memory produce or transform an article of manufacture including instruction means which implement various aspects of the method steps.

The program code may also be loaded onto a computer or other programmable data processing apparatus to cause a series of operational steps to be performed to produce a processor/computer implemented process such that the program code provides steps for implementing various functions/acts specified in the methods of the present disclosure.

What is claimed is:

1. A cartridge assembly, comprising:
a housing including a flow cell chamber to receive a flow cell;
a well plate having liquid wells to receive amounts of liquids, the well plate including a valve station, a pump station and a fluidics analysis station, the well plate including channels fluidly connected with the wells, the valve station, pump station and fluidics analysis station;
a pump assembly provided on the well plate at the pump station, the pump assembly to manage fluid flow through the channels between the pump station and the fluidics analysis station; and
a rotary valve assembly positioned on the well plate at the valve station, the rotary valve assembly including a rotor shaft and a rotor valve positioned to rotate about a rotational axis and to selectively couple the wells to the pump station,
the rotor shaft having a distal end exposed through the housing,
the rotor shaft including a dual spline configuration at the distal end thereof, the dual spline configuration having first and second sets of splines, the first set of splines forming a drive interface, the second set of splines forming a position encoding interface.

2. The cartridge assembly of claim 1, wherein the distal end of the rotor shaft extends into a shaft well provided in the housing, thereby exposing the dual spline configuration to a valve drive assembly of a fluidics analysis instrument.

3. The cartridge assembly of claim 1, wherein the first set of splines are exterior splines extending about an exterior of the distal end of the rotor shaft, wherein lateral sides of adjacent splines are separated by a first predetermined spline to spline spacing, the first predetermined spline to spline spacing corresponds to a spline pattern on a drive shaft of a valve drive assembly.

4. The cartridge assembly of claim 1, wherein the second set of splines are interior splines formed about an interior of a cavity provided at the distal end of the rotor shaft, the interior splines having lateral sides that are angled such that adjacent lateral sides form a predetermined non-parallel angle with respect to one another, wherein the adjacent lateral sides merge at a bottom of the interior splines to form pockets to receive mating splines on a drive shaft of a valve drive assembly, the position encoding interface utilized by the valve drive assembly to track a position of the rotor shaft.

5. The cartridge assembly of claim 1, wherein the rotor valve is mounted to a proximal end of the rotor shaft through a coupling flange, the coupling flange to allow a predetermined amount of tilting movement between the rotor valve and rotor shaft.

6. The cartridge assembly of claim 1, wherein the rotor valve is mounted to a proximal end of the rotor shaft through a coupling flange, the rotor valve including a rotor base having one or more ribs positioned about a proximal end of the rotor shaft, the coupling flange held between the ribs and the proximal end of the rotor shaft.

7. The cartridge assembly of claim 1, wherein rotor valve includes a well plate engaging face having a central port and a radial port, the rotor valve including a channel oriented to extend in a radial direction outward from the central port to the radial port.

8. The cartridge assembly of claim 1, wherein the rotor valve includes a well plate engaging face having a central port and a radial port, wherein the central port is aligned to correspond with a rotational axis of the rotor shaft and to align with a central feed port in the well plate, the rotor valve to rotate about the rotational axis to align the radial port with a corresponding well port.

9. The cartridge assembly of claim 1, wherein the rotary valve includes a well plate engaging face formed with an interface ring thereon, the interface ring extending about a perimeter of the well plate engaging face.

10. The cartridge assembly of claim 1, further comprising:
a valve cap including an interior cavity to rotatably receive the rotary valve, the valve cap including one or more latch arms to secure the valve cap to the wells and downward against the well plate; and
a biasing element provided within the interior cavity and to apply a biasing force against the rotary valve to maintain a sealed interface between ports in the rotary valve and ports in the well plate.

11. The cartridge assembly of claim 1, wherein the pump assembly includes a plunger having a drive end and a biasing surface located at opposite ends of the plunger, the drive end and biasing surface exposed at upper and lower surfaces of the housing such that corresponding unidirectional drive and biasing forces are applied thereto in connection with moving the plunger in a reciprocating motion.

12. The cartridge assembly of claim 11, wherein the plunger has a drive arm and a plunger arm joined with one another through a bridge segment in a U-shape and are formed together in a monolithic structure, the drive and plunger arms to be received within support posts located on the well plate.

13. The cartridge assembly of claim 1, wherein the first set of splines have beveled edges to facilitate alignment of a drive shaft of a valve drive assembly with the distal end of the rotor shaft.

14. The cartridge assembly of claim 4, wherein the lateral sides of each spline in the second set of splines extend in a V-shape to form a 30 degree angle.

15. The cartridge assembly of claim 4, wherein the drive shaft operates at an angle to the rotational axis of the rotor shaft.

16. The cartridge assembly of claim 1, wherein the well plate includes well transition ports arranged in a predetermined pattern corresponding to the rotary valve assembly.

* * * * *